United States Patent [19]

Ikeda et al.

[11] Patent Number: 6,048,854
[45] Date of Patent: Apr. 11, 2000

[54] 2,3-DIAMINOPROPIONIC ACID DERIVATIVE

[75] Inventors: Yoshiharu Ikeda, Hyogo-ken; Yasuyuki Ueki, Sanda; Hisakazu Kishimoto, Iabaraki; Toshio Nishihara, Nishinomiya; Yumiko Kamikawa, Nara, all of Japan

[73] Assignee: Sumitomo Pharmaceuticals Company, Limited, Osaka-fu, Japan

[21] Appl. No.: 08/937,901

[22] Filed: Sep. 25, 1997

Related U.S. Application Data

[62] Division of application No. 08/633,800, filed as application No. PCT/JP94/01700, Oct. 11, 1994, Pat. No. 5,707,994.

[30] Foreign Application Priority Data

Oct. 19, 1993 [JP] Japan .................................. 6-286091
Dec. 28, 1993 [JP] Japan .................................. 6-350177

[51] Int. Cl.$^7$ ..................... C07D 217/22; C07D 471/04; A61K 31/445; A61K 31/495
[52] U.S. Cl. .................... 514/213; 514/215; 514/248; 514/255; 514/300; 514/315; 540/578; 540/580; 540/593; 544/236; 544/362; 544/363; 546/122; 546/123; 546/143
[58] Field of Search ...................... 514/213, 215, 514/248, 255, 300, 315; 540/578, 580, 593; 544/236, 362, 363; 546/122, 123, 143

[56] References Cited

U.S. PATENT DOCUMENTS

| | | | |
|---|---|---|---|
| 4,069,323 | 1/1978 | Okamoto et al. | 424/244 |
| 4,097,591 | 6/1978 | Okamoto et al. | 424/177 |
| 4,133,880 | 1/1979 | Okamoto et al. | 424/244 |
| 4,861,798 | 8/1989 | Tramposch et al. | 514/575 |
| 5,086,069 | 2/1992 | Klein et al. | 514/399 |
| 5,272,158 | 12/1993 | Hartman et al. | 514/323 |
| 5,409,939 | 4/1995 | Adams et al. | 514/335 |
| 5,494,921 | 2/1996 | Egbertson et al. | 514/331 |
| 5,563,158 | 10/1996 | DeGrado et al. | 514/340 |

FOREIGN PATENT DOCUMENTS

| | | |
|---|---|---|
| 0478363 | 4/1992 | European Pat. Off. . |
| 0512829 | 11/1992 | European Pat. Off. . |
| 0512831 | 11/1992 | European Pat. Off. . |
| 52-31061 | 3/1977 | Japan . |
| 4288051 | 10/1992 | Japan . |
| 9412181 | 6/1994 | WIPO . |

*Primary Examiner*—Mukund J. Shah
*Assistant Examiner*—Deepak R. Rao
*Attorney, Agent, or Firm*—Birch, Stewart, Kolasch & Birch, LLP

[57] ABSTRACT

The present invention relates to a 2,3-diaminopropionic acid derivative of the formula (1):

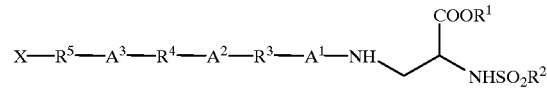

or a pharmaceutically acceptable salt thereof. The compounds of the present invention are useful as a platelet aggregation inhibitor, a cancer metastasis inhibitor, a wound healing agent or a bone resorption inhibitor.

14 Claims, No Drawings

2,3-DIAMINOPROPIONIC ACID DERIVATIVE

This application is a divisional of application Ser. No. 08/633,800 filed on Apr. 19, 1996 now U.S. Pat. No. 5,707,994 the entire contents of which are hereby incorporated by reference which is a 371 of PCT/JP94/01700 filed Oct. 11, 1994.

TECHNICAL FIELD

The present invention relates to a novel 2,3-diaminopropionic acid derivative being useful as a platelet aggregation inhibitor, a cancer metastasis inhibitor, a wound healing agent or a bone resorption inhibitor.

BACKGROUND ART

Proteins, which participate in adhesion between a cell and an interstitial connective tissue and show various biological activities concerning the cell functions of animal cells, are called cell adhesive proteins. For example, there are known fibronectin, vitronectin, laminin, etc. It is known that the core sequence of the cell adhesion site of these proteins is arginine-glycine-aspartic acid [Arg—Gly—Asp] (hereinafter, occasionally referred to as RGD) [Pierschbachr, M. D., et al., Nature, 309, 30 (1984), Suzuki, S., et al., J. Biol. Chem., 259, 15307 (1984), Plow, E., et al., Proc. Natl. Acad. Sci. USA, 82, 8057 (1985)]. The RGD interacts with a receptor of a cell adhesive protein, and as a result, it shows various pharmacological activities.

For example, fibrinogen being present in plasma interacts with a platelet membrane glycoprotein complex IIb/IIIa via RGD to cause a platelet aggregation, and it is considered that a synthetic peptide having RGD inhibits the interaction between fibrinogen and a platelet membrane glycoprotein complex IIb/IIIa and hence, it is useful as a platelet aggregation inhibitor [Phillips, D. R., Cell, 65, 359 (1991)]. Besides, it is also known that a peptide having a RGD derived from snake venom effectively inhibits bone resorption by osteoclast [Sato, M., et al., J. Cell Biol., 111, 1713 (1990)].

Besides, fibronectin is considered to participate in differentiation and growth of cells [Yamada, K. M., et al., Ann. Rev. Biochem., 52, 761 (1983)], but since it stimulates migration of fibroblast and macrophage, it is expected to be applied to the treatment of wound or the regulation of immune mechanism. Particularly, fibronectin has been tried in the local treatment of corneal disorders by utilizing the promotion effect thereof on wound healing [Fujikawa, L. S., et al., Lab. Invest., 45, 120 (1981)].

Moreover, cell adhesive proteins have been drawing attention as a substance participating in cancer metastasis. A cancer cell forms a multicellular mass in the presence of fibronectin or laminin so that it can more easily grow or survive. In fact, it has been confirmed that an RGD sequence, which is an adhesive core of fibronectin, inhibits the metastasis of cancer cell [Humphries, M. J. et al., Science, 233, 467 (1986)].

Thus, since cell adhesive proteins show various biological activities, a medicament which can selectively interact with a receptor of these proteins can be expected to be useful in the prophylaxis or treatment of various diseases.

On the other hand, a lot of screening on non-peptide compounds interacting with a receptor of these proteins has been as reported, for example, in EP 512831, EP 540334, WO 94/8962, WO 94/12181, EP 445796, etc. However, there is no compound which can clinically be used.

Under these circumstances, it has been desired to develop a platelet aggregation inhibitor, a cancer metastasis inhibitor, a wound healing agent or a bone resorption inhibitor, which selectively interacts with a receptor of a cell adhesive protein such as fibrinogen, fibronectin, etc., and shows excellent absorbability and excellent stability in living body.

DISCLOSURE OF INVENTION

The present inventors have intensively studied and have found a novel 2,3-diaminopropionic acid derivative which can selectively interact with a receptor of a cell adhesive protein, such as fibrinogen, fibronectin, etc.

That is, the gist of the present invention is as follows.

[1] A compound of the formula (1):

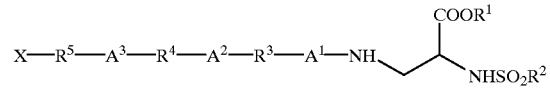

wherein $R^1$ is a hydrogen atom, a lower alkyl group, a cycloalkyl group, a lower alkenyl group, a lower alkynyl group, an aryl group, a heterocyclic group, a substituted lower alkyl group, a substituted cycloalkyl group, a substituted lower alkenyl group, a substituted lower alkynyl group, a substituted aryl group or a substituted heterocyclic group;

$R^2$ is a lower alkyl group, a cycloalkyl group, a lower alkenyl group, a lower alkynyl group, an aryl group, a heterocyclic group, a substituted lower alkyl group, a substituted cycloalkyl group, a substituted lower alkenyl group, a substituted lower alkynyl group, a substituted aryl group or a substituted heterocyclic group;

$A^1$ is —CO— or —CO—$A^4$— (wherein $A^4$ is a residue of an (α-amino acid, an α-amino acid derivative, a β-amino acid or a β-amino acid derivative, or a residue of a peptide consisting of 2 or 3 residues thereof);

$A^2$ and $A^3$ are the same or different and each a single bond, —$NR^6$— (wherein $R^6$ is a hydrogen atom or a lower alkyl group), an oxygen atom, $S(O)_n$ (wherein n is 0, 1 or 2), —CO—$NR^7$— (wherein $R^7$ is a hydrogen atom or a lower alkyl group), —$NR^7$—CO— (wherein $R^7$ is the same as defined above), —CO—$A^5$—$NR^8$— (wherein $R^8$ is a hydrogen atom or a lower alkyl group, $A^5$ is a residue of an α-amino acid, an α-amino acid derivative, a β-amino acid or a β-amino acid derivative, or a reside of a dipeptide consisting of 2 residues thereof), —$NR^8$—$A^5$—CO— (wherein $R^8$ and $A^5$ are the same as defined above), a divalent group of a monocyclic hydrocarbons or a divalent group of a monocyclic heterocyclic group;

$R^3$, $R^4$ and $R^5$ are the same or different and each a single bond, or an alkylene, alkenylene or alkynylene group, which may optionally be substituted by 1 to 4 groups selected from a hydroxy group, an oxo group, a halogen atom, an aryl group and a cycloalkyl group, provided that when $A^2$ and $A^3$ are the same or different and each —$NR^6$— (wherein $R^6$ is the same as defined above), an oxygen atom or $S(O)_n$ (wherein n is the same as defined above), $R^4$ should not be a single bond;

The definition for X and the number of atoms comprising a divalent main chain represented by —$R^5$—$A^3$—$R^4$—$A^2$—$R^3$—$A^1$— are shown in the following (a) or (b):

(a) X is a group of the formula (2):

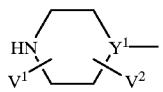

wherein $Y^1$ is a methine group or a nitrogen atom, $V^1$ and $V^2$ are the same or different and each a hydrogen atom or a lower alkyl group, provided that both $V^1$ and $V^2$ are the substituent on the carbon atom, and the number of atoms comprising a divalent main chain represented by —$R^5$—$A^3$—$R^4$—$A^2$—$R^3$—$A^1$— is 6 to 11.

(b) X is a group of the formula (3):

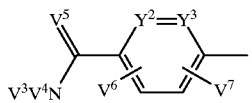

wherein $Y^2$ and $Y^3$ are the same or different and each a methine group or a nitrogen atom, $V^3$ and $V^4$ are the same or different and each a hydrogen atom, an alkyl group, a substituted lower alkyl group, a cycloalkyl group, an amino group, an acylamino group, a lower alkyloxycarbonyl group or a lower alkyloxycarbonyl group substituted by an aryl group, $V^5$ is an imino group or an oxygen atom, $V^6$ and $V^7$ are a hydrogen atom or a lower alkyl group, provided that both $V^6$ and $V^7$ are a substituent on the carbon atom, or a group of the formula (4):

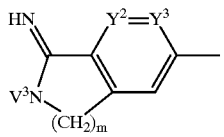

wherein $Y^2$, $Y^3$ and $V^3$ are the same as defined above, m is 2 or 3, and the number of atoms comprising a divalent main chain represented by —$R^5$—$A^3$—$R^4$—$A^2$—$R^3$—$A^1$— is 4 to 9, or a pharmaceutically acceptable salt thereof.

[2] The compound according to [1], wherein $R^2$ is an aryl group, a substituted aryl group, an aromatic heterocyclic group or a substituted aromatic heterocyclic group, or a pharmaceutically acceptable salt thereof.

[3] The compound according to [1], wherein $R^2$ is an aryl group, an aromatic heterocyclic group, or an aryl group substituted by 1 or more groups selected from a lower alkyl group, a lower alkyl group substituted by a halogen atom, a lower alkyloxy group, a lower alkyloxy group substituted by a halogen atom, an amino group, a dialkylamino group, an acylamino group, a halogen atom, a nitro group and a carboxyl group, or a pharmaceutically acceptable salt thereof.

[4] The compound according to any one of [1] to [3], wherein $A^1$ is —CO—, $R^3$ is —$CH_2$—$CHR^9$— (wherein $R^9$ is a hydrogen atom or a lower alkyl group), or a pharmaceutically acceptable salt thereof.

[5] The compound according to any one of [1] to [4], wherein the definition for X and the number of atoms comprising a divalent main chain represented by —$R^5$—$A^3$—$R^4$—$A^2$—$R^3$—$A^1$— are defined by the following (a) or (b), or a pharmaceutically acceptable salt thereof:

(a) X is a group of the formula (2):

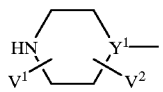

wherein $Y^1$, $V^1$ and $V^2$ are the same as defined above), and the number of atoms comprising a divalent main chain represented by —$R^5$—$A^3$—$R^4$—$A^2$—$R^3$—$A^1$— is 7 or 8;

(b) X is a group of the formula (3):

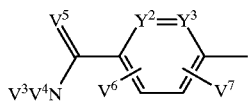

wherein $Y^2$, $Y^3$, $V^3$, $V^4$, $V^5$, $V^6$ and V7 are the same as defined above, or a group of the formula (4):

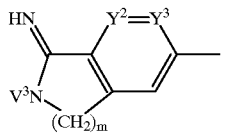

wherein $Y^2$, $Y^3$, $V^3$ and m are the same as defined above, and the number of atoms comprising a divalent main chain represented by —$R^5$—$A^3$—$R^4$—$A^1$—$R^3$—$A^1$— is 5 or 6.

[6] The compound according to any one of [1] to [5], which is a compound of the formula (5):

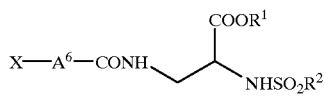

wherein $R^1$ and $R^2$ are the same as defined above, X and $A^6$ are defined by the following (a) or (b), or a pharmaceutically acceptable salt thereof:

(a) X is a group of the formula (2):

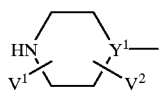

wherein $Y^1$, $V^1$ and $V^2$ are the same as defined above, $A^6$ is a divalent group selected from the following groups:
—$Y^4$—$(CH_2)_a$—$CONR^{10}$—$CH_2$—$CHR^9$— ($R^9$ is the same as defined above, $R^{10}$ is a hydrogen atom or a lower alkyl group, a is 1 or 2, $Y^4$ is a methylene group or an oxygen atom);
—$Y^4$—$(CH_2)_b$— ($Y^4$ is the same as defined above, and b is 5 or 6);
—$(CH_2)_c$—$CO$—$(CH_2)_d$— (c is 2 or 3, d is 3 or 4);
—$(CH_2)_c$—$CH(OH)$—$(CH_2)_d$— (c and d are the same as defined above);
—$CH_2$—$NR^{10}CO$—$(CH_2)_d$— ($R^{10}$ and d are the same as defined above);
—$Y^4$—$(CH_2)_e$—$Y^5$— ($Y^4$ is the same as defined above, $Y^5$ is an oxygen atom or —$NR^{11}$— ($R^{11}$ is a hydrogen atom or a lower alkyl group), and e is 4 to 6);

a group of the formula:

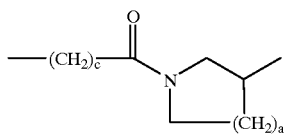

wherein a and c are the same as defined above, (b) X is a group of the formula (3):

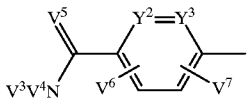

wherein $Y^2$, $Y^3$, $V^3$, $V^4$, $V^5$, $V^6$ and $V^7$ are the same as defined above, or a group of the formula (4):

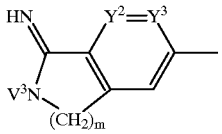

wherein $Y^2$, $Y^3$, $V^3$ and m are the same as defined above, $A^6$ is a divalent group selected from the following groups:

—$(CH_2)_f$—$CONR^{10}$—$CH_2$—$CHR^9$— ($R^9$ and $R^{10}$ are the same as defined above, and f is 0 or 1);

—$Y^4$—$(CH_2)_d$— ($Y^4$ and d are the same as defined above);

—$(CH_2)_f$CO—$(CH_2)_d$— (f and d are the same as defined above);

—$(CH_2)_f$—CH(OH)—$(CH_2)_d$— (f and d are the same as defined above);

—$NR^{10}CO$—$(CH_2)_d$— ($R^{10}$ and d are the same as defined above);

—$Y^4$—$(CH_2)_g$—$Y^5$— ($Y^4$ and $Y^5$ are the same as defined above, and g is 2 to 4);

a group of the formula:

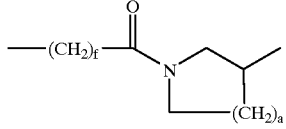

wherein a and f are the same as defined above;

a group of the formula:

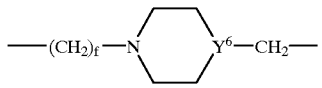

wherein f is the same as defined above, $Y^6$ is a methine group or a nitrogen atom;

a group of the formula:

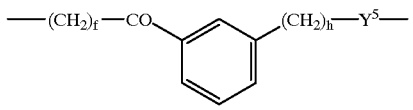

wherein $Y^5$ and f are the same as defined above, and h is 0 or 1;

a group of the formula:

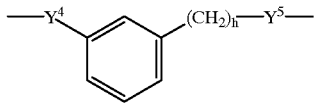

wherein $Y^4$, $Y^5$ and h are the same as defined above.

[7] The compound according to [6], where X and $A^6$ are defined by the following (a) or (b), or a pharmaceutically acceptable salt thereof.

(a) X is a group of the formula (2):

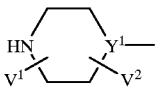

wherein $Y^1$, $V^1$ and $V^2$ are the same as defined above, and $A^6$ is a divalent group selected from the following groups:

—$Y^4$—$(CH_2)_a$—$CONR^{10}$—$CH_2$—$CHR^9$— ($R^9$, $R^{10}$, a and $Y^4$ are the same as defined above);

—$CH_2$—$NR^{10}CO$—$(CH_2)_d$— ($R^{10}$ and d are the same as defined above)

a group of the formula:

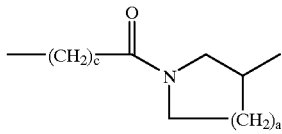

wherein a and c are the same as defined above.

(b) X is a group of the formula (3):

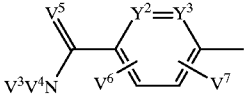

wherein $Y^2$, $Y^3$, $V^3$, $V^4$, $V^5$, $V^6$ and $V^7$ are the same as defined above, or a group of the formula (4):

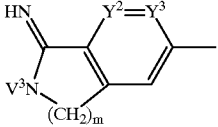

wherein $Y^2$, $Y^3$, $V^3$ and m are the same as defined above, $A^6$ is a divalent group selected from the following groups:

—$(CH_2)_f$—$CONR^{10}$—$CH_2$—$CHR^9$— ($R^9$, $R^{10}$ and f are the same as defined above);

—Y⁴—(CH₂)_d— (Y⁴ and d are the same as defined above);
—(CH₂)_f—CO—(CH₂)_d— (f and d are the same as defined above);
a group of the formula:

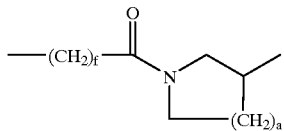

wherein a and f are the same as defined above;
a group of the formula:

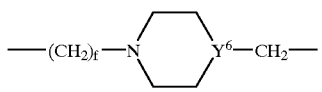

wherein f and Y⁶ are the same as defined above.
[8] The compound according to any one of [1] to [7], wherein X is a group of the formula (3):

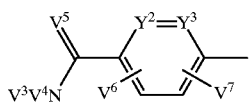

wherein Y², Y³, V³, V⁴, V⁵, V⁶ and V⁷ are the same as defined above, or a group of the formula (4):

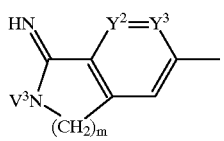

wherein Y², Y³, V³ and m are the same as defined above, A² and A³ are the same or different and each a single bond, —NR⁶— (R⁶ is the same as defined above), an oxygen atom, S(O)_n (n is the same as defined above), —CO—NR⁷— (R⁷ is the same as defined above), —NR⁷—CO— (R⁷ is the same as defined above), —CO—A⁵—NR⁸— (A⁵ and R⁸ are the same as defined above), —NR⁸—A⁵—CO— (R⁸ and A⁵ are the same as defined above), a divalent group of aliphatic monocyclic hydrocarbons or a divalent group of aliphatic monocyclic heterocyclic group, or a pharmaceutically acceptable salt thereof.
[9] The compound according to any one of [1] to [8], wherein X is a group of the formula (6):

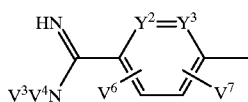

wherein Y², Y³, V³, V⁴, V⁶ and V⁷ are the same as defined above, or a pharmaceutically acceptable salt thereof.
[10] The compound according to [9], wherein Y² and Y³ are a methine group, and V⁶ and V⁷ are a hydrogen atom, or a pharmaceutically acceptable salt thereof.
[11] The compound according to [6], wherein X is a 4-amidinophenyl group, and A⁶ is —CO—NH—CH₂— CH₂— or —O—(CH₂)₃-, or a pharmaceutically acceptable salt thereof.
[12] The compound according to any one of [1] to [11], wherein the stereo-configuration of the 2-position thereof is S-configuration, or a pharmaceutically acceptable salt thereof.
[13] A platelet aggregation inhibitor which contains the compound as set forth in any one of [1 ] to [12], or a pharmaceutically acceptable salt thereof.
[14] A cancer metastasis inhibitor which contains the compound as set forth in any one of [1 ] to [12], or a pharmaceutically acceptable salt thereof.
[15] A wound healing agent which contains the compound as set forth in any one of [1] to [12], or a pharmaceutically acceptable salt thereof.
[16] A bone resorption inhibitor which contains the compound as set forth in any one of [1] to [12], or a pharmaceutically acceptable salt thereof.

The lower alkyl group includes a straight chain or branched chain alkyl group having 1 to 6 carbon atoms, for example, methyl, ethyl, propyl, 1-methylethyl, butyl, 1-methylpropyl, 2-methylpropyl, 1,1-dimethylethyl, pentyl, 1-methylbutyl, 1-ethylpropyl, hexyl, 1-methylpentyl, 1-ethylbutyl, 2-methylpentyl, etc.

The alkyl group includes a straight chain or branched chain alkyl group having 1 to 16 carbon atoms, for example, methyl, ethyl, propyl, 1-methylethyl, butyl, 1-methylpropyl, 2-methylpropyl, 1,1-dimethylethyl, pentyl, 1-methylbutyl, 1-ethylpropyl, hexyl, 1-methylpentyl, 1-ethylbutyl, 2-methylpentyl, octyl, decyl, 3-methylnonyl, 2,5-diethylheptyl, dodecyl, tetradecyl, pentadecyl, hexadecyl, etc.

The lower alkenyl group includes a straight chain or branched chain alkenyl group having 2 to 6 carbon atoms, and having 1 to 3 double bonds, for example, vinyl, 1-propenyl, 2-propenyl, 1-methylvinyl, 1-butenyl, 2-butenyl, 1-pentenyl, 1-hexenyl, etc.

The lower alkynyl group includes a straight chain or branched chain alkynyl group having 2 to 6 carbon atoms, and having 1 to 3 triple bonds, for example, ethynyl, 1-propynyl, 2-propynyl, 1-butynyl, 1-pentynyl, 1-hexynyl, etc.

The cycloalkyl group includes a cycloalkyl group having 5 to 7 carbon atoms, for example, cyclopentyl, cyclohexyl, cyclopentyl, etc.

The aryl group includes an aryl group having 6 to 14 carbon atoms, for example, phenyl, 1-naphthyl, 2-naphthyl, 1-anthranyl, 2-anthranyl, 9-fluorenyl, etc.

The heterocyclic group includes a saturated or unsaturated heterocyclic group selected from a 5 to 7-membered monocyclic group, a 9- to 10-membered bicyclic group, and a 12- to 14-membered tricyclic group, said heterocyclic group contains 1 to 4 heteroatoms selected from oxygen atom, nitrogen atom, sulfur atom, and the nitrogen atom or sulfur atom thereof may optionally be oxidized, and the binding position thereof is at a nitrogen atom or a carbon atom. Besides, the carbon atom forming the ring may be optionally substituted by an oxo group. Suitable examples thereof are a 6-membered saturated monocyclic heterocyclic group having 1 or 2 heteroatoms selected from oxygen atom, nitrogen atom and sulfur atom, such as piperidyl, piperazinyl, morpholinyl, a 6-membered unsaturated monocyclic heterocyclic group having 1 or 2 heteroatoms selected from oxygen atom, nitrogen atom and sulfur atom, such as pyridyl, pyridazinyl, pyrazinyl, etc., a 5-membered saturated monocyclic heterocyclic group containing 1 to 2 heteroatoms selected from oxygen atom, nitrogen atom and sulfur atom, such as oxolanyl, pyrrolidinyl, etc., a 5-membered unsaturated monocyclic heterocyclic group having 1 to 3 heteroatoms selected from oxygen atom, nitrogen atom and sulfur atom, for example, imidazolyl, furyl, 2-oxo-1,3-dioxolenyl, pyrrolyl, 5-oxo-2-tetrahydrofuranyl, etc., a 9- to 10-membered unsaturated bicyclic heterocyclic group having 1 to 3 heteroatoms selected from oxygen atom, nitrogen atom and sulfur atom, such as quinolyl, isoquinolyl, indolyl, 1,3-dihydro-3-oxo-1-isobenzofuranyl, etc., a 12- to 14-membered unsaturated tricyclic heterocyclic group having 1 to 3 heteroatoms selected from oxygen atom, nitrogen atom and sulfur atom, such as anthraquinolyl, etc. The aromatic heterocyclic group includes a heterocyclic group which is an aromatic group.

The substituted lower alkyl group includes a lower alkyl group substituted by 1 to 5 groups selected from the group consisting of a cycloalkyl group, a substituted cycloalkyl group, an aryl group, a substituted aryl group, a heterocyclic group, a substituted heterocyclic group, a halogen atom, —$OP^1$ ($P^1$ is a hydrogen atom, a lower alkyl group, a cycloalkyl group, an aryl group, or a modifying group for hydroxy group), —$OCOP^2$ ($P^2$ is a hydrogen atom, a lower alkyl group, a cycloalkyl group, an aryl group or a heterocyclic group), —$NP^3P^4$ ($P^3$ is a hydrogen atom or a lower alkyl group, $P^4$ is a hydrogen atom, a lower alkyl group, a cycloalkyl group, an aryl group, a heterocyclic group or a modifying group for amino group), —$C(=NP^5)NP^6P^7$ ($P^5$, $P^6$ and $P^7$ are the same or different, and each a hydrogen atom, a lower alkyl group, a cycloalkyl group, a modifying group for amidino group), —$NHC(=NP^5)NP^6P^7$ ($P^5$, $P^6$ and $P^7$ are the same as defined above), a nitro group, a cyano group, —$COOP^8$ ($P^8$ is a hydrogen atom, a lower alkyl group, a cycloalkyl group, an aryl group, a heterocyclic group or a modifying group for carboxyl group), —$CONP^9P^{10}$ ($P^9$ is a hydrogen atom or a lower alkyl group, $P^{10}$ is a hydrogen atom, a lower alkyl group or a modifying group for amido group), —$SP^{11}$ ($P^{11}$ is a hydrogen atom, a lower alkyl group, a cycloalkyl group, an aryl group, a heterocyclic group or a modifying group for thiol group), —$COP^{12}$ ($P^{12}$ is a hydrogen atom, a lower alkyl group, a cycloalkyl group, an aryl group or a heterocyclic group), —$NHCOP^{13}$ ($P^{13}$ is a hydrogen atom, a lower alkyl group, a cycloalkyl group or an aryl group), —$S(O)_iP^{14}$ ($P^{14}$ is a lower alkyl group, a cycloalkyl group or an aryl group, and i is 1 or 2), —$SO_2NP^{15}P^{16}$ ($P^{15}$ and $P^{16}$ are the same or different and each a hydrogen atom, a lower alkyl group, a cycloalkyl group or an aryl group) and —$OCOOP^{17}$ ($P^{17}$ is a lower alkyl group, a cycloalkyl group, an aryl group or a heterocyclic group). Suitable examples are benzyl, 2-phenylethyl, 3-phenylpropyl, 4-phenylbutyl, 5-phenylpentyl, 6-phenylhexyl, indolylmethyl, 2-(3-indolyl)ethyl, bromomethyl, pivaloyloxymethyl, 1-ethoxycarbonyloxyethyl, 5-methyl-2-oxo-1,3-dioxolen-4-ylmethyl, 2-chloroethyl, 2-dimethylaminoethyl, diethylaminoethyl, 3-dimethylamino-2-(dimethylaminomethyl)propyl, 2-(1-morpholinyl)ethyl, 1-acetoxyethyl, 1-methoxycarbonyloxyethyl, acetoxymethyl, 1-acetoxy-1-phenylmethyl, methoxycarbonylmethyl, 1-pivaloyloxyethyl, etc.

The substituted lower alkenyl group includes a lower alkenyl group substituted by 1 to 5 groups selected from the group consisting of a cycloalkyl group, an aryl group, a heterocyclic group, a halogen atom, —$OP^{18}$ ($P^{18}$ is a hydrogen atom, a lower alkyl group or a modifying group for hydroxy group), —$OCOP^{19}$ ($P^{19}$ is a hydrogen atom or a lower alkyl group), a nitro group, a cyano group, —$COOP^{20}$ ($P^{19}$ is a hydrogen atom or a modifying group for carboxyl group), —$CONP^9P^{10}$ ($P^9$ and $P^{10}$ are the same as defined above), —$COP^{21}$ ($P^{21}$ is a hydrogen atom or a lower alkyl group) and —$OCOOP^{22}$ ($P^{22}$ is a lower alkyl group). Suitable examples are 3-phenyl-2-propenyl, 5-methoxy-2-pentenyl, 2-carboxylvinyl, etc.

The substituted lower alkynyl group includes a lower alkynyl group substituted by 1 to 5 groups selected from the group consisting of a cycloalkyl group, an aryl group, a heterocyclic group, a halogen atom, —$OP^{18}$ ($P^{18}$ is the same as defined above), —$OCOP^{19}$ ($P^{19}$ is the same as defined above), a nitro group, a cyano group, —$COOP^{20}$ ($P^{20}$ is the same as defined above), —$CONP^9P^{10}$ ($P^9$ and $P^{10}$ are the same as defined above), —$COP^{21}$ ($P^{21}$ is the same as defined above) and —$OCOOP^{22}$ ($P^{22}$ is the same as defined above). Suitable example is 3-phenyl-2-propynyl group.

The substituted cycloalkyl group includes a cycloalkyl group substituted by 1 to 3 groups selected from the group consisting of a lower alkyl group, an aryl group, a heterocyclic group, a halogen atom, —$OP^{18}$ ($P^{18}$ is the same as defined above), —$OCOP^{19}$ ($P^{19}$ is the same as defined above), —$NP^{23}P^{24}$ ($P^{23}$ is a hydrogen atom or a lower alkyl group, $P^{24}$ is a hydrogen atom, a lower alkyl group or a modifying group for amino group), —$C(=NP^{25})NP^{26}P^{27}$ ($P^{25}$, $P^{26}$ and $P^{27}$ are the same or different and each a hydrogen atom or a modifying group for amidino group), —$NHC(=NP^{25})NP^{26}P^{27}$ ($P^{25}$, $P^{26}$ and $P^{27}$ are the same as defined above), a nitro group, a cyano group, —$COOP^{20}$ ($P^{20}$ is the same as defined above), —$CONP^9P^{10}$ ($P^9$ and $P^{10}$ the same as defined above), —$SP^{28}$ ($P^{28}$ is a hydrogen tom, a lower alkyl group or a modifying group for thiol group), —$COP^{21}$ ($P^{21}$ is the same as defined above), —$NHCOP^{29}$ ($P^{29}$ is a hydrogen atom or a lower alkyl group), —$S(O)_iP^{30}$ ($P^{30}$ is a lower alkyl group, and i is the same as defined above), —$SO_2NP^{31}P^{32}$ ($P^{31}$ and $P^{32}$ are the same or different and each a hydrogen atom or a lower alkyl group) and —$OCOOP^{22}$ ($P^{22}$ is the same as defined above). Suitable examples are 4-chlorocyclohexyl, 4-cyanocyclohexyl, 2-dimethylaminocyclohexyl, 4-methoxycyclohexyl, etc.

The substituted heterocyclic group includes a heterocyclic group substituted by 1 to 3 groups selected from the group consisting of a lower alkyl group, a cycloalkyl group, an aryl group, a heterocyclic group, a halogen atom, —$OP^{18}$ ($P^{18}$ is the same as defined above), —$OCOP^{19}$ ($P^{19}$ is the same as defined above), —$NP^{23}P^{24}$ ($P^{23}$ and $P^{24}$ are the same as defined above), —$C(=NP^{25})NP^{26}P^{27}$ ($P^{25}$, $P^{26}$ and $P^{27}$ are the same as defined above), —$NHC(=NP^{25})NP^{26}P^{27}$ ($P^{25}$, $P^{26}$ and $P^{27}$ are the same as defined above), a nitro group, a cyano group, —$OCOOP^{22}$ ($P^{22}$ is the same as defined above), —$CONP^9P^{10}$ ($P^9$ and $P^{10}$ are the same as defined above), —$SP^{28}$ ($P^{28}$ is the same as defined above), —$COP^{21}$ ($P^{21}$ is the same as defined above), —$NHCOP^{29}$ ($P^{29}$ is the same as defined above), —$S(O)_iP^{30}$ ($P^{30}$ and i are the same as defined above), —$SO_2NP^{31}P^{32}$ ($P^{31}$ and $P^{32}$ are the same as defined above) and —$OCOOP^{22}$ ($P^{22}$ is the same as defined above). Suitable examples are 1-acetyl-4-piperidinyl, 1-benzyl-4-imidazolyl, 1-methyl-3-indolyl, 5-methyl-2-oxo-1,3-dioxolen-4-yl, etc.

The substituted aryl group includes an aryl group substituted by 1 to 5 groups selected from the group consisting of a lower alkyl group, a lower alkenyl group, a lower alkynyl group, a cycloalkyl group, an aryl group, a heterocyclic group, a substituted alkenyl group, a substituted alkynyl group, a substituted cycloalkyl group, a substituted heterocyclic group, a halogen atom, —$OP^1$ ($P^1$ is the same as defined above), —$OCOP^2$ ($P^2$ is the same as defined above), —$NP^3P^4$ ($P^3$ and $P^4$ are the same as defined above), —$C(=NP^5)NP^6P^7$ ($P^5$, $P^6$ and $P^7$ are the same as defined above), —NHC(=NP⁵)NP⁶P⁷ (P⁵, P⁶ and P⁷ are the same as defined above), a nitro group, a cyano group, —COOP⁸ (P⁸ is the same as defined above), —CONP⁹P¹⁰ (P⁹ and P¹⁰ are the same as defined above), —SP¹¹ (P¹¹ is the same as defined above), —COP¹² (P¹² is the same as defined above), —NHCOP¹³ (P¹³ is the same as defined above), —S(O)ᵢO¹⁴ (i and P¹⁴ are the same as defined above), —SO₂NP¹⁵P¹⁶ (P¹⁵ and P¹⁶ are the same as defined above), —OCOOP¹⁷ (P¹⁷ is the same as defined above), a lower alkyl group substituted by —OP¹ (P¹ is the same as defined above) or —NP³P⁴ (P³ and P⁴ are the same as defined above), and a lower alkyl group substituted by 1 to 5 atoms selected from the group consisting of fluorine atom, chlorine atom and bromine atom. When two substituents of the substituted aryl group are located adjacently, these substituents may optionally combine together to form a 4- to 7-membered ring.

Suitable examples of the substituted aryl group are 4-fluorophenyl, 3-chlorophenyl, 4-chlorophenyl, 3-bromophenyl, 4-bromophenyl, 4-iodophenyl, 2,4-dichlorophenyl, 4-hydroxyphenyl, 3,4-dihydroxyphenyl, 4-methylphenyl, 4-methoxyphenyl, 3,4-dimethoxyphenyl, 3,4-methylenedioxyphenyl, 4-aminophenyl, 4-guanidinophenyl, 4-aminomethylphenyl, 4-cyanophenyl, 4-carboxyphenyl, 4-acetylphenyl, 4-chloro-1-naphthyl, 4-amidinophenyl, 4-nitrophenyl, 4-ethoxycarbonylphenyl, 4-acetoxyphenyl, 4-benzyloxyphenyl, 2-fluoro-4-hydroxyphenyl, 5-indanyl, 4-(2-carboxyvinyl)phenyl, 4-(2-butyl)phenyl, 3,5-dichloro-2-hydroxyphenyl, 2,3,4-trichlorophenyl, 2,4,5-trichlorophenyl, 2,4,6-tri-(2-propyl)phenyl, 2,5-dimethylphenyl, 2-nitrophenyl, 3-nitrophenyl, 2,4-dinitrophenyl, 4-chloro-3-nitrophenyl, 2,5-dimethoxyphenyl, 2,5-dimethylphenyl, 2-methoxycarbonylphenyl, 3-carboxyphenyl, 2-methoxy-5-carboxyphenyl, 4-t-butylphenyl, 4-ethylphenyl, 2-methylphenyl, 3-methylphenyl, 2,4,6-trimethylphenyl, 5-dimethylamino-1-naphthyl, 4-acetaminophenyl, 2,3,4,5,6-pentafluorophenyl, 2,3,4,5,6-pentamethylphenyl, 4-dimethylamino-3-nitrophenyl, 2,3,5,6-tetramethylphenyl, 2,5-dichlorophenyl, 4-trifluoromethylphenyl, 2-trifluoromethylphenyl, 3-trifluoromethylphenyl, 3,5-ditrifluoromethylphenyl, etc.

The acyl group includes a straight chain or branched chain alkanoyl group having 1 to 6 carbon atoms, a cycloalkylcarbonyl group having 6 to 8 carbon atoms, a benzoyl group, a lower alkylsulfonyl group, an arylsulfonyl group, etc., and suitable examples are an alkanoyl group such as acetyl, propionyl, butyryl, isobutyryl, valeryl, isovaleryl, pivaloyl, hexanoyl, t-butylacetyl, etc., a cycloalkylcarbonyl group such as cyclopentylcarbonyl, cyclohexylcarbonyl, cycloheptylcarbonyl, etc., a lower alkylsulfonyl group such as methylsulfonyl, ethylsulfonyl, propylsulfonyl, butylsulfonyl, etc., and an arylsulfonyl group such as benzenesulfonyl, naphthalenesulfonyl, etc.

The halogen atom is fluorine atom, chlorine atom, bromine atom, iodine atom, etc.

The residue of an α-amino acid or α-amino acid derivative includes a group of the formula (7):

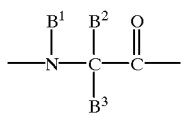

wherein B¹ and B² are the same or different and each a hydrogen atom or a lower alkyl group, B³ is a hydrogen atom, a lower alkyl group, —CHE¹OE² (E¹ is a hydrogen atom or a methyl group, E² is a hydrogen atom, a lower alkyl group or a modifying group for hydroxy group), —CH₂CH₂OE² (E² is the same as defined above), —CE¹₂SE³ (E¹ is the same as defined above, E³ is a hydrogen atom, a lower alkyl group or a modifying group for thiol group), —CH₂CH₂S(O)ⱼCH₃ (j is 0 is 0, 1 or 2), —(CH₂)ₖCOOE⁴ (k is 1 or 2, E⁴ is a hydrogen atom or a modifying group for carboxyl group), —(CH₂)ₖCONE⁵E⁶ (k is the same as defined above, E⁵ is a hydrogen atom or a lower alkyl group, E⁶ is a hydrogen atom, a lower alkyl group or a modifying group for amido group), —(CH₂)ₚNE⁷E⁸ (p is 3 or 4, E⁷ is a hydrogen atom or a lower alkyl group, E⁸ is a hydrogen atom, a lower alkyl group or a modifying group for amino group), —(CH₂)ₚNHC(=NE⁹)NE¹⁰E¹¹ (p is the same as defined above, E⁹, E¹⁰ and E¹¹ are the same or different and each a hydrogen atom or a modifying group for guanidino group), or —(CH₂)qE¹² (q is 0, 1 or 2, E¹² is a halogen atom, a cycloalkyl group, an aryl group, a substituted aryl group, a group of the formula (8):

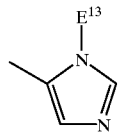

wherein E¹³ is a hydrogen atom, a lower alkyl group or a modifying group for imidazolyl group, or a group of the formula (9):

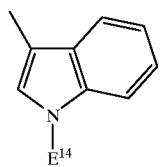

wherein E¹⁴ is a hydrogen atom, a lower alkyl group or a modifying group for indolyl group), provided that B¹ and B³ may combine together to form ethylene, trimethylene or tetramethylene, or B² and B³ may combine together to form pentamethylene.

When an asymmetric carbon atom exists in the residue of an α-amino acid or α-amino acid derivative, any isomer, or a mixture thereof is also included therein.

Suitable examples for B¹, B² and B³ in the formula (7) are explained below. Suitable examples for B¹ are hydrogen atom, methyl, ethyl, etc. Suitable examples for B² are hydrogen atom, methyl, etc. Suitable examples for B³ are a hydrogen atom, a lower alkyl group such as methyl, 1-methylethyl, 1-methylpropyl, 2-methylpropyl, 1-butyl, etc., benzyl, 4-methoxybenzyl, 4-benzyloxybenzyl, methoxymethyl, benzyloxymethyl, etc.

The residue of a β-amino acid or a β-amino acid derivative includes a group of the formula (10):

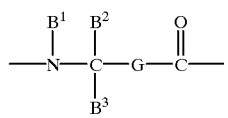

wherein B¹, B² and B³ are the same as defined above, G is —CH(OH)—, —CH₂— or —CO—.

When an asymmetric carbon atom exists in the residue of a β-amino acid or a β-amino acid derivative, any isomer, or a mixture thereof is also included therein.

Suitable examples for $B^1$, $B^2$ and $B^3$ in the formula (10) are explained below. Suitable examples for $B^1$ are a hydrogen atom, methyl, ethyl, etc. Suitable examples for $B^2$ are a hydrogen atom, methyl, etc. Suitable examples for $B^3$ are a hydrogen atom, a lower alkyl group such as methyl, 1-methylethyl, 1-methylpropyl, 2-methylpropyl, 1-butyl, etc., benzyl, 4-methoxybenzyl, 4-benzyloxybenzyl, methoxymethyl, benzyloxymethyl, etc.

The divalent group of monocyclic hydrocarbons includes a divalent group of a saturated or unsaturated, 5- to 7-membered monocyclic hydrocarbons. The monocyclic hydrocarbons may optionally be substituted by 1 to 2 groups selected from a lower alkyl group, a substituted lower alkyl group and an aryl group. The binding position of the monocyclic hydrocarbons is preferably 1,3-positions or 1,4-positions in case of 6- or 7-membered monocyclic hydrocarbons, or 1,3-positions in case of 5-membered monocyclic hydrocarbons. The divalent group of the saturated, 5- to 7-membered monocyclic hydrocarbons is, for example, 1,3-cyclopentylene, 1,4-cyclohexylene, 1,4-cycloheptylene, etc. The divalent group of the unsaturated, 5- to 7-membered monocyclic hydrocarbons is, for example, 1,3-phenylene, 3-cyclohexen-1,4-ylene, 2-cyclohepten-1,5-ylene, etc. The divalent group of the aliphatic monocyclic hydrocarbons means the divalent groups of the monocyclic hydrocarbons except for aromatic ones.

The divalent group of the monocyclic heterocyclic group includes divalent groups of a saturated or unsaturated, 5- to 7-membered monocyclic heterocyclic group having 1 to 4 heteroatoms selected from oxygen atom, nitrogen atom and sulfur atom, wherein one or two carbon atoms thereof may optionally be substituted by an oxo group. Further, one or two carbon atoms or nitrogen atoms thereof may optionally be substituted by a lower alkyl group, a substituted lower alkyl group or an aryl group. The binding positions of the monocyclic heterocyclic group may be 1,3-positions or 1,4-positions in case of 6- or 7-membered monocyclic heterocyclic group, or 1,3-positions in case of 5-membered monocyclic heterocyclic group. The nitrogen atom or sulfur atom thereof may optionally be oxidized. The monocyclic heterocyclic group binds at a carbon atom or nitrogen atom thereof. Suitable examples of the divalent groups of the saturated heterocyclic group are 1,3-pyrrolidinediyl, 1,4-piperazinediyl, 1,4-piperidinediyl, etc. Suitable example of the divalent groups of the unsaturated heterocyclic group are 2,5-pyridinediyl, 2,4-thiophenediyl, 2,5-pyridazinyldiyl, etc. The divalent group of the aliphatic monocyclic heterocyclic group means the divalent groups of the monocyclic heterocyclic group except for aromatic ones.

The alkylene group includes a straight chain or branched chain alkylene group having 1 to 15 carbon atoms, preferably ones having 1 to 10 carbon atoms, for example, methylene, ethylene, trimethylene, tetramethylene, 3-methyltetramethylene, pentamethylene, hexamethylene, octamethylene, decamethylene, 3-methylhexamethylene, 2-methyltrimethylene, etc.

The alkenylene group includes a straight chain or branched chain alkenylene group having 2 to 15 carbon atoms, preferably ones having 2 to 7 carbon atoms, for example, vinylene, propenylene, 2-pentenylene, 2-heptenylene, 3-methyl-3-hexenylene, 1-butenylene, 3-hexenylene, 2-hexenylene, etc.

The alkynylene group includes a straight chain or branched chain alkynylene group having 2 to 1 5 carbon atoms, preferably ones having 2 to 7 carbon atoms, for example, ethynylene, 2-pentynylene, 2-heptynylene, 2-(1-propynyl)pentamethylene, 2-butynylene, 1-butynylene, 3-hexynylene, 2-hexynylene, 1-hexynylene, 2-methyl-1-propynylene, 1-propynylene, 2-methyl-3-butynylene, etc.

When the compound of the formula (1) contains an asymmetric carbon atom, the present invention also includes any isomer or a mixture thereof. When the compound of the formula (1) contains two or more asymmetric carbon atoms, the present compounds exist in the form of an enantiomer, diastereomer, or a mixture thereof, for example, in the form of a racemic mixture thereof. The stereo-configuration of the asymmetric 2-carbon atom of 2,3-diaminopropionic acid is preferably S-configuration.

Suitable examples for $R^1$ of the formula (1) are a hydrogen atom, a lower alkyl group such as methyl, ethyl, propyl, etc., cyclohexyl, benzyl, a lower alkyl group substituted by —OCOP$^{33}$ (P$^{33}$ is a lower alkyl group, a cycloalkyl group, an aryl group, or a heterocyclic group) such as acetoxymethyl, 1-acetoxyethyl, 1-acetoxy-1-phenylmethyl, pivaloyloxymethyl, 1-pivaloyloxyethyl, etc., a lower alkyl group substituted by —OCOOP$^{34}$ (P$^{34}$ is a lower alkyl group, a cycloalkyl group, an aryl group or a heterocyclic group) such as 1-methoxycarbonyloxyethyl, 1-ethoxycarbonyloxyethyl, etc., a lower alkyl group substituted by a substituted heterocyclic group such as 5-methyl-2-oxo-1,3-dioxolen-4-ylmethyl, 2-(1-morpholinyl)ethyl, etc., a heterocyclic group such as 5-oxo-2-tetrahydrofuranyl, 1,3-dihydro-3-oxo-1-isobenzofuranyl, a substituted aryl group such as 5-indanyl, etc., 3-dimethylamino-2-(dimethylaminomethyl)propyl, 2-dimethylaminoethyl, 2-diethylaminoethyl, methoxycarbonylmethyl, 2-dimethylaminocyclohexyl, etc.

Suitable examples for $R^2$ in the formula (1) are a lower alkyl group, a substituted lower alkyl group, a cycloalkyl group, a substituted cycloalkyl group, an aryl group, a substituted aryl group, a heterocyclic group, a substituted heterocyclic group, etc., preferably an aryl group, a substituted aryl group, an aromatic heterocyclic group, a substituted aromatic heterocyclic group, etc., for example, a lower alkyl group such as methyl, ethyl, propyl, butyl, etc., a substituted lower alkyl group such as 2-chloroethyl, benzyl, etc., a cycloalkyl group such as cyclohexyl, etc., an aryl group such as phenyl, 1-naphthyl, 2-naphthyl, 1-anthranyl, etc., a substituted aryl group such as 8-quinolyl, 1-anthraquinolyl, 4-(2-carboxylvinyl)phenyl, 4-(2-butyl)phenyl, 3,5-dichloro-2-hydroxyphenyl, 2,3,4-trichlorophenyl, 2,4,5-trichlorophenyl, 2,4,6-tri-(2-propyl)phenyl, 2,5-dimethylphenyl, 2-nitrophenyl, 3-nitrophenyl, 2,4-dinitrophenyl, 4-chloro-3-nitrophenyl, 2,5-dimethoxyphenyl, 2,5-dimethylphenyl, 2-methoxycarbonylphenyl, 3-carboxyphenyl, 2-methoxy-5-carboxyphenyl, 4-t-butylphenyl, 4-ethylphenyl, 2-methylphenyl, 3-methylphenyl, 2,4,6-trimethylphenyl, 5-dimethylamino-1-naphthyl, 4-acetaminophenyl, 2,3,4,5,6-pentafluorophenyl, 2,3,4,5,6-pentamethylphenyl, 3-nitro-4-dimethylaminophenyl, 2,3,5,6-tetramethylphenyl, 4-nitrophenyl, 4-bromophenyl, 4-iodophenyl, 4-chlorophenyl, 4-fluorophenyl, 4-carboxyphenyl, 4-methylphenyl, 4-methoxyphenyl, 4-trifluoromethylphenyl, 3-trifluoromethylphenyl, 2-trifluoromethylphenyl, 2,5-dichlorophenyl, 3,5-ditrifluoromethylphenyl, etc., a non-aromatic heterocyclic group such as 3-morphonyl, 2-piperidyl, etc., a substituted non-aromatic heterocyclic group such as 3-(2-methyl)morphonyl, 2-(5-methyl)piperidyl, etc., an aromatic heterocyclic group such as 2-thienyl, 3-pyridyl, 8-quinolyl, etc., a substituted aromatic heterocyclic group such as 2-(5-chloro)thienyl, 2-(5-bromo)thienyl, 2-(5-(2-pyridyl)thienyl), 3-(5-methyl)pyridyl, 2-(5-dichloromethyl)furyl, 3-(2- methoxycarbonyl)thienyl, 3-(2,5-dichloro)thienyl, 4-(3,5-dimethyl)isoxazolyl, 5-(2,4-dimethyl)thiazolyl, 4-(1-methyl)imidazolyl, etc.

The number of atoms comprising a divalent main chain represented by —$R^5$—$A^3$—$R^4$—$A^2$—$R^3$—$A^1$— means the number of atoms comprising the shortest straight chain which is composed of bindings through from one end to the other end of —$R^5$—$A^3$—$R^4$—$A^2$—$R^3$—$A^1$—. When the chain partially contains a cyclic structure, among the two chains composing said cycle, one having fewer atoms is considered to be a member of the above chain, and the number of atoms thereof is counted.

When X of the formula (1) is a group of the formula (2), the number of atoms of the divalent main chain represented by —$R^5$—$A^3$—$R^4$—$A^2$—$R^3$—$A^1$— is preferably 7 to 9, more preferably 7 or 8.

When X of the formula (1) is a group of the formula (3) or (4), the number of atoms of the divalent main chain represented by —$R^5$—$A^3$—$R^4$—$A^2$—$R^3$—$A^1$— is preferably 5 to 7, more preferably 5 or 6.

When $A^1$ of the formula (1) is —CO—$A^4$— ($A^4$ is the same as defined above), $A^4$ should bond with —CO— at the amino terminal.

When $A^2$ or $A^3$ of the formula (1) is —CO—$A^5$—$NR^8$— ($R^8$ and $A^5$ are the same as defined above) or —$NR^8$—$A^5$—CO— ($R^8$ and $A^5$ are the same as defined above), $A^5$ should bond with —CO— at the amino terminal.

In the divalent group of the formula (1) represented by —$R^5$—$A^3$—$R^4$—$A^2$—$R^3$—$A^1$—, the carbon atom substituted by a hydroxy group should not bond with other nitrogen atom, sulfur atom or oxygen atom. Besides, two nitrogen atoms therein should not bond with the same carbon atom in $SP^3$.

In the formula (1), the preferable groups for $R^3$, $R^4$ and $R^5$ are a single bond, or a straight chain alkylene, alkenylene or alkynylene group which may optionally be substituted by 1 to 2 groups selected from the group consisting of a hydroxy group, an oxo group, a halogen atom, an aryl group and a cycloalkyl group, more preferably a single bond, an unsubstituted straight chain alkylene group, a straight chain alkylene group substituted by 1 to 2 groups selected from a hydroxy group, an oxo group and a halogen atom.

In the formula (1), the preferable groups for $A^3$ are a single bond, an oxygen atom, —$S(O)_n$— (n is the same as defined above), a divalent group of monocyclic hydrocarbons, or a divalent group of monocyclic heterocyclic group, more preferably, a single bond, an oxygen atom, a divalent group of monocyclic hydrocarbons, or a divalent group of monocyclic heterocyclic group.

In the formula (1), the preferable groups for $A^2$ are a single bond, an oxygen atom, —CO—$NR^7$— ($R^7$ is the same as defined above), —$NR^7$—CO— ($R^7$ is the same as defined above), —CO—$A^5$—$NR^8$— ($A^5$ and $R^8$ are the same as defined above), —$NR^8$—$A^5$—CO— ($A^5$ and $R^8$ are the same as defined above), a divalent group of monocyclic hydrocarbons, or a divalent group of monocyclic heterocyclic group. The more preferable groups for $A^2$ are a single bond, —CO—$NR^7$— ($R^7$ is the same as defined above), —$NR^7$—CO— ($R^7$ is the same as defined above), —CO—$A^5$—$NR^8$— ($A^5$ and $R^8$ are the same as defined above), —$NR^8$—$A^5$—CO— ($A^5$ and $R^8$ are the same as defined above) when $A^1$ is —CO—, or a single bond, —CO—$NR^7$— ($R^7$ is the same as defined above), —$NR^7$—CO— ($R^7$ is the same as defined above) when $A^1$ is —CO—$A^4$— ($A^4$ is the same as defined above).

When $R^4$ of the formula (1) is a single bond, one of $A^3$ or $A^2$ may preferably be a single bond.

When $R^3$ of the formula (1) is a single bond, $A^2$ is preferably a single bond.

The modifying groups for hydroxy group, thiol group, carboxyl group, amido group, amino group, amidino group, imidazolyl group and indolyl group are protecting groups for the side chain of amino acid disclosed in Izumiya, et al., Fundamental Study and Experiments of Peptide Synthesis (published by MARUZENE, 1985), or Greene, et al. Protective Groups in Organic Synthesis, (published by John Willey & Sons, 1991).

The modifying groups for hydroxyl group include an ether-type modifying group or an acyl-type modifying group. The ether-type modifying groups are, for example, benzyl, 2-nitrobenzyl, 2,6-dichlorobenzyl, t-butyl, etc. The acyl-type modifying groups are, for example, a lower alkanoyl group, which is a straight chain or branched chain alkanoyl group having up to 5 carbon atoms, such as acetyl, propanoyl, butanolyl, etc. The modifying groups for thiol group include a sulfide-type modifying group, etc., for example, benzyl, 4-methylbenzyl, 4-nitrobenzyl, 4-methoxybenzyl, acetamidomethyl, etc. The modifying group for carboxyl group includes an ester-type modifying group, such as a lower alkyl group, 2,2,2-trichloroethyl, benzyl, 4-methoxybenzyl, diphenylethyl, etc. The modifying group for amido group includes, for example, 2,4-dimethoxybenzyl, etc. The modifying group for amino group includes an urethane-type modifying group or an acyl-type modifying group. The urethane-type modifying groups are, for example, benzyloxycarbonyl, 4-nitrobenzyloxycarbonyl, 4-methoxybenzyloxycarbonyl, 2-methanesulfonylethoxycarbonyl, 2,2,2-trichloroethoxycarbonyl, t-butyloxycarbonyl, 9-fluorenylmethoxycarbonyl, etc. The acyl-type modifying groups are, for example, formyl, acetyl, benzoyl, trifluoroacetyl, etc. The modifying group for amidino group or guanidino group includes an urethane-type modifying group such as benzyloxycarbonyl, t-butyloxycarbonyl, etc., 4-toluenesulfonyl, 4-methoxybenzenesulfonyl, nitro, etc. In case of urethane-type modifying group, one or two urethane-type modifying groups may be introduced, and in case of other modifying groups, only one modifying group is introduced. The modifying group for imidazolyl group includes, for example, 4-toluenesulfonyl, benzyloxycarbonyl, benzyl, etc. The modifying group for indolyl group includes, for example, formyl, benzyloxycarbonyl, etc.

The present compound of the formula (1) can be prepared by a conventional method from easily obtainable starting materials and reagents, for example, by a method disclosed below or a modified method thereof. The processes for preparing the present compound (1) are explained in the following (a) to (h).

(a) The Process for Preparing the Compound (1) Wherein Both $A^2$ and $A^3$ Are a Single Bond (i.e. the Compound of the Formula (11))

The compound (11) is prepared by the following scheme.

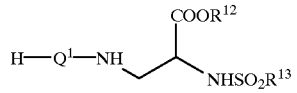

Formula (12)

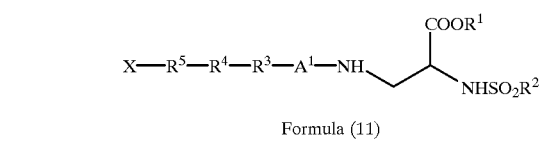

Formula (13)

$\xrightarrow{\text{removal of protecting group}}$

X—R$^5$—R$^4$—R$^3$—A$^1$—NH—CH(COOR$^1$)—NHSO$_2$R$^2$

Formula (11)

wherein R$^1$, R$^2$, R$^3$, R$^4$, R$^5$, A$^1$ and X are the same as defined above, R$^{12}$, R$^{13}$, R$^{14}$, R$^{15}$ and R$^{16}$ are the same as R$^1$, R$^2$, R$^3$, R$^4$ and R$^5$, which are, if necessary, protected by a protecting group, respectively, Q$^1$ is a single bond or —Q$^2$— (Q$^2$ is the same as A$^4$ (A$^4$ is the same as defined above) which is, if necessary, protected by a protecting group), and X$^1$ is the same as X (X is the same as defined above) which is, if necessary, protected by a protecting group.

That is, the above process is carried out by condensing the compound (12) and the compound (13) by amido-bond producing reaction, followed by removing the protecting groups, if necessary.

The amido-bond producing reaction is carried out by a conventional method, for example, by a method disclosed in Izumiya, et al., Fundamental Study and Experiments of Peptide Synthesis (published by MARUZENE, 1985). For example, a compound having a free amino group and a compound having a free carboxyl group are reacted with stirring in the presence of a condensing agent such as 1-(3-dimethylaminopropyl)-3-ethylcarbodiimide hydrochloride, etc., in an inert solvent such as N,N-dimethylformamide, dichloromethane, acetonitrile, etc., at a temperature of from 0° C. to 40° C. for 1 to 24 hours. If necessary, the reaction is carried out in the presence of an additive such as 1-hydroxybenzotriazole, etc., or in the presence of a base such as triethylamine, etc.

The compound (12) is prepared by a conventional method from easily obtainable starting materials. That is, the compound (12) is prepared by using a carboxylic acid compound, a ketone compound, an aldehyde compound or a halide compound, which is represented by a compound of the formula (14):

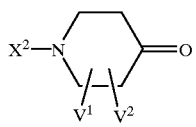

wherein V$^1$ and V$^2$ are the same as defined above, X$^2$ is a protecting group for amino group, a compound of the formula (15):

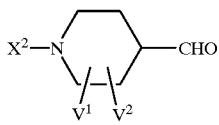

wherein V$^1$, V$^2$ and X$^2$ are the same as defined above, a compound of the formula (16):

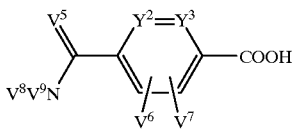

wherein V$^5$, V$^6$, V$^7$, Y$^2$ and Y$^3$ are the same as defined above, V$^8$ and V$^9$ are the same or different and each a hydrogen atom, an alkyl group, a substituted lower alkyl group, a cycloalkyl group, an amino group, an acylamino group, a lower alkyloxycarbonyl group, a lower alkyloxycarbonyl group substituted by an aryl group, or a protecting group for amidino group, a group of the formula (17):

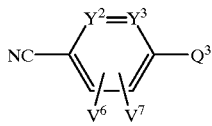

wherein V$^6$, V$^7$, Y$^2$ and Y$^3$ are the same as defined above, Q$^3$ is a carboxyl group, formyl group or X$^3$ (X$^3$ is bromine atom, iodine atom or chlorine atom), or a group of the formula (18):

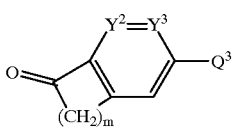

wherein m, Q$^3$, Y$^2$ and Y$^3$ are the same as defined above, by carbon atom-increasing reaction such as Horner-Emmons Reaction, Wittig Reaction, Grignard Reaction, Coupling Reaction using palladium, etc., catalytic hydrogenation reaction in the presence of a suitable catalyst, reduction using boron hydride compounds such as sodium borohydride, etc., aluminum hydride compounds such as lithium aluminum hydride, etc., oxidization reaction such as Collins oxidization, PCC oxidization, Swern oxidization, or by a combination of these reactions. In this reaction, the protection procedure or the removal of protecting group is also applied when necessary.

When the compound (17) is used as a starting compound, the cyano group thereof is converted into an amidino group or into an amido group at a suitable step by a conversion method disclosed in J. Med. Chem. 35, 4393 (1992), Pharmazie, 33, 39 (1978) or Org. Synth., II, 44 (1943), etc., which is illustrated below.

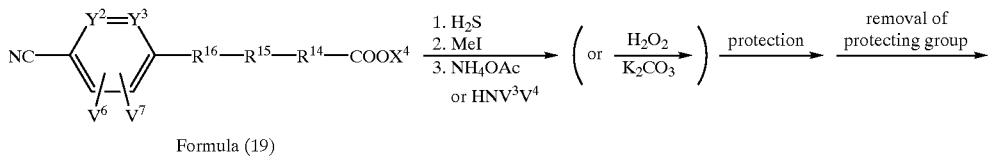

Formula (19)

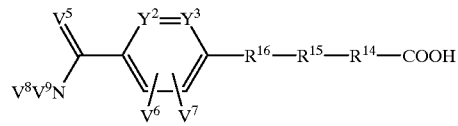

wherein $V^3$, $V^4$, $V^5$, $V^6$, $V^7$, $V^8$, $V^9$, $Y^2$, $Y^3$, $R^{14}$, $R^{15}$ and $R^{16}$ are the same as defined above, $X^4$ is a protecting group for carboxyl group.

The compound (19) is treated with hydrogen sulfide and methyl iodide, followed by reacting the product with ammonium acetate or an amine compound to be converted into an amidino compound. The amidino group thereof is protected, and then the protecting group for carboxyl group is removed. Alternatively, the compound (19) is treated with aqueous hydrogen peroxide solution in the presence of potassium carbonate, and if necessary, introducing thereto groups of $V^8$ and $V^9$, and followed by removing the protecting group for carboxyl group to give an amido compound.

When the compound (18) is used as a starting compound, the compound (18) is prepared by converting the compound (20) into an amido compound, followed by converting the product into an amidino compound, as illustrated below.

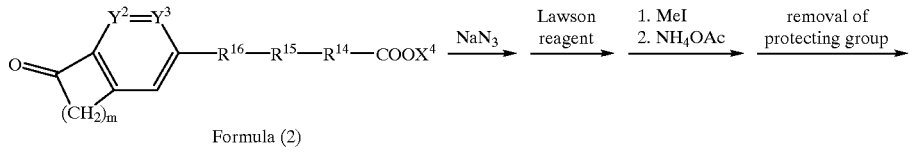

Formula (2)

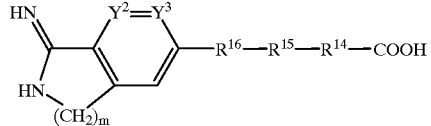

wherein m, $X^4$, $Y^2$, $Y^3$, $R^{14}$, $R^{15}$ and $R^{16}$ are the same as defined above The compound (12) is prepared, for example, by a method of introducing a protecting group into a commercially available compound, a method disclosed in J. Med. Chem., 35, 4393 (1992), J. Med. Chem., 36, 1811 (1993) or Japanese Patent First Publication (Kokai) No. 288051/1992, or by methods disclosed in Examples.

The compound (13) is prepared by condensing the compound (21) with 1 to 3 protected amino acid derivatives, if necessary, by amido-bond producing reaction, and if required, followed by removing the protecting groups, as illustrated below.

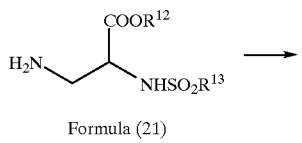

Formula (21)

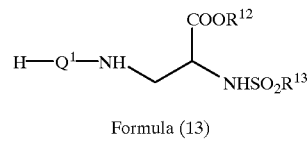

Formula (13)

wherein $R^{12}$, $R^{13}$ and $Q^1$ are the same as defined above.

The condensation reaction is preferably carried out from the carboxyl terminal, but optionally be carried out by fragment condensation reaction, as illustrated by Examples.

The compound (21) is prepared by a method disclosed in Synthesis, 1981, 266, from commercially available asparagine derivatives. Besides, the compound (21) is also prepared from commercially available 2,3-diaminopropionic acid and a derivative thereof, as illustrated below.

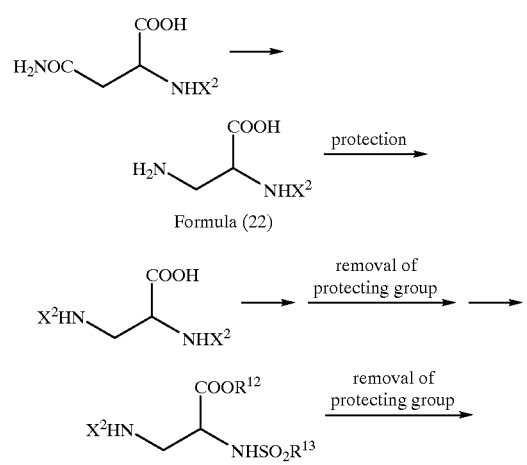

Formula (22)

-continued

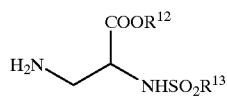

wherein $R^{12}$, $R^{13}$ and $X^2$ are the same as defined above, and $X^5$ is a protecting group for amino group.

The 3-amino group of the compound (22) is protected, and $R^{12}$ is introduced into the carboxyl group thereof, and the protecting group for the 2-amino group is removed, and then $R^{13}SO_2$ is introduced thereto, and further the protecting group for the 3-amino group is removed to give the compound (21).

The process for introduction of $R^{13}SO_2$ is carried out by treating a free amino group with a halide compound of a corresponding sulfonic acid, a halide compound or an anhydride compound of a corresponding carboxylic acid or monoester compound of carboxylic acid. For example, a halide compound or an anhydride compound is stirred in an inert solvent such as N,N-dimethylformamide, dichloromethane, ethyl acetate, 1,4-dioxane, or in a mixture of these solvents, at a temperature of from 0° C. to 80° C. for 1 to 24 hours. If necessary, a base such as triethylamine, pyridine, sodium hydrogen carbonate, etc. may be added thereto.

(b) The Process for Preparing the Compound (1) Wherein $A^3$ is a Single Bond, $A^2$ is —CO—$NR^7$— and $R^3$ is Not a Single Bond (i.e. the Compound of the Formula (23))

The compound (23) is prepared by the following scheme.

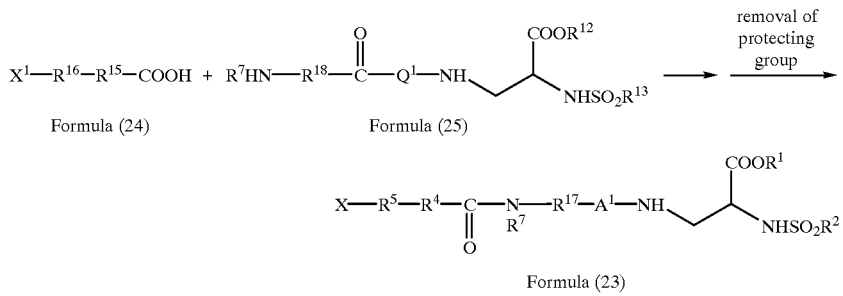

Formula (24)        Formula (25)

Formula (23)

wherein $R^1$, $R^2$, $R^4$, $R^5$, $R^7$, $A^1$, X, $X^1$, $Q^1$, $R^{12}$, $R^{13}$, $R^{15}$ and $R^{16}$ are the same as defined above, $R^{17}$ is an alkylene, alkenylene or alkynylene group which may optionally be substituted by 1 to 4 groups selected from the group consisting of a hydroxy group, an oxo group, a halogen atom, an aryl group and a cycloalkyl group, and $R^{18}$ is the same as $R^{17}$ ($R^{17}$ is the same as defined above) which is, if necessary, protected by a protecting group.

The above process is carried out by condensing the compound (24) and the compound (25) by amido-bond producing reaction, and if necessary, followed by removing the protecting group.

The compound (24) is prepared, for example, by the process for preparing the compound (12) in the above process (a).

The compound (25) is prepared by the following scheme.

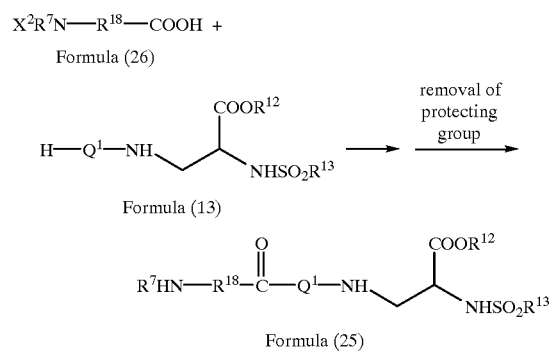

Formula (25)

wherein $R^7$, $X^2$, $Q^1$, $R^{12}$, $R^{13}$ and $R^{18}$ are the same as defined above.

The above process is carried out by condensing the compound (26) and the compound (13) by amido-bond producing reaction, and if necessary, followed by removing $X^2$, which is a protecting group for amino group.

The compound (26) is prepared by a conventional method, for example, by introducing a protecting group into the amino group of the aminocarboxylic acid in general. The compound (26) wherein $R^7$ is a lower alkyl group is prepared by introducing a lower alkyl group by a method disclosed in Can. J. Chem., 55, 906 (1977). For example, the compound (26) is prepared by introducing an urethane-type protecting group such as t-butoxycarbonyl group into a corresponding aminocarboxylic acid, followed by treating the product with sodium hydride and $R^7$—$X^3$ ($R^7$ and $X^3$ are the same as defined above).

(c) The Process for Preparing the Compound (1) Wherein $A^3$ is a Single Bond, $A^2$ is —CO—$A^5$—$NR^8$ and $R^3$ is Not a Single Bond (i.e. the Compound (27))

The compound (27) is prepared by the following scheme.

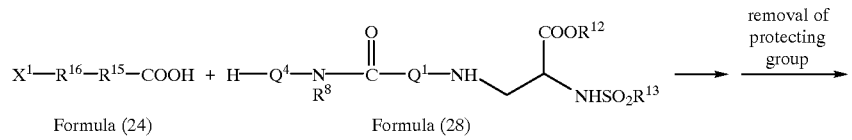

Formula (24)        Formula (28)

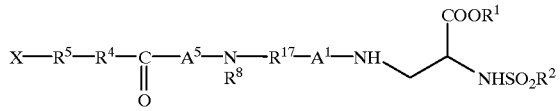

Formula (27)

wherein $R^1$, $R^2$, $R^4$, $R^5$, $R^8$, $A^1$, $A^5$, X, $X^1$, $R^{12}$, $R^{13}$, $R^{15}$, $R^{16}$, $R^{17}$, $R^{18}$ and $Q^1$ are the same as defined above, $Q^4$ is the same as $A^5$ ($A^5$ is the same as defined above), which is, if necessary, protected by a protecting group.

The above process is carried out by condensing the compound of the formula (24) and the compound (28) by amido-bond producing reaction, and if necessary, followed by removing the protecting group.

The compound of the formula (28) is prepared by condensing successively the compound of the formula (25) with amino acid derivatives comprising $Q^4$ by amido-bond producing reaction.

(d) The Process for Preparing the Compound of the Formula (1) Wherein $A^3$ is a Single Bond, $A^2$ is a Group of the Formula: —$NR^7$—CO—, and $R^3$ is Not a Single Bond (i.e. the Compound of the Formula (29))

The compound of the formula (29) is prepared by the following scheme.

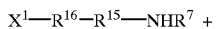

Formula (30)

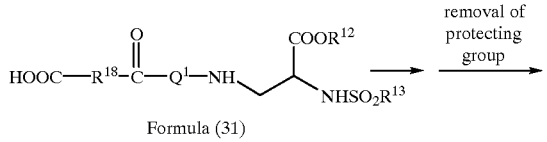

Formula (31)

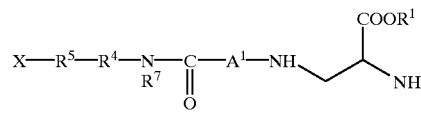

Formula (29)

wherein $R^1$, $R^2$, $R^4$, $R^5$, $R^7$, $A^1$, X, $X^1$, $Q^1$, $R^{12}$, $R^{13}$, $R^{15}$, $R^{16}$, $R^{17}$ and $R^{18}$ are the same as defined above.

The process is carried out by condensing the compound (30) and the compound (31) by amido-bond producing reaction, and if necessary, followed by removing the protecting group.

The compound (30) is prepared by a conventional manner, for example, by the following scheme from the compound of the formula (32).

Formula (30)

wherein $R^7$, $X^1$, $R^{15}$, $R^{16}$ and $X^3$ are the same as defined above.

For example, the compound of the formula (30) is prepared by reacting the alcohol compound of the formula (32) with triphenylphosphine and carbon tetrabromide to give the compound of the formula (33), and reacting the compound (33) with potassium phthalimide, treating the product with hydrazine hydrate to give the compound (34), and if necessary, followed by alkylation of the amino group of the compound (34) with a lower alkyl group by a method disclosed in Can. J. Chem., 55, 906 (1977), and removing the protecting group. The compound of the formula (32) is prepared by the method disclosed in the above (a), for example, by using a commercially available 4-hydroxypiperidinol, or converting the carboxyl group of the compound of the formula (24), etc. into N-hydroxysuccinimide ester, and followed by reducing the product with sodium borohydride, etc.

The compound of the formula (31) is prepared by the following scheme.

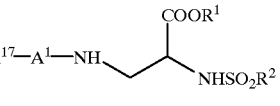

Formula (35)

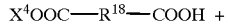

Formula (13)

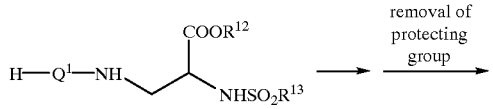

Formula (31)

wherein $R^{12}$, $R^{13}$, $R^{18}$, $X^4$ and $Q^1$ are the same as defined above.

The compound of the formula (31) is prepared by condensing the compound (35) and the compound (13) by an amido-bond producing reaction, followed by removing the protecting group. The compound (35) is prepared by a conventional manner, for example, by using a commercially available dicarboxylic acid monoester.

Instead of the compound (35), a compound of the formula (37) may be used in the process.

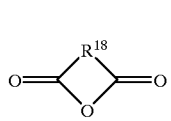

Formula (37)

wherein $R^{18}$ is the same as defined above.

(e) The Process for Preparing the Compound of the Formula (1), Wherein $A^3$ is a Single Bond, $A^2$ is —$NR^8$—$A^5$—CO— and $R^3$ is Not a Single Bond (i.e. the Compound of the Formula (37)):

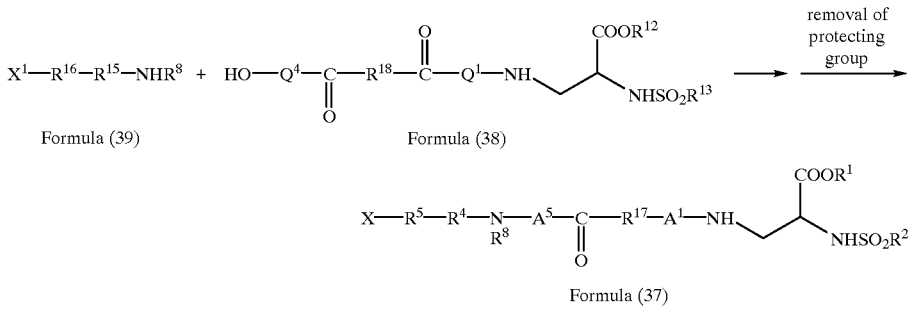

Formula (39)   Formula (38)   Formula (37)

wherein $R^1$, $R^2$, $R^4$, $R^5$, $R^8$, $R^{12}$, $R^{13}$, $R^{15}$, $R^{16}$, $R^{17}$, $R^{18}$, $A^1$, $A^5$, X, $X^1$, $Q^1$ and $Q^4$ are the same as defined above.

The process is carried out by condensing the compound (39) and the compound (38) by an amido-bond producing reaction, and if necessary, followed by removing the protecting group.

The compound of the formula (38) is prepared by condensing successively the compound of the formula (31) and amino acid derivatives comprising $Q^4$ by an amido-bond producing reaction, in the same manner as in the process of above (a).

The compound (39) is prepared in the same manner as in the preparation of the compound (30).

(f) The Process for Preparing the Compound of the Formula (1) Wherein $A^3$ is a Single Bond, $A^2$ is an Oxygen Atom and $R^3$ is Not a Single Bond (i.e. the Compound of the Formula (40)):

The compound of the formula (40) is prepared by the following scheme.

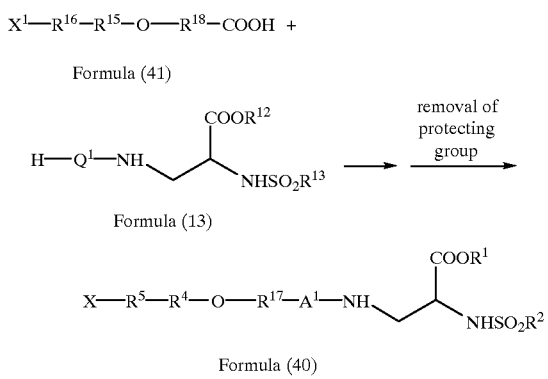

Formula (41)

Formula (13)

Formula (40)

wherein $R^1$, $R^2$, $R^4$, $R^5$, $R^{12}$, $R^{13}$, $R^{15}$, $R^{16}$, $R^{17}$, $R^{18}$, $A^1$, X, $X^1$ and $Q^1$ are the same as defined above.

The process is carried out by condensing the compound (41) and the compound (13) by an amido-bond producing reaction, and if necessary, followed by removing the protecting group.

The compound of the formula (41) is prepared by a conventional method, for example, by the following scheme.

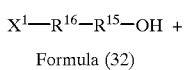

Formula (32)

-continued $X^3$—$R^{18}$—$COOX^6$ $\xrightarrow{\text{removal of protecting group}}$ Formula (42)

$X^1$—$R^{16}$—$R^{15}$—O—$R^{18}$—COOH

Formula (41)

wherein $X^1$, $X^3$, $R^{15}$, $R^{16}$ and $R^{18}$ are the same as defined above, and $X^6$ is sodium, lithium, potassium or a protecting group for carboxyl group.

The compound (32) and the compound (42) are stirred in the presence of a base such as sodium hydrogen carbonate, potassium carbonate, sodium hydroxide, sodium hydride, in an inert solvent such as N,N-dimethylformamide, dichloromethane, ethyl acetate, THF, at a temperature of from 0 to 120° C., for 1 to 24 hours, and if necessary, followed by removing a group represented by $X^6$ from the product to give the compound (41).

The compound (42) is prepared by a conventional manner, but a commercially available one can be used, or the compound (42) is prepared by protecting a carboxyl group of hydroxycarboxylic acid with a protecting group, followed by converting the hydroxy group into a halogen atom by the same method as used in the preparation of the compound (33).

(g) The Process for Preparing the Compound of the Formula (1) Wherein $A^3$ is a Divalent Group of a Monocyclic Hydrocarbons or a Divalent Group of a Monocyclic Heterocyclic Group, $A^2$ and $R^3$ are Both a Single Bond, and $A^1$ is —CO— (i.e. the Compound of the Formula (43)):

The compound of the formula (43) is prepared by the following scheme.

$X^1$—$R^{16}$—$Q^5$—$R^{15}$—COOH +

Formula (44)

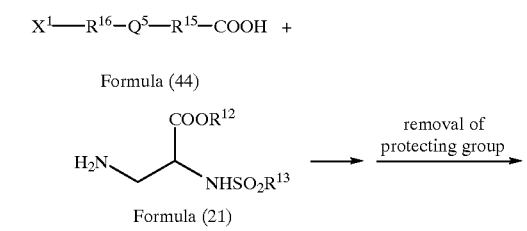

Formula (21)

-continued

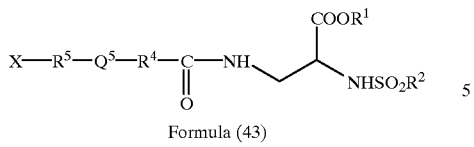
Formula (43)

wherein $R^1$, $R^2$, $R^4$, $R^5$, $R^{12}$, $R^{13}$, $R^{15}$, $R^{16}$, X and $X^1$ are the same as defined above, and $Q^5$ is a divalent group of a monocyclic hydrocarbons or a divalent group of a monocyclic heterocyclic group.

The process is carried out by condensing the compound (44) and the compound (21) by an amido-bond producing reaction, and if necessary, followed by removing the protecting group.

The compound (44) is prepared by a conventional manner, for example, by the method disclosed in EP 537980.

The processes for preparing the compound (45), the compound (50), the compound (51), the compound (53) and the compound (54) are exemplified below, as the representatives of the compound (44).

The compound (45) is prepared by the following scheme.

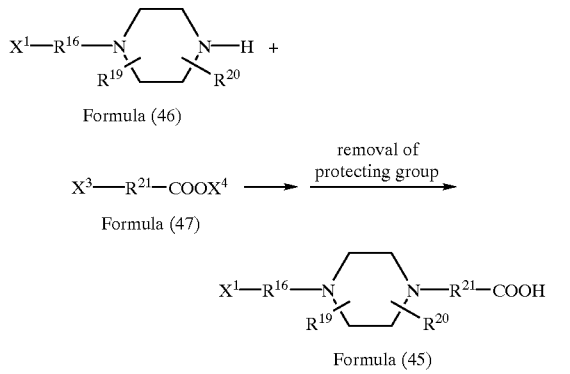
Formula (45)

wherein $R^{16}$, $X^1$, $X^3$ and $X^4$ are the same as defined above, $R^{19}$ and $R^{20}$ are independently a hydrogen tom or a lower alkyl group, $R^{21}$ is an alkylene, alkenylene or alkynylene group which may optionally be substituted by 1 to 4 groups selected from a hydroxy group, an oxo group, a halogen atom, an aryl group and a cycloalkyl group, and may optionally be protected by a protecting group.

The compound (45) is prepared by stirring the compound (46) and the compound (47) in an inert solvent such as N,N-dimethylformamide, dichloromethane, ethyl acetate, etc., in the presence of a base such as sodium hydrogen carbonate, triethylamine, potassium carbonate, etc.

The compound of the formula (46) is prepared by the following scheme.

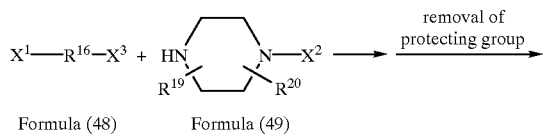
Formula (48)    Formula (49)

-continued

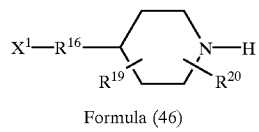
Formula (46)

wherein $R^{16}$, $R^{19}$, $R^{20}$, $X^1$, $X^2$ and $X^3$ are the same as defined above.

The compound (46) is prepared from the compound (48) and the compound (49) in the same manner as in the preparation of the compound (45).

The compound (48) and the compound (49) are prepared by the above methods.

The compound (50) is prepared by the following scheme.

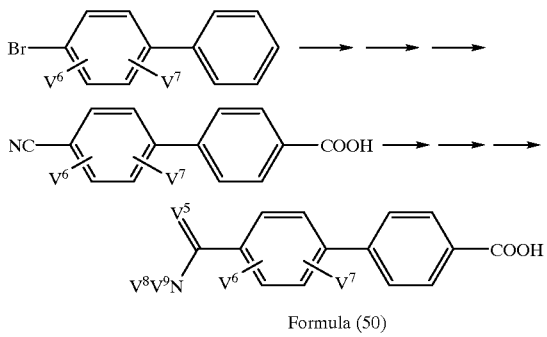
Formula (50)

wherein $V^5$, $V^6$, $V^7$, $V^8$ and $V^9$ are the same as defined above.

4-Bromobiphenyl derivative is treated by the method disclosed in Japanese Patent First Publication (Kokai) No. 41852/1979, etc. to give 4-cyano-4'-carboxylbiphenyl derivative, which is further reacted according to the method of the preparation of the compound (12) to give the compound (50).

The compound (51) is prepared by the following scheme.

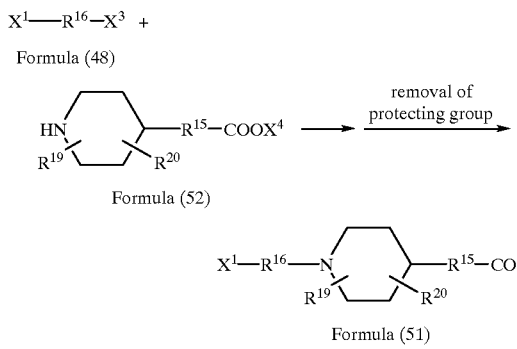
Formula (51)

wherein $X^1$, $R^{15}$, $R^{16}$, $R^{19}$, $R^{20}$, $X^3$ and $X^4$ are the same as defined above.

The compound (51) is prepared from the compound (48) and the compound (52) by the same manner as in the preparation of the compound (46).

The compound (52) is prepared by the same manner as in the preparation of the compound (12).

The compound (53) is prepared by the following scheme.

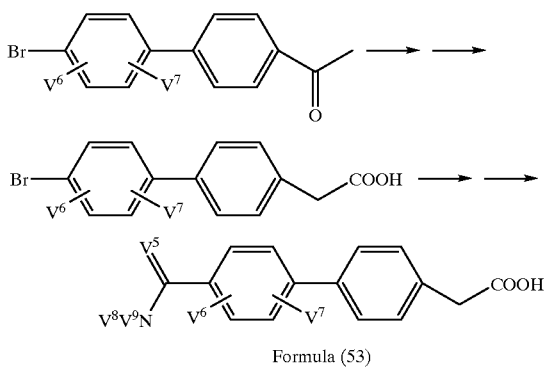

Formula (53)

wherein $V^5$, $V^6$, $V^7$, $V^8$ and $V^9$ are the same as defined above.

That is, 4-bromo-4'-acetylbiphenyl, which is a synthetic intermediate of the compound (50), is treated by the method disclosed in Examples, to give 4'-bromo-4-biphenylyl acetic acid, and then, followed by treating the product in the same manner as in the preparation of the compound (50).

The compound (54) is prepared by the following scheme.

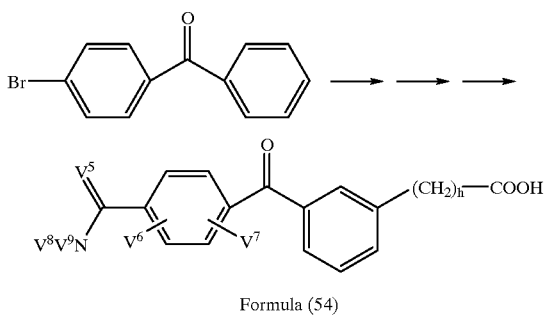

Formula (54)

wherein $V^5$, $V^6$, $V^7$, $V^8$, $V^9$ and h are the same as defined above.

That is, the compound (54) is prepared by acylating a commercially available 4-bromobenzophenon in a conventional manner, and followed by treating the product in the same manner as in the preparation of the compound (50) or the compound (53).

(h) The Process for Preparing the Compound of the Formula (1) Wherein $A^3$ is a Single Bond, $A^2$ is —$NR^6$— or —O—, $A^1$ is —CO—, and $R^3$ is a Single Bond (i.e. the Compound of the Formula (55)):

The compound (55) is prepared by the following scheme.

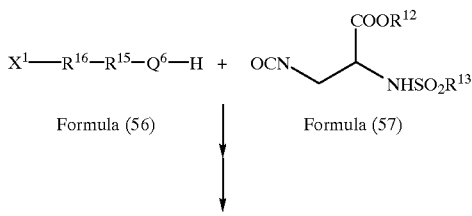

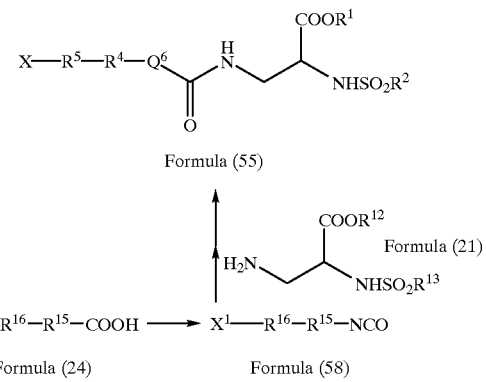

Formula (55)

$X^1$—$R^{16}$—$R^{15}$—COOH ⟶ $X^1$—$R^{16}$—$R^{15}$—NCO

Formula (24)　　　　　　　　Formula (58)

wherein $R^1$, $R^2$, $R^4$, $R^5$, $R^{12}$, $R^{13}$, $R^{15}$, $R^{16}$, X and $X^1$ are the same as defined above, and $Q^6$ is —O— or —$NR^6$— ($R^6$ is the same as defined above).

That is, the compound (57) is prepared by converting the 3-carboxyl group of aspartic acid into an acid azide by the method disclosed in Angew. Chem., Int. Ed. Engl., 12, 842 (1973), Synthesis, 1989, 131, Justus Liebigs Ann. Chem., 566, 210 (1950), The fourth ed. Jikken Kagaku Koza Vol. 20, pp. 355–365, pp. 373–483 (Maruzen), followed by further converting it into an isocyanate compound by Curtius conversion, and the thus prepared compound (57) and the compound (56) are reacted, and then the function groups are converted and the protecting groups are removed in suitable stages to give the compound (55). Alternatively, the compound (24) is treated in the same manner of the preparation of the compound (57) to give the compound (58), which is reacted with the compound (21), and the function groups thereof are converted and the protecting groups are removed in suitable stages to give the compound (55).

The above processes (a) to (h) are merely exemplified, but the present compound may be prepared with changing the order of the reactions of these processes, or other processes.

Besides, the compounds of the formula (1) other than the above can also be prepared by the similar method to the above processes (a) to (h).

The protecting groups for hydroxy group, for thiol group, for carboxyl group, for amido group, for amino group, for guanidino group, for imidazolyl group, for indolyl group and for amidino group are, for example, protecting groups for the side chain of amino acid disclosed in Izumiya et al., Fundamental Study and Experiments of Peptide Synthesis (Maruzene, 1985), or Greene, Protective Groups in Organic Synthesis (Johne Willey & Sons, 1991).

The protecting group for hydroxy group may be an ether-type protecting group or an acyl-type protecting group. The ether-type protecting group is, for example, benzyl, 2-nitrobenzyl, 2,6-dichlorobenzyl, t-butyl, etc. The acyl-type protecting group is, for example, a lower alkanoyl group, etc. The lower alkanoyl group is, for example, a straight chain or branched chain alkanoyl group having up to 5 carbon atoms, such as acetyl, propanoyl, butanoyl, etc. The protecting group for thiol group may be a sulfide-type protecting group, etc. for example, benzyl, 4-methylbenzyl, 4-nitrobenzyl, 4-methoxybenzyl, acetamidomethyl, etc. The protecting group for carboxyl group may be an ester-type protecting group, for example, a lower alkyl group, 2,2,2-trichloroethyl, benzyl, 4-methoxybenzyl, diphenylethyl, etc. The protecting group for amido group may be 2,4-dimethoxybenzyl, etc. The protecting group for amino group may be an urethane-type protecting group or an acyl-type protecting group, etc. The urethane-type protecting group may be, for example, benzyloxycarbonyl, 4-nitrobenzyloxycarbonyl, 4-methoxybenzyloxycarbonyl, 2-methanesulfonylethoxycarbonyl, 2,2,2-trichloroethoxycarbonyl, t-butyloxycarbonyl, 9-fluorenylmethoxycarbonyl, etc. The acyl-type protecting group may be, for example, formyl, acetyl, benzoyl, trifluoroacetyl, etc. The protecting group for guanidino group may be, for example, an urethane-type protecting group such as benzyloxycarbonyl, t-butyloxycarbonyl, etc., 4-toluenesulfonyl, 4-methoxybenzenesulfonyl, nitro, etc. In case of urethane-type protecting group, one or two urethane-type protecting groups may be introduced, and in case of other protecting groups, only one protecting group is introduced. The protecting group for imidazolyl group may be, for example, 4-toluenesulfonyl group, benzyloxycarbonyl group, benzyl group, etc. The protecting group for indolyl group may be formyl group, benzyloxycarbonyl group, etc. The protecting group for amidino group may be an urethane-type protecting group such as t-butoxycarbonyl, benzyloxycarbonyl, etc.

The method for introduction of each modifying group and each protecting group and the removal of the protecting group are disclosed in Greene, et al., Protective Groups in Organic Synthesis (Johne Willey & Sons, 1991), or Izumiya et al., Fundamental Study and Experiments of Peptide Synthesis (Maruzene, 1985).

The method for introduction of a modifying group or protecting group for amino group and the method for the removal of the protecting group are explained below. t-Butoxycarbonyl group is introduced into a free amino group by stirring with di-t-butyldicarbonate in an inert solvent such as 1,4-dioxane/water at 0 to 40° C. for 0.5 to 24 hours. The removal of t-butoxycarbonyl group is carried out by stirring by using an acid such as TFA or 4N HCl-dioxane at 0 to 40° C. for 0.5 to 6 hours. Benzyloxycarbony group may be introduced into a free amino group by adding carbobenzoxy chloride in an inert solvent such as 1,4-dioxane, methanol, and further by stirring the mixture at 0 to 40° C. for 0.5 to 24 hours. The removal of benzyloxycarbonyl group is carried out by hydrogenation in the presence of a noble metal catalyst such as palladium-carbon (Pd/C).

The method for introduction of a modifying group or protecting group for carboxyl group and the method for the removal of the protecting group are explained below. For example, methyl and ethyl ester may be introduced into a free carboxyl group by stirring in an inert solvent such as dichloromethane, in the presence of methanol or ethanol, and dimethylaminopyridine and a condensing agent such as 1-(3-dimethylaminopropyl)-3-ethylcarbodiimide hydrochloride at 0 to 40° C. for 0.5 to 24 hours. The removal of these groups may be carried out by stirring in an inert solvent such as methanol in the presence of a base such as 1N aqueous sodium hydroxide solution at 0 to 40° C. for 0.5 to 6 hours.

The method for introduction of a modifying group or protecting group for amidino group and the method for the removal of the protecting group are explained below. For example, t-butoxycarbonyl group may be introduced in the same manner as used as a protecting group for amino group, or may be introduced into a free amidino group by stirring in an inert solvent such as dichloromethane, acetonitrile, etc., in the presence of N,O-bistrimethylsilylacetamide for 0.5 to 3 hours, then by adding thereto di-t-butyldicarbonate, followed by stirring the mixture at 0 to 40° C. for 0.5 to 24 hours. The removal of t-butoxycarbonyl group is carried out by treating with an acid such as TFA or 4N HCl-dioxane with stirring at 0 to 40° C. for 0.5 to 6 hours.

The introduction of other modifying groups or other protecting group and the removal of the protecting groups are also carried out by a conventional method, for example, by the methods disclosed in Izumiya et al., Fundamental Study and Experiments of Peptide Synthesis (Maruzene, 1985), or Protective Groups in Organic Synthesis (Johne Willey & Sons, 1991).

The protecting group should be selected to be one which does not cause other modifying groups or protecting groups to remove during the reaction or the removal of said protecting group.

The compounds of the formula (1) can be purified by a conventional purifying method, for example, recrystallization, high performance liquid chromatography, etc.

The pharmaceutically acceptable salt may be a pharmaceutically acceptable acid addition salt or base addition salt. The acid addition salt is, for example, a salt with an inorganic acid such as hydrochloride, sulfate, phosphate, etc., or a salt with an organic acid such as acetate, butyrate, methanesulfonate, trifluoroacetate, citrate, fumarate, maleate, succinate, salicylate, etc. The base addition salt is a salt with an inorganic base, or a salt with an organic base. The salt with an inorganic base is, for example, an alkali metal salt such as sodium salt, potassium salt, etc., an alkaline earth metal salt such as magnesium salt, calcium salt, etc., or ammonium salt. The salt with an organic base is, for example, a salt with a basic amino acid such as arginine salt, lysine salt, etc. These salts may be prepared by a conventional method. For example, an acetate is prepared by dissolving the compound of the formula (1) in water, followed by adding thereto a necessary amount of acetic acid.

The animals to which the present compounds can be administered are not limited, and include, for example, in addition to human, various mammals such as mouse, rat, dog, cat, cow, horse, goat, sheep, rabbit, pig, etc.

The present compound may be administered to these animals or human by a conventional administration route, for example, orally, intramuscularly, intravenously, subcutaneously, intraperitoneally, or intranasally. The dosage and the frequency of the administration vary according to kinds of animals to be administered, administration routes, severity of conditions and weights of patients, and should not be limited, but when administered to human, the daily dosage is in the range of about 1 mg to 1 g for an adult, by a single dose, or by multiple doses. The dosage form is in the form of powder, fine granules, granules, tablets, capsules, suppositories, injections, intranasal preparation, etc. These preparations are prepared by using conventional pharmaceutically acceptable carriers or diluents in a conventional manner. That is, a preparation for oral administration is prepared by adding, if necessary, a binder, a disintegrator, a lubricant or a coloring agent, followed converting the mixture to tablets, granules, powders, capsules, by a conventional method. In the preparation of injection preparation, a pH adjustor, a buffering agent, a stabilizer or an emulsifying agent may be added, and the mixture is converted into an injection form, by a conventional manner.

The present invention can provide a 2,3-diaminopropionic acid derivative which is useful as a platelet aggregation inhibitor, a cancer metastasis inhibitor, a would healing agent, or a bone resorption inhibitor.

BEST MODE FOR CARRYING OUT THE INVENTION

The present invention is illustrated in more detail by the representative compounds of the present invention and Examples, but should not be construed to be limited thereto.

The representative compounds of the present invention are exemplified below.
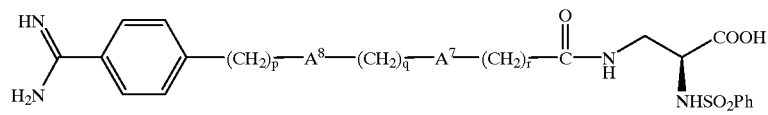
| p | q | r | $A^8$ | $A^7$ |
|---|---|---|---|---|
| 6 | — | 0 | — | — |
| 7 | — | 0 | — | — |
| 1 | — | 1 | — | CONH |
| 3 | — | 1 | — | CONH |
| 5 | — | 1 | — | CONH |
| 2 | — | 2 | — | CONH |
| 3 | — | 2 | — | CONH |
| 1 | — | 3 | — | CONH |
| 0 | — | 3 | — | CONH |
| 0 | — | 3 | — | CONH |
| 0 | — | 6 | — | CONH |
| 2 | — | 1 | — | O |
| 4 | — | 1 | — | O |
| 1 | — | 2 | — | O |
| 1 | — | 1 | — | NHCO |
| 3 | — | 1 | — | NHCO |
| 0 | — | 2 | — | NHCO |
| 2 | — | 2 | — | NHCO |
| 1 | — | 3 | — | NHCO |
| 3 | — | 3 | — | NHCO |
| 0 | — | 4 | — | NHCO |
| 0 | 1 | 2 | O | CONH |
| 2 | 1 | 2 | O | CONH |
| 0 | 1 | 3 | O | CONH |
| 0 | 2 | 1 | O | CONH |
| 0 | 1 | 1 | CONH | CONH |
| 0 | 1 | 1 | NHCO | CONH |
| 0 | 2 | 1 | CONH | O |
| 0 | 2 | 1 | O | O |
| 0 | 2 | 2 | O | O |
| 1 | 1 | 1 | NHCO | O |
| 0 | 1 | 2 | NHCO | O |
| 0 | 2 | 1 | O | NHCO |
| 1 | 1 | 1 | NHCO | NHCO |
| 0 | 2 | 1 | CONH | NHCO |
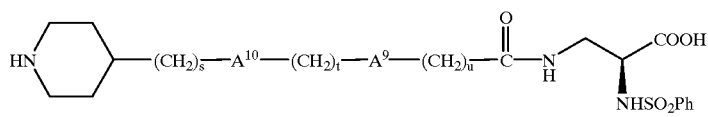
| s | t | u | $A^{10}$ | $A^9$ |
|---|---|---|---|---|
| 5 | — | — | — | — |
| 6 | — | — | — | — |
| 8 | — | — | — | — |
| 10 | — | — | — | — |
| 3 | — | 1 | — | CONH |
| 4 | — | 1 | — | CONH |
| 5 | — | 1 | — | CONH |
| 4 | — | 2 | — | CONH |
| 1 | — | 3 | — | CONH |
| 3 | — | 3 | — | CONH |
| 0 | — | 4 | — | CONH |
| 1 | — | 5 | — | CONH |
| 0 | — | 6 | — | CONH |
| 4 | — | 1 | — | O |
| 5 | — | 2 | — | O |
| 1 | — | 4 | — | O |
| 1 | — | 6 | — | O |
| 3 | — | 1 | — | NHCO |
| 3 | — | 1 | — | NHCO |
| 5 | — | 1 | — | NHCO |
| 0 | — | 4 | — | NHCO |
| 1 | — | 5 | — | NHCO |

-continued
| | | | | |
|---|---|---|---|---|
| 1 | 1 | 1 | O | CONH |
| 2 | 1 | 2 | O | CONH |
| 0 | 2 | 1 | O | CONH |
| 1 | 1 | 3 | O | CONH |
| 1 | 1 | 2 | CONH | CONH |
| 1 | 2 | 1 | NHCO | CONH |
| 0 | 2 | 1 | CONH | O |
| 1 | 2 | 1 | O | O |
| 0 | 2 | 2 | O | O |
| 1 | 1 | 1 | NHCO | O |
| 0 | 1 | 2 | NHCO | O |
| 0 | 2 | 1 | O | NHCO |
| 0 | 1 | 1 | NHCO | NHCO |
| 2 | 2 | 1 | CONH | NHCO |
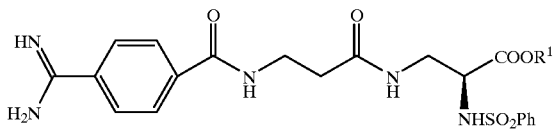
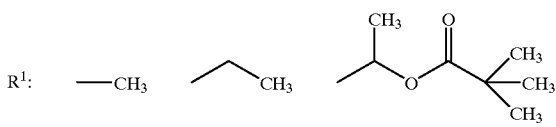
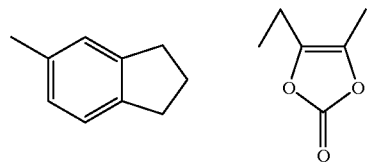
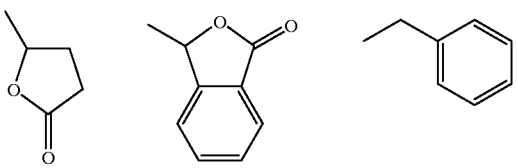
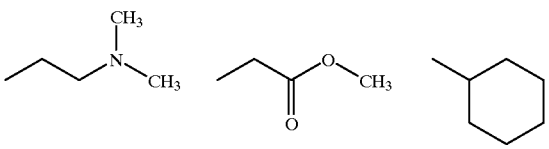
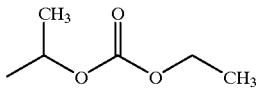
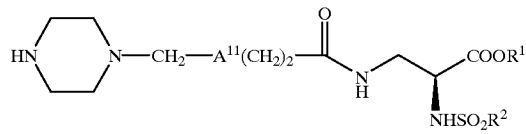
| $A^{11}$ | $R^1$ | $R^2$ |
|---|---|---|
| CH$_2$CONH | H | Ph |
| CONHCH$_2$ | Me | Et |
-continued
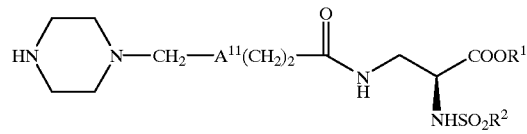
| $A^{11}$ | $R^1$ | $R^2$ |
|---|---|---|
| CH$_2$CONH | Et | p-MePh |

37

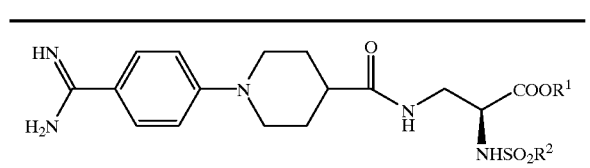

| R¹ | R₂ |
|---|---|
| H | Ph |
| Me | Et |
| Et | p-MePh |

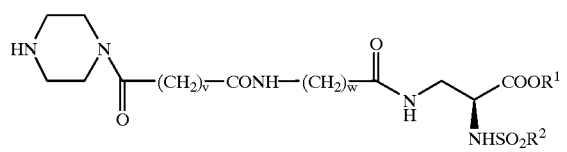

| v | w | R¹ | R² |
|---|---|---|---|
| 1 | 2 | H | Ph |
| 3 | 2 | Me | Et |
| 2 | 1 | Et | p-MePh |

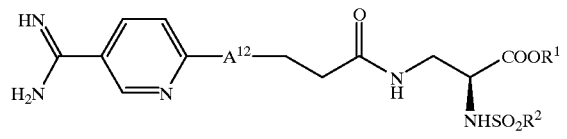

| $A^{12}$ | R¹ | R² |
|---|---|---|
| CONH | H | Ph |
| NHCO | Me | Et |
| CONH | Et | p-MePh |

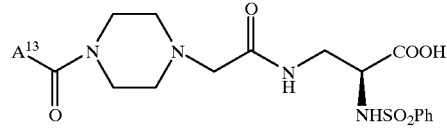

$A^{13}$

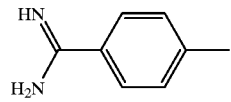

38

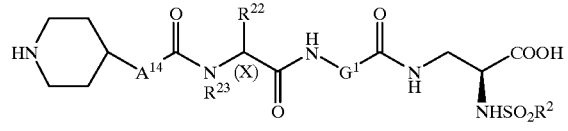

| $R^{23}$ | $R^{22}$ | $A^{14}$ | $G^1$ | X | $R^2$ |
|---|---|---|---|---|---|
| Et | i-Pr | $CH_2$ | $(CH_2)_2$ | S | Et |
| H | n-Butyl | — | $(CH_2)_3$ | S | p-MePh |
| Me | Bzl | $(CH_2)_2$ | $(CH_2)_2$ | S | Ph |
| Me | p-MeOBzl | $(CH_2)_2$ | $CH_2$ | R | Ph |

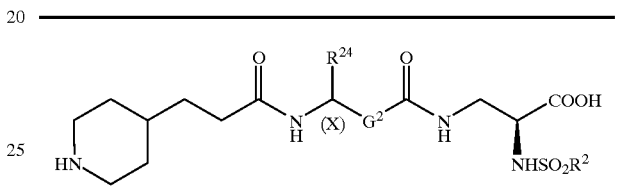

| $R^{24}$ | $G^2$ | X | $R^2$ |
|---|---|---|---|
| H | CHOH | S | Ph |
| Me | $CH_2$ | R | Et |
| i-Pr | CO | S | p-MePh |
| Bzl | CHOH | R | Ph |
| p-MeOBzl | CHOH | S | Ph |

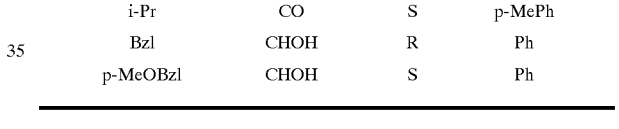

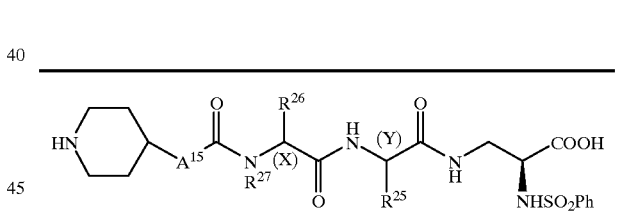

| $R^{27}$ | $R^{26}$ | $R^{25}$ | $A^{15}$ | X | Y |
|---|---|---|---|---|---|
| Me | Me | Me | $(CH_2)_2$ | S | R |
| Et | i-Pr | Bzl | $CH_2$ | S | S |
| H | n-Butyl | Bzl | — | R | S |
| Me | Bzl | Me | $(CH_2)_2$ | R | R |
| Me | p-MeOBzl | Me | $(CH_2)_2$ | S | S |

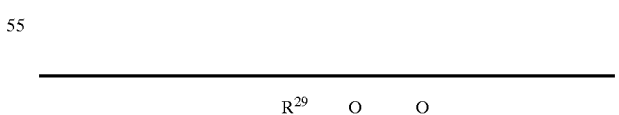

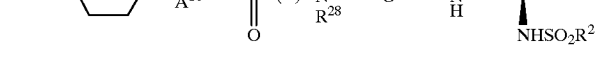

| $R^{30}$ | $R^{29}$ | $R^{28}$ | $A^{16}$ | $G^3$ | $R^2$ | X |
|---|---|---|---|---|---|---|
| H | Me | H | — | $CH_2$ | Ph | S |
| Et | i-Pr | H | $(CH_2)_2$ | $CH_2$ | Et | S |

39

-continued

| R$^{30}$ | R$^{29}$ | R$^{28}$ | A$^{16}$ | G$^3$ | R$^2$ | X |
|---|---|---|---|---|---|---|
| H | n-Butyl | Me | CH$_2$ | (CH$_2$)$_2$ | p-MePh | S |
| Me | Bzl | Me | (CH$_2$)$_2$ | (CH$_2$)$_2$ | Ph | R |
| H | p-MeOBzl | H | — | (CH$_2$)$_3$ | Ph | S |

| R$^{32}$ | R$^{31}$ | A$^{17}$ | E$^{15}$ | G$^4$ | X |
|---|---|---|---|---|---|
| Me | H | NH | CH$_2$ | CH$_2$ | R |
| i-Pr | H | CH$_2$NH | CHOH | CH$_2$ | S |
| n-Butyl | Me | NH | CO | (CH$_2$)$_2$ | R |
| Bzl | Me | (CH$_2$)$_2$NH | CH$_2$ | CH$_2$ | S |
| p-MeOBzl | H | NH | CHOH | (CH$_2$)$_3$ | S |

| G$^5$ | z | y | R$^2$ |
|---|---|---|---|
| CO | 2 | 3 | Ph |
| CO | 4 | 3 | Et |
| CHOH | 3 | 2 | p-MePh |
| CO | 5 | 2 | Ph |
| CHOH | 2 | 3 | Ph |

| A$^{18}$ | R$^1$ |
|---|---|
| — | H |
| CH$_2$ | Me |
| OCH$_2$ | Et |

40

| A$^{19}$ | R$^1$ | R$^2$ |
|---|---|---|
| CONH | Me | Ph |
| NHCO | Et | Et |
| (CH$_2$)$_2$ | H | p-MePh |
| OCH$_2$ | CH2OCOC(CH3)3 | Ph |
| (CH2)$_4$ | H | Ph |

| Y$^7$ | Y$^8$ | R$^1$ | R$^2$ |
|---|---|---|---|
| CH | N | H | Ph |
| N | N | Me | Et |
| N | CH | Et | p-MePh |

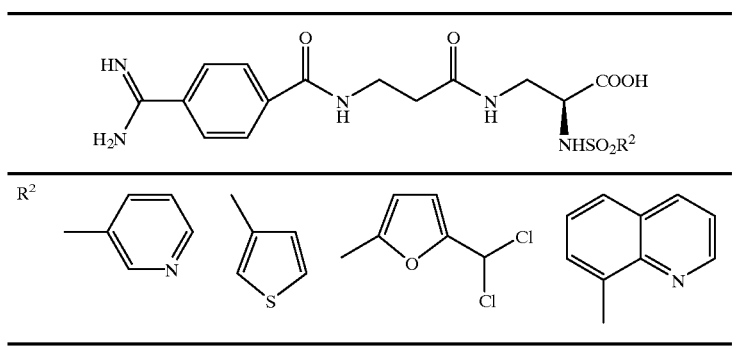
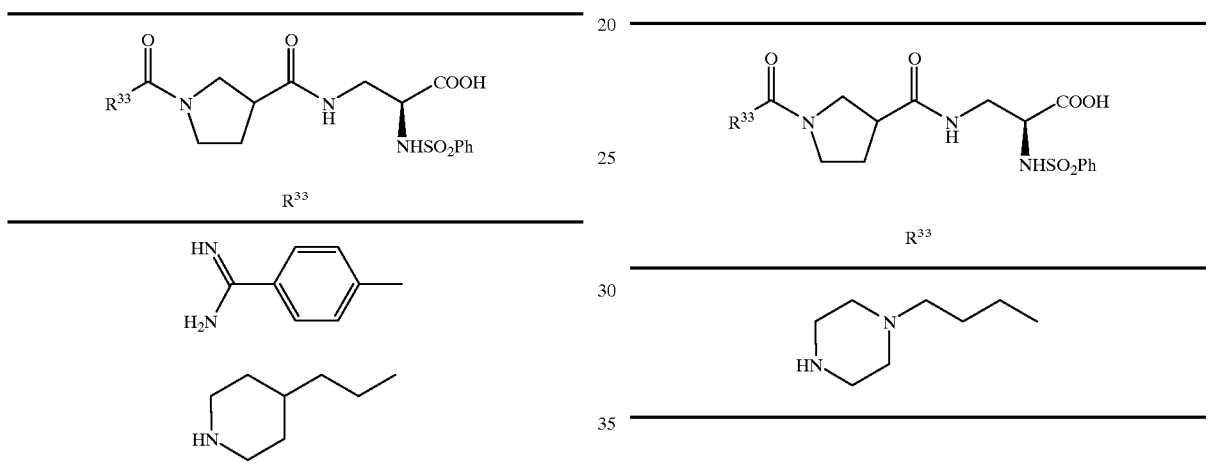
-continued
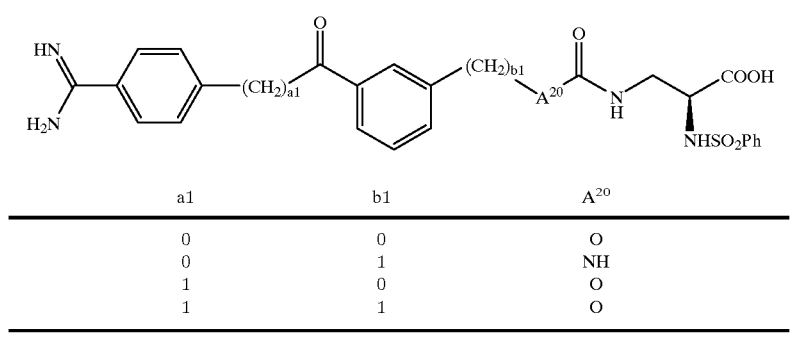
| a1 | b1 | A²⁰ |
|----|----|-----|
| 0  | 0  | O   |
| 0  | 1  | NH  |
| 1  | 0  | O   |
| 1  | 1  | O   |
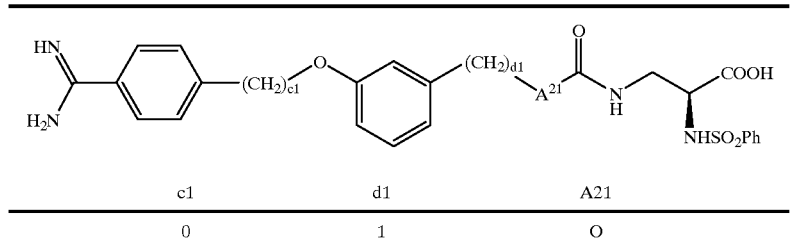
| c1 | d1 | A21 |
|----|----|-----|
| 0  | 1  | O   |

-continued

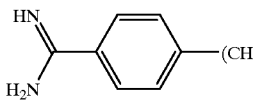

| c1 | d1 | A21 |
|---|---|---|
| 0 | 0 | NH |
| 1 | 0 | O |
| 1 | 1 | O |

Hereinbelow, the present invention is illustrated in more detail by Examples. The following abbreviations are used.

| Abbreviation | Name |
|---|---|
| DMF: | N,N-Dimethylformamide |
| HOBT·H$_2$O: | 1-Hydroxybenzotriazole hydrate |
| WSC·HCl: | 1-(3-Dimethylaminopropyl)-3-ethylcarbodiimide hydrochloride |
| TFA: | Trifluoroacetic acid |
| Z: | Benzyloxycarbonyl |
| Boc: | t-Butoxycarbonyl |
| (Boc)$_2$O: | di-t-Butyl dicarbonate |
| THF: | Tetrahydrofuran |
| BOP reagent: | Benzotriazolyl-N-hydroxytrisdimethylamino-phosphonium hexafluorophosphide salt |

Example 1

Synthesis of (2S)-3-(3-(4-amidinobenzoylamino) propanoylamino)-2-benzenesulfonylaminopropanoic Acid TFA Salt (1) (2S)-3-Amino-2-benzyloxycarbonylaminopropanoic acid N-Z-Asparagine (3.124 g) is dissolved in a mixture of DMF (30 ml) and water (30 ml), and thereto is added bis(trifluoroacetyl)iodobenzene (7.575 g) at room temperature, and the mixture is stirred for 15 minutes. To the mixture is added pyridine (1.874 ml) at room temperature, and the mixture is stirred for four hours. The mixture is evaporated under reduced pressure to remove the solvent, and water (150 ml) is added to the residue. The mixture is washed twice with ether, and the aqueous layer is concentrated under reduced pressure. The residue is crystallized from ethanol-ether to give the title compound (2.149 g).

(2) (2S)-2-Benzyloxycarbonylamino-3-(t-butoxycarbonylamino)propanoic Acid

The product (0.61 g) obtained in the above (1) is dissolved in a mixture of 1,4-dioxane (6 ml) and water (2 ml), and thereto is added (Boc)$_2$O (0.62 g) at room temperature, and the mixture is stirred for 1.5 hour. To the mixture is added 1N aqueous sodium hydroxide solution (4 ml), and washed twice with ether. The pH value of the aqueous layer is adjusted to pH 2 with 1N hydrochloric acid, and the mixture is extracted three times with ethyl acetate. The organic layer is washed twice with a saturated brine, and dried over anhydrous magnesium sulfate. The desiccant is removed by filtration, and the filtrate is concentrated under reduced pressure to give the title compound (0.867 g).

(3) (2S)-2-Benzyloxycarbonylamino-3-(t-butoxycarbonylamino)propanoic Acid Methyl Ester The product (0.867 g) obtained in the above (2) is dissolved in dichloromethane (15 ml), and thereto are added methanol (1.5 ml), 4-dimethylaminopyridine (34 mg) and WSC·HCl (0.633 g) under ice-cooling. The mixture is stirred under ice-cooling for two hours, and then stirred at room temperature for 12 hours. The mixture is concentrated under reduced pressure to the volume of about 5 ml, and the residue is poured into water.

The mixture is extracted three time with ethyl acetate, and the organic layer is washed 1N HCl (twice), a saturated aqueous sodium hydrogen carbonate solution (twice), and with a saturated brine (twice), and then dried over anhydrous magnesium sulfate. The desiccant is removed by filtration, and the filtrate is concentrated under reduced pressure to give the title compound (0.875 g).

$^1$H-NMR (CDCl$_3$) δ (ppm): 1.42 (9H, s), 3.55 (2H, m), 3.76 (3H, s), 4.42 (1H, m), 4.85 (1H, m), 5.12 (2H, s), 5.80 (1H, m), 7.35 (5H, bs)

(4) (2S)-2-Benzyloxycarbonylamino-3-(3-(t-butoxycarbonylamino)propanoylamino)propanoic Acid Methyl Ester The product (6.0 g) obtained in the above (3) is dissolved in acetonitrile (10 ml), and thereto is added dropwise a solution of methanesulfonic acid (8.181 g) in acetonitrile (15 ml) at a temperature below 20° C., and the mixture is stirred at room temperature for 30 minutes. At a temperature below 20° C., to the mixture are added dropwise DMF (20 ml), triethylamine (8.608 g) successively, and the mixture is stirred for 10 minutes. To the mixture are added N-Boc-β-alanine (3.547 g) and HOBT·H$_2$O (3.13 g), and then further added thereto WSC·HCl (3.928 g) at a temperature of from 5 to 10° C., and the mixture is stirred for 30 minutes. The mixture is further stirred at room temperature for 12 hours, and poured into water, and extracted three time with ethyl acetate. The organic layer is washed successively with 1N HCl (twice), a saturated aqueous sodium hydrogen carbonate solution (twice) and a saturated brine (twice), and dried over anhydrous magnesium sulfate. The desiccant is removed by filtration, and the filtrate is concentrated under reduced pressure. The residue is purified by silica gel column chromatography (silica gel; 400 g, solvent; chloroform/acetone=3:1 to 2:1). The fractions containing the title compound are concentrated under reduced pressure to give the title compound (6.974 g).

$^1$H-NMR (CDCl$_3$) δ (ppm): 1.40 (9H, s), 2.33 (2H, t, J=6 Hz), 3.35 (2H, m), 3.67 (2H, m), 3.78 (3H, s), 4.45 (1H, m), 5.10 (2H, s), 5.20 (1H, m), 5.90 (1H, m), 6.25 (1H, m), 7.30 (5H, bs)

(5) (2S)-2-Benzenesulfonylamino-3-(3-(t-butoxycarbonylamino)propanoylamino)propanoic Acid Methyl Ester The product (6.77 g) obtained in the above (4) is dissolved in a mixture of ethanol (50 ml) and ethyl acetate (30 ml), and thereto is added 10% palladium-carbon (50% wet) (5 g). The mixture is stirred at room temperature for 2.5 hours under hydrogen atmosphere. The insoluble materials are removed by filtration, and the filtrate is concentrated under reduced pressure.

The residue is dissolved in dichloromethane (20 ml), and thereto are added triethylamine (5.36 ml) and benzenesulfonyl chloride (3.69 ml) at room temperature, and the mixture is stirred for 10 minutes. To the mixture are added triethylamine (5.36 ml) and benzenesulfonyl chloride (3.69 ml), and the mixture is further stirred for 20 minutes. The mixture is evaporated under reduced pressure to remove the solvent, and thereto is added ethyl acetate. The mixture is washed successively with 1N hydrochloric acid (twice), a saturated brine (once), a saturated aqueous sodium hydrogen carbonate solution (twice), and a saturated brine (twice), and dried over anhydrous magnesium sulfate. The desiccant is removed by filtration, and the filtrate is concentrated under reduced pressure. The residue is purified by silica gel column chromatography (silica gel; 400 g, solvent; chloroform-methanol=30:1 (2 liters) to 10:1 (1.5 liter)). The fractions containing the title compound are concentrated under reduced pressure to give the title compound (5.199 g).

$^1$H-NMR (CDCl$_3$) δ (ppm): 1.44 (9H, s), 2.38 (2H, t, J=6 Hz), 3.40 (2H, m), 3.56 (3H, s), 3.60 (2H, m), 4.06 (1H, m), 5.27 (1H, m), 6.10 (1H, m), 6.57 (1H, m), 7.45–7.65 (3H, m), 7.86 (2H, d, J=7 Hz)

(6) 4-Amidinobenzoic Acid Hydrochloride

4-Amidinobenzamide (commercially available one, 7.8 g) is dissolved in water (200 ml), and thereto is added conc. hydrochloric acid (200 ml), and the mixture is stirred at a temperature below 100° C. for 9 hours. The mixture is cooled, and the precipitated crystals are collected by filtration.

Yield: 7.6 g

MS (SIMS): 165 [M+1]$^+$ $^1$H-NMR (CD$_3$OD) δ (ppm): 7.94 (2H, d, J=8.6 Hz), 8.26 (2H, d, J=8.6 Hz)

(7) N-t-Butoxycarbonyl-4-amidinobenzoic Acid

The product (1.772 g) obtained in the above (6) is suspended in dichloromethane (35 ml), and thereto is added N,O-bistrimethylsilylacetamide (7.2 g), and the mixture is stirred at room temperature for one hour. To the mixture is added (Boc)$_2$O (3.9 g) at room temperature, and the mixture is stirred for 24 hours. The insoluble materials are removed by filtration, and the filtrate is concentrated under reduced pressure. To the residue is added diethyl ether, and the mixture is stirred. The precipitated crystals are collected by filtration.

Yield: 2.334 g $^1$H-NMR (DMSO-d$_6$) δ (ppm): 1.55, 1.75 (9H, s), 7.88 (2H, m), 8.09 (2H, m), 6.11–6.77, 7.22–7.40 (1H, m), 9.40, 9.58, 10.48–10.68 (1H, m)

(8) (2S)-2-Benzenesulfonylamino-3-(3-(4-(N-t-butoxycarbonylamidino)benzoylamino)propanoylamino) propanoic Acid Methyl Ester The product (0.388 g) obtained in the above (5) is dissolved in acetonitrile (2 ml), and thereto is added dropwise a solution of methanesulfonic acid (0.434 g) in acetonitrile (2 ml) at a temperature below 20° C., and the mixture is stirred at room temperature for 30 minutes. To the mixture are added dropwise DMF (10 ml) and a solution of triethylamine (0.457 g) in DMF (1.5 ml) at a temperature below 20° C., and the mixture is stirred for 10 minutes. To the mixture are added the product (0.263 g) obtained in the above (7) and HOBT.H$_2$O (0.167 g). WSC.HCl (0.209 g) is added to the mixture at a temperature of from 5 to 10° C., and the mixture is stirred for 30 minutes. The mixture is further stirred at room temperature for 39 hours, during which triethylamine (18 mg) and WSC.HCl (87 mg) are added thereto at 15 hours thereafter, and 21 hours thereafter, respectively. The reaction mixture is poured into water, and extracted five times with ethyl acetate. The organic layer is washed successively with 1N HCl (twice), a saturated aqueous sodium hydrogen carbonate solution (twice) and a saturated brine (twice), and dried over anhydrous magnesium sulfate. The desiccant is removed by filtration, and the filtrate is concentrated under reduced pressure, and the residue is purified by silica gel column chromatography (silica gel; 50 g, solvent; chloroform-methanol=10:1). The fractions containing the title compound are concentrated under reduced pressure to give the title compound (0.385 g).

MS (SIMS): 576 [M+1]$^+$ $^1$H-NMR (CDCl$_3$) δ (ppm): 1.53 (9H, s), 2.50 (2H, m), 3.50 (3H, s), 3.50–3.90 (4H, m), 4.10 (1H, m), 7.40–7.70 (4H, m), 7.75–8.03 (9H, m)

(9) (2S)-3-(3-(4-Amidinobenzoylamino)propanoylamino)-2-benzenesulfonylaminopropanic Acid TFA Salt The product (0.385 g) obtained in the above (8) is dissolved in TFA (5 ml) under ice-cooling, and the mixture is stirred for 30 minutes, and then stirred at room temperature for one hour. The TFA is distilled off, and a mixture of acetic acid (2 ml) and water (8 ml) is added to the residue, and the mixture is refluxed for 11 hours. The reaction mixture is concentrated under reduced pressure, and the residue is purified by HPLC to give the desired compound (97 mg) as a white powder.

MS (SIMS): 462 [M+1]$^+$

HPLC retention time: 15.7 minutes (Column: YMC-ODS 4.6 mmØ×250 mm, Detection: UV220 nm, Eluent; A solution: 0.1% TFA/water, B solution: 0.1% TFA/acetonitrile, Flow rate; 1 ml/min., Gradient; the concentration of B solution is increased from 10% at a rate of 1%/min.)

$^1$H-NMR (DMSO-d$_6$) δ (ppm): 2.31 (2H, m), 3.05–3.60 (4H, m), 3.90 (1H, m), 7.58 (3H, m), 7.77 (2H, d, J=8 Hz), 7.87 (2H, d, J=8.5 Hz), 8.01 (2H, d, J=8.5 Hz), 7.95–8.20 (2H, m), 8.71 (1H, t, J=6 Hz), 9.29, 9.38 (4H, bs)

Example 2

Synthesis of (2S)-2-benzenesulfonylamino-3-(3-(3-(4-piperidyl)propanoylamino)propanoylamino) propanoic Acid TFA Salt (1) (1-t-Butoxycarbonyl-4-piperidyl)methanol Isonipeconic acid (20 g) is dissolved in a mixture of 1,4-dioxane (150 ml) and 1N NaOH (170 ml), and thereto is added (Boc)$_2$O (37.1 g) at a room temperature, and the mixture is stirred for 24 hours. The pH value of the mixture is adjusted to pH 2 with 1N hydrochloric acid, and extracted three times with ethyl acetate. The organic layer is washed twice with a saturated brine, and then dried over anhydrous magnesium sulfate. The desiccant is removed by filtration, and the filtrate is concentrated under reduced pressure to give a Boc compound (33.9 g).

The Boc compound (20.0 g) is dissolved in dichloremethane (400 ml), and thereto are added triethylamine (9.7 g), N-hydroxysuccinimide (11.0 g) and WSC.HCl (18.4 g), and the mixture is stirred at room temperature for three hours. The reaction mixture is diluted with dichloromethane, washed twice with water, and dried over anhydrous magnesium sulfate. The desiccant is removed by filtration, and the filtrate is concentrated under reduced pressure to give a white solid (29.0 g).

To a solution of the white solid (25.6 g) in tetrahydrofuran (400 ml) is added sodium borohydride (7.42 g). The mixture is stirred at room temperature for 2.5 hours, and stirred at 50° C. for 15 minutes. The reaction solution is allowed to cool, and thereto is added 10% aqueous ammonium chloride solution (200 ml), and the mixture is extracted three times with ethyl. acetate. The extract is washed with water and a saturated brine, and dried over anhydrous magnesium sulfate. The desiccant is removed by filtration, and the filtrate is concentrated under reduced pressure. The residue is purified by silica gel column chromatography (silica gel; 500 g, solvent; hexane-ethyl acetate=1:1). The fractions containing the title compound are concentrated under reduced pressure to give a white solid (13.0 g).

(2) (1-t-Butoxycarbonyl-4-piperidine)carboxyaldehyde

To a solution of dimethylsulfoxide (2.2 ml) in dichloromethane (30 ml) is added oxalyl chloride (2.05 ml) at −78° C., and the mixture is stirred for five minutes. To the mixture is added dropwise a solution of the product (2.0 g) obtained in the above (1) in dichloromethane (10 ml), and the mixture is further stirred for 15 minutes. Triethylamine (5.2 ml) is added to the mixture, and the mixture is warmed to room temperature, and stirred for 30 minutes. To the reaction solution is added water, and the mixture is extracted three times with ethyl acetate. The organic layer is washed successively with 1N hydrochloric acid (twice), a saturated brine (once), a saturated aqueous sodium hydrogen carbonate solution (twice) and a saturated brine (twice), and dried over anhydrous magnesium sulfate. The desiccant is removed by filtration, and the filtrate is concentrated under reduced pressure to give the title compound (1.98 g).

(3) 3-(1-t-Butoxycarbony-4-piperidyl)propanoic Acid

To a solution of ethyl diethyl phosphonoacetate (2.50 g) in THF (10 ml) is added 60% NaH (410 mg) in portions at a temperature below 40° C. under nitrogen atmosphere, and the mixture is stirred for 10 minutes. To the mixture is added dropwise a solution of the compound (1.98 g) obtained in the above (2) in THF (10 ml) at a temperature below 35° C., and the mixture is stirred at room temperature for two hours. To the reaction solution is added water, and the mixture is extracted three times with ethyl acetate. The extract is washed successively with 1N hydrochloric acid (twice), a saturated brine (once), a saturated aqueous sodium hydrogen carbonate solution (twice) and a saturated brine (twice), and dried over anhydrous magnesium sulfate. The desiccant is removed by filtration, and the filtrate is concentrated under reduced pressure. The residue is purified by silica gel column chromatography (silica gel; 100 g, solvent; hexane-ethyl acetate=4:1). The fractions containing the desired compound are concentrated under reduced pressure to give an ester compound (2.43 g) as an oily product.

The ester compound (2.43 g) is dissolved in ethanol (15 ml), and thereto is added 10% palladium-carbon (50% wet, 1.54 g). The mixture is stirred at room temperature for three hours under hydrogen atmosphere. The insoluble materials are removed by filtration, and the filtrate is concentrated under reduced pressure. The residue is dissolved in methanol (20 ml), and thereto is added 1N NaOH (13 ml), and the mixture is stirred at room temperature for three hours. The mixture is evaporated under reduced pressure to remove the methanol, and the pH value thereof is adjusted to pH 2 with 1N HCl, and the mixture is extracted three times with ethyl acetate. The extract is washed twice with a saturated brine, and dried over anhydrous magnesium sulfate. The desiccant is removed by filtration, and the filtrate is concentrated under reduced pressure to give a white solid (1.90 g).

$^1$H-NMR (CDCl$_3$) δ (ppm): 1.00–1.20 (2H, m), 1.45 (9H, s), 1.55–1.72 (5H, m), 2.39 (2H, t, J=7 Hz), 2.67 (2H, t, J=13 Hz), 4.00–4.20 (2H, m)

(4) (2S)-2-Benzyloxycarbonylamino-3-(3-(3-(1-t-butoxycarbonyl-4-piperidyl)propanoylamino)propanoylamino)propanoic Acid Methyl Ester The compound (0.2 g) obtained in Example 1-(4) is dissolved in acetonitrile (2.5 ml), and thereto is added dropwise a solution of methanesulfonic acid (0.227 g) in acetonitrile (1.5 ml) at a temperature below 20° C., and the mixture is stirred at room temperature for 30 minutes. To the mixture are added dropwise DMF (4 ml) and triethylamine (0.239 g) at a temperature below 20° C., and the mixture is stirred for 10 minutes. To the mixture are added the product (0.134 g) obtained in the above (3), HOBT.H$_2$O (87 mg), and then further thereto is added WSC.HCl (0.109 g) at a temperature of from 5 to 10° C. The mixture is stirred for 30 minutes, and further stirred at room temperature for 12 hours. The mixture is poured into water, and the mixture is extracted three times with ethyl acetate. The organic layer is washed successively with 1N HCl (twice), a saturated aqueous sodium hydrogen carbonate solution (twice), a saturated brine (twice), and dried over anhydrous magnesium sulfate. The desiccant is removed by filtration, and the filtrate is concentrated under reduced pressure. The residue is purified by silica gel column chromatography (silica gel; 30 g, solvent; chloroform-acetone=1:1). The fractions containing the title compound are concentrated under reduced pressure to give the title compound (0.272 g).

$^1$H-NMR (CDCl$_3$) δ (ppm): 0.95–1.15 (2H, m), 1.45 (9H, s), 1.30–1.85 (5H, m), 2.11–2.22 (2H, m), 2.25–2.40 (2H, m), 2.63 (2H, dd, J=12, 12 Hz), 3.37–3.80 (4H, m), 3.76 (3H, s), 3.95–4.15 (2H, m), 4.38–4.50 (1H, m), 5.10 (2H, s), 5.85–5.95 (1H, m), 6.32 (1H, m), 6.38–6.50 (1H, m), 7.35 (5H, s)

(5) (2S)-2-Amino-3-(3-(3-(1-t-butoxycarbonyl-4-piperidyl)propanoylamino)propanoylamino)propanoic Acid Methyl Ester The compound (0.578 g) obtained in the above (4) is dissolved in ethanol (15 ml), and thereto is added 10% palladium-carbon (50% wet, 0.4 g), and the mixture is stirred at room temperature for four hours under hydrogen atmosphere. The insoluble materials are removed by filtration, and the filtrate is concentrated under reduced pressure to give the title compound (398 mg).

(6) (2S)-2-Benzenesulfonylamino-3-(3-(3-(1-t-butoxycarbonyl-4-piperidyl)propanoylamino)propanoylamino)propanoic Acid Methyl Ester The compound (120 mg) obtained in the above (5) is dissolved in dichloromethane (3 ml), and thereto are added triethylamine (98 μl) and benzenesulfonyl chloride (54 μl) at room temperature, and the mixture is stirred for 30 minutes. Triethylamine (98 μl) and benzenesulfonyl chloride (81 μl) are further added, and the mixture is stirred for 90 minutes. The mixture is evaporated under reduced pressure to remove the solvent, and to the residue is added ethyl acetate. The mixture is washed successively with 1N hydrochloric acid (twice), a saturated brine (once), a saturated aqueous sodium hydrogen carbonate solution (twice) and a saturated brine (twice), and dried over anhydrous magnesium sulfate. The desiccant is removed by filtration, and the filtrate is concentrated under reduced pressure. The residue is purified by silica gel column chromatography (silica gel; 20 g, solvent; chloroform-methanol=30:1 to 10:1). The fractions containing the title compound are concentrated under reduced pressure to give the title compound (151 mg).

$^1$H-NMR (CDCl$_3$) δ (ppm): 0.98–1.17 (2H, m), 1.44 (9H, s), 1.30–1.70 (5H, m), 2.10–2.58 (4H, m), 2.65 (2H, dd, J=12, 12 Hz), 3.45–3.75 (4H, m), 3.52 (3H, s), 3.96–4.20 (3H, m), 6.28–6.37 (1H, m), 6.56–6.76 (1H, m), 6.98–7.08 (1H, m), 7.46–7.62 (3H, m), 7.80–7.88 (2H, m)

(7) (2S)-2-Benzenesulfonylamino-3-(3-(3-(4-piperidyl)propanoylamino)propanoylamino)propanoic Acid TFA Salt The compound (151 mg) obtained in the above (6) is dissolved in a mixture of methanol (4 ml) and THF (4 ml), and thereto is added 1N aqueous lithium hydroxide solution (4 ml). The mixture is stirred at room temperature for three hours, and evaporated under reduced pressure to remove the solvent. The pH value of the residue is adjusted to pH 2 with 1N HCl, and extracted three times with ethyl acetate. The extract is washed twice with a saturated brine, and dried over anhydrous magnesium sulfate. The desiccant is removed by filtration, and the filtrate is concentrated under reduced pressure. The residue is dissolved in TFA (5 ml) under ice-cooling, and stirred for one hour. The reaction mixture is concentrated under reduced pressure, and the residue is purified by HPLC to give a white powder (113 mg).

MS (SIMS): 455 [M+1]$^+$

HPLC retention time: 14.3 min.

(Column: YMC-ODS 4.6 mmØ×250 mm, Detection: UV220 nm, Eluent; A solution: 0.1% TFA/water, B solution: 0.1% TFA/acetonitrile, Flow rate; 1 ml/min., Gradient; the concentration of B solution is increased from 10% at a rate of 1%/min.)

$^1$H-NMR (DMSO-$d_6$) δ (ppm): 1.21 (2H, m), 1.45 (3H, m), 1.77 (2H, m), 2.00–2.20 (4H, m), 2.82 (2H, m), 3.03–3.35 (6H, m), 3.88 (1H, m), 7.58 (3H, m), 7.80 (3H, m), 7.97 (1H, t, J=5.5 Hz), 8.11 (1H, d, J=9 Hz), 8.22 (1H, bs), 8.55 (1H, bs)

Example 3

Synthesis of (2S)-2-butanesulfonylamino-3-(3-(3-(4-piperidyl)propanoylamino)propanoylamino) propanoic Acid TFA Salt (1) (2S)-2-Butanesulfonylamino-3-(3-(3-(1-t-butoxycarbonyl-4-piperidyl)propanoylamino)propanoylamino)propanoic Acid Methyl Ester The compound (0.272 g) obtained in Example 2-(5) is dissolved in ethyl acetate (10 ml), and thereto are added sodium hydrogen carbonate (295 mg) and 1-butanesulfonyl chloride (91 μl) at room temperature, and the mixture is refluxed for 8 hours. The mixture is evaporated under reduced pressure to remove the solvent, and to the residue is added ethyl acetate. The mixture is washed successively with 1N hydrochloric acid (twice), a saturated brine (once), a saturated aqueous sodium hydrogen carbonate solution (twice) and a saturated brine (twice), and dried over anhydrous magnesium sulfate. The desiccant is removed by filtration, and the filtrate is concentrated under reduced pressure to give the title compound (192 mg).

$^1$H-NMR (CDCl$_3$) δ (ppm): 0.90–1.18 (7H, m), 1.45 (9H, s), 1.30–2.11 (7H, m), 2.20–2.30 (2H, m), 2.33–2.55 (2H, m), 2.66 (2H, dd, J=12, 12 Hz), 3.04 (2H, dd, J=8 Hz), 3.44–3.70 (4H, m), 3.79 (3H, s), 4.06 (2H, d, J=12 Hz), 4.30 (1H, m), 6.03 (1H, m), 6.78 (1H, m), 7.09 (1H, m)

(2) (2S)-2-Butanesulfonylamino-3-(3-(3-(4-piperidyl)propanoylamino)propanoylamino)propanoic Acid TFA Salt The compound (192 mg) obtained in the above (1) is dissolved in a mixture of methanol (6 ml) and THF (3 ml), and thereto is added 4N aqueous lithium hydroxide solution (1.75 ml), and the mixture is stirred at room temperature for one hour. The mixture is evaporated under reduced pressure, and the pH value of the residue is adjusted to pH 2 with 1N HCl and extracted three times with ethyl acetate. The extract is washed twice with a saturated brine, and dried over anhydrous magnesium sulfate. The desiccant is removed by filtration, and the filtrate is concentrated under reduced pressure. The residue is dissolved in TFA (5 ml) under ice-cooling, and the mixture is stirred for one hour. The reaction mixture is concentrated under reduced pressure. The residue is purified by HPLC to give a white powder (108 mg).

MS (SIMS): 435 [M+1]$^+$

HPLC retention time: 13.3 min.

(Column: YMC-ODS 4.6 mmØ×250 mm, Detection: UV220 nm, Eluent; A solution: 0.1% TFA/water, B solution: 0.1% TFA/acetonitrile, Flow rate; 1 ml/min., Gradient; the concentration of B solution is increased from 10% at a rate of 1%/min.)

$^1$H-NMR (DMSO-$d_6$) δ (ppm): 0.87 (3H, t, J=7 Hz), 1.10–1.58 (7H, m), 1.65 (2H, m), 1.78 (2H, m), 2.06 (2H, t, J=7 Hz), 2.23 (2H, t, J=7 Hz), 2.83 (2H, m), 2.97 (2H, t, J=6 Hz), 3.10–3.50 (6H, m), 3.98 (1H, m), 7.52 (1H, d, J=9 Hz), 7.75 (1H, t, J=5 Hz), 8.03 (1H, t, J=5 Hz), 8.20 (1H, bs), 8.50 (1H, bs)

Example 4

(2S)-2-Benzyloxycarbonylamino-3-(3-(3-(4-piperidyl)propanoylamino)propanoylamino) propanoic Acid TFA Salt The compound (0.12 g) obtained in Example 2-(4) is dissolved in a mixture of methanol (3 ml) and THF (2 ml), and thereto is added 2N aqueous lithium hydroxide solution (2 ml), and the mixture is stirred at room temperature for one hour. The mixture is evaporated under reduced pressure to remove the solvent, and the pH value thereof is adjusted to pH 2 with 1N HCl, and the mixture is extracted three time with ethyl acetate. The extract is washed twice with a saturated brine, and dried over anhydrous magnesium sulfate. The desiccant is removed by filtration, and the filtrate is concentrated under reduced pressure. The residue is dissolved in 4N HCl in 1,4-dioxane (5 ml) under ice-cooling, and the mixture is stirred for one hour. The reaction mixture is concentrated under reduced pressure, and the residue is purified by HPLC to give a white powder (104 mg).

MS (SIMS): 449 [M+1]$^+$

HPLC retention time: 18.9 min.

(Column: YMC-ODS 4.6 mmØ×250 mm, Detection: UV220 nm, Eluent; A solution: 0.1% TFA/water, B solution: 0.1% TFA/acetonitrile, Flow rate; 1 ml/min., Gradient; the concentration of B solution is increased from 10% at a rate of 1%/min.)

$^1$H-NMR (DMSO-$d_6$) δ (ppm): 1.20 (2H, m), 1.43 (3H, m), 1.78 (2H, m), 2.05 (2H, t, J=7 Hz), 2.22 (2H, t, J=7 Hz), 2.81 (2H, m), 3.15–3.70 (6H, m), 4.11 (1H, m), 5.03 (2H, s), 7.36 (5H, bs), 7.50 (1H, d, J=8 Hz), 7.78 (1H, m), 8.02 (1H, m), 8.15 (1H, bs), 8.50 (1H, bs)

Example 5

Synthesis of (2S)-2-butanesulfonylamino-3-(N-(4-(4-piperidyl)butanoyl)glycylamino)propanoic Acid TFA Salt (1) 4-(1-t-Butoxycarbonyl-4-piperidyl)butanoic Acid 4-Piperidinone hydrochloride (10 g) is dissolved in a mixture of 1,4-dioxane (100 ml) and aqueous sodium hydroxide solution (NaOH 5.7 g, water 50 ml), and thereto is added (Boc)$_2$O (16.1 g) under ice-cooling, and the mixture is stirred for two hours. The reaction mixture is diluted with ethyl acetate, and the organic layer is washed successively each twice with 10% aqueous citric acid solution, a saturated aqueous sodium hydrogen carbonate solution and a saturated brine, and dried over anhydrous magnesium sulfate. The desiccant is removed by filtration, and the filtrate is concentrated under reduced pressure. To the residue is added hexane, and the precipitates are collected by filtration to give 1-t-butoxycarbonyl-4-piperidinone (7.55 g).

To a solution of ethyl 4-diethylphosphonochrotonate (8.41 g) in THF (30 ml) is added dropwise a 1.6M butyl lithium in hexane solution (7.4 ml) at a temperature below −50° C., and the mixture is stirred at −78° C. for 1 5 minutes. A solution of the above 1-t-butoxycarbonyl-4-piperidinone (5.0 g) in THF (25 ml) is added dropwise, and the mixture is stirred at −78° C. for 20 minutes, and stirred at −10° C. for two hours. Water is added to the reaction mixture, and the mixture is extracted three times with ethyl acetate. The extract is washed successively with 1N hydrochloric acid (twice), a saturated brine (once), a saturated aqueous sodium hydrogen carbonate solution (twice) and a saturated brine (twice), and dried over anhydrous magnesium sulfate. The desiccant is removed by filtration, and the filtrate is concentrated under reduced pressure to give an ester compound (7.70 g) as a white solid.

The ester compound (7.70 g) is dissolved in a mixture of ethanol (40 ml) and ethyl acetate (20 ml), and thereto is added 10% palladium-carbon (50% wet, 0.96 g), and the mixture is stirred at room temperature for 6 hours under hydrogen atmosphere. The insoluble materials are removed by filtration, and the filtrate is concentrated under reduced pressure to give a white solid (7.76 g).

The white solid thus obtained (1.00 g) is dissolved in methanol (15 ml), and thereto is added aqueous sodium hydroxide solution (NaOH 0.7 g, water 2 ml), and the mixture is stirred at room temperature for one hour. The mixture is evaporated under reduced pressure to remove the methanol, and the pH value of the residue is adjusted to pH 2 with 1N HCl, and extracted three times with ethyl acetate. The extract is washed twice with a saturate brine, and dried over anhydrous magnesium sulfate. The desiccant is removed by filtration, and the filtrate is concentrated under reduced pressure to give the title compound (0.91 g) as a white solid.

$^1$H-NMR (CDCl$_3$) δ (ppm): 1.10 (2H, m), 1.45 (9H, s), 1.20–1.75 (7H, m), 2.35 (2H, t, J=7.6 Hz), 2.67 (2H, dd, J=12 Hz), 4.07 (2H, m)

(2) (2S)-2-Benzyloxycarbonylamino-3-(N-t-butoxycarbonylglycylamino)propanoic Acid Methyl Ester The compound (100 mg) obtained in Example 1-(3) is dissolved in acetonitrile (2 ml), and thereto is added dropwise a solution of methanesulfonic acid (218 mg) in acetonitrile (2.5 ml) at a temperature below 20° C., and the mixture is stirred at room temperature for 30 minutes. To the mixture are added successively DMF (4 ml) and triethylamine (317 μl) under ice-cooling, and the mixture is stirred for 10 minutes. Boc-glycine (56 mg) and HOBT.H$_2$O (53 mg) are added, and thereto is further added WSC.HCl (66 mg), and the mixture is stirred for 30 minutes. The mixture is further stirred at room temperature for four hours, and poured into water, and extracted three times with ethyl acetate. The organic layer is washed successively with 1N HCl (twice), a saturated aqueous sodium hydrogen carbonate solution (twice) and a saturated brine (twice), and dried over anhydrous magnesium sulfate. The desiccant is removed by filtration, and the filtrate is concentrated under reduced pressure to give the title compound (130 mg) as an oily product.

(3) (2S)-2-Benzyloxycarbonylamino-3-(N-(4-(1-t-butoxycarbonyl-4-piperidyl)butanoyl)glycylamino) propanoic Acid Methyl Ester The compound (130 mg) obtained in the above (2) is dissolved in acetonitrile (2.5 ml) and thereto is added dropwise a solution of methanesulfonic acid (244 mg) in acetonitrile (0.5 ml) at a temperature below 20° C., and the mixture is stirred at room temperature for 30 minutes. To the mixture are added dropwise DMF (5 ml) and triethylamine (354 mg) successively under ice-cooling, and the mixture is stirred for 10 minutes. To the mixture added the compound (95 mg) obtained in the above (1), HOBT.H$_2$O (59 mg), and further thereto is added WSC.HCl (74 mg), and the mixture is stirred for 30 minutes. The mixture is further stirred at room temperature for 12 hours, poured into water, and extracted three times with ethyl acetate. The organic layer is washed successively with 1N HCl (twice), a saturated aqueous sodium hydrogen carbonate solution (twice) and a saturated brine (twice), and dried over anhydrous magnesium sulfate. The desiccant is removed by filtration, and the filtrate is concentrated under reduced pressure. The residue is purified by silica gel column chromatography (silica gel; 20 g, solvent; chloroform-acetone=2:1). The fractions containing the title compound are concentrated under reduced pressure to give the title compound (79 mg).

$^1$H-NMR (CDCl$_3$) δ (ppm): 0.95–1.80 (9H, m), 1.45 (9H, s), 2.20 (2H, m), 2.65 (2H, m), 3.67 (2H, m), 3.75 (3H, s), 3.85 (2H, d, J=5 Hz), 4.08 (2H, m), 4.45 (1H, m), 5.10 (2H, s), 6.07 (1H, d, J=8 Hz), 6.45 (1H, m), 7.08 (1H, m), 7.34 (5H, bs)

(4) (2S)-2-Butanesulfonylamino-3-(N-(4-(1-t-butoxycarbonyl-4-piperidyl)butanoyl)glycylamino) propanoic Acid Methyl Ester The compound (79 mg) obtained in the above (3) is dissolved in ethanol (10 ml), and thereto is added 10% palladium-carbon (50% wet, 80 mg), and the mixture is stirred at room temperature for four hours under hydrogen atmosphere. The insoluble materials are removed by filtration, and the filtrate is concentrated under reduced pressure to give an amine compound (67 mg).

The amine compound is dissolved in ethyl acetate (10 ml), and there are added sodium hydrogen carbonate (100 mg) and butanesulfonyl chloride (50 μl) at room temperature. The mixture is refluxed for 6 hours, and evaporated under reduced pressure to remove the solvent. To the residue is added ethyl acetate, and the mixture is washed successively with 1N hydrochloric acid (twice), a saturated brine (once), a saturated aqueous sodium hydrogen carbonate solution (twice) and a saturated brine (twice), and dried over anhydrous magnesium sulfate. The desiccant is removed by filtration, and the filtrate is concentrated under reduced pressure. The residue is purified by silica gel column chromatography (silica gel; 10 g, solvent; chloroform-acetone= 3:2 to 1:1). The fractions containing the title compound are concentrated under reduced pressure to give the title compound (41 mg).

$^1$H-NMR (CDCl$_3$) δ (ppm): 0.90–2.00 (16H, m), 1.45 (9H, s), 2.25 (2H, m), 2.65 (2H, m), 3.00 (2H, m), 3.50–3.90 (2H, m), 3.80 (3H, s) 3.95 (2H, d, J=5 Hz), 4.08 (2H, m), 4.25 (1H, m), 5.95 (1H, m), 6.58 (1H, m), 7.10 (1H, m)

(5) (2S)-2-Butanesulfonylamino-3-(N-(4-(4-piperidyl) butanoyl)glycylamino)propanoic Acid TFA Salt The compound (40 mg) obtained in the above (4) is dissolved in a mixture of methanol (2 ml) and THF (2 ml), and thereto is added an aqueous lithium hydroxide solution (LiOH; 36 mg, water; 2 ml), and the mixture is stirred at room temperature for three hours. The mixture is concentrated under reduced pressure, and the pH value of the residue is adjusted to pH 2 with 1N HCl, and the mixture is extracted three times with ethyl acetate. The extract is washed twice with a saturated brine, and dried over anhydrous magnesium sulfate. The desiccant is removed by the filtration, and the filtrate is concentrated under reduced pressure. The residue is dissolved in TFA (3 ml) under ice-cooling, and the mixture is stirred for one hour. The reaction mixture is concentrated under reduced pressure, and the residue is purified by HPLC to give a white powder (16 mg).

MS (SIMS): 435 [M+1]$^+$

HPLC retention time: 13.86 min.

(Column: YMC-ODS 4.6 mmØ×250 mm, Detection: UV220 nm, Eluent; A solution: 0.1% TFA, water, B solution: 0.1% TFA/acetonitrile, Flow rate; 1 ml/min., Gradient; the concentration of B solution is increased from 10% at a rate of 1%/min.)

$^1$H-NMR (DMSO-d$_6$) δ (ppm): 0.87 (3H, t, J=7 Hz), 1.10–1.60 (9H, m), 1.65 (2H, m), 1.80 (2H, m), 2.12 (2H, t, J=7 Hz), 2.80 (2H, m), 2.98 (2H, t, J=8 Hz), 3.15–3.35 (4H, m), 3.66 (2H, d, J=5.5 Hz), 3.96 (1H, m), 7.53 (1H, d, J=9 Hz), 7.90–8.05 (2H, m), 8.15 (1H, bs), 8.45 (1H, bs)

The chemical structures of the compounds obtained in Example 1 to 5 are as follows.

Example 6

Synthesis of (2S)-2-benzenesulfonylamino-3-(N-(2-(4-piperidyl)ethyl)succinamylamino)propanoic Acid TFA Salt (1) 2-(1-t-Butoxycarbonyl-4-piperidyl)ethanoic Acid Ethyl Ester To a solution of ethyl diethylphosphonoacetate (5.40 g) in THF (20 ml) is added 60% NaH (885 mg) in portions under nitrogen atmosphere at a temperature below 40° C., and the mixture is stirred for 10 minutes. To the mixture is added dropwise a solution of 1-t-butoxycarbonyl-4-piperidinone (4.0 g), which is disclosed in Example 5-(1), in THF (15 ml) at a temperature below 35° C., and the mixture is stirred at room temperature for two hours. To the reaction mixture is added water, and the mixture is extracted three times with ethyl acetate. The extract is washed successively with 1N hydrochloric acid (twice), a saturated brine (once), a saturated aqueous sodium hydrogen carbonate solution (twice) and a saturated brine (twice), and dried over anhydrous magnesium sulfate. The desiccant is removed by filtration, and the filtrate is concentrated under reduced pressure.

The residue is dissolved in a mixture of ethanol (40 ml) and ethyl acetate (20 ml), and thereto is added 10% palladium-carbon (50% wet, 1.1 g) and the mixture is stirred at room temperature for 6 hours under hydrogen atmo- Example 1

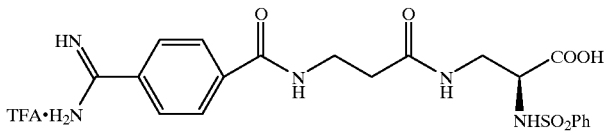

Example 2

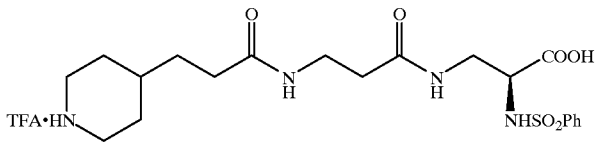

Example 3

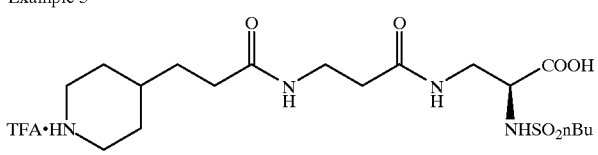

Example 4

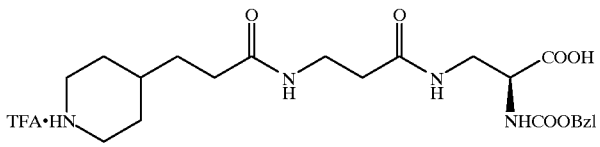

Example 5

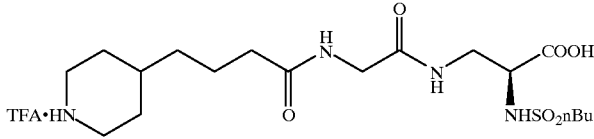

sphere. The insoluble materials are removed by the filtration, and the filtrate is concentrated under reduced pressure to give the title compound (5.80 g).

(2) 2-(1-t-Butoxycarbonyl-4-piperidyl)ethanoic Acid

The compound (5.28 g) obtained in the above (1) is dissolved in methanol (32 ml), and thereto is added 1N aqueous sodium hydroxide solution (23.4 ml), and the mixture is stirred at room temperature for three hours. The reaction mixture is diluted with water, and the pH value thereof is adjusted to pH 2 with 1N hydrochloric acid, and extracted three time with ethyl acetate. The extract is washed twice with a saturated brine, and dried over anhydrous magnesium sulfate. The desiccant is removed by filtration, and the filtrate is concentrated under reduced pressure to give the title compound (5.18 g).

$^1$H-NMR (CDCl$_3$) δ (ppm): 1.18 (2H, m), 1.45 (9H, s), 1.73 (2H, m), 1.95 (1H, m), 2.29 (2H, d, J=7 Hz), 2.73 (2H, dd, J=12, 12 Hz), 4.08 (2H, m)

(3) 2-(1-t-Butoxycarbonyl-4-piperidyl)ethanol

The compound (4.68 g) obtained in (2) is dissolved in dichloromethane (50 ml), and thereto are added N-hydroxysuccinimide (2.23 g) and WSC.HCl (3.72 g), and the mixture is stirred at room temperature for 12 hours. The reaction mixture is diluted with dichloromethane, and washed twice with water, and dried over anhydrous magnesium sulfate. The desiccant is removed by filtration, and the filtrate is concentrated under reduced pressure to give a white solid.

The white solid is dissolved in tetrahydrofuran (70 ml), and thereto is added sodium borohydride (3.23 g). The mixture is stirred at room temperature for 30 minutes, and stirred at 50° C. for four hours. The reaction solution is allowed to cool, and thereto is added 10% aqueous ammonium chloride solution (200 ml), and the mixture is extracted three times with ethyl acetate. The extract is washed with water and a saturate brine, and dried over anhydrous magnesium sulfate. The desiccant is removed by the filtration, and the filtrate is concentrated under reduced pressure to give a white solid (4.11 g).

(4) 1-Bromo-2-(1-t-butoxycarbonyl-4-piperidyl)ethane

The compound (1.497 g) obtained in the above (3) is dissolved in THF (40 ml), and thereto are added carbon tetrabromide (1.97 g) and triphenylphosphine (2.561 g) under ice-cooling, and the mixture is stirred at room temperature for three hours. To the mixture are further added carbon tetrabromide (1.97 g) and triphenylphosphine (2.561 g) under ice-cooling, and the mixture is stirred at room temperature for two hours. The insoluble materials are removed by filtration, and the filtrate is concentrated under reduced pressure. The residue is purified by silica gel column chromatography (silica gel; 200 g, solvent; hexane/ ethyl acetate=15:1). The fractions containing the title compound are concentrated under reduced pressure to give a bromo compound (0.77 g).

$^1$H-NMR (CDCl$_3$) δ (ppm): 1.10 (2H, m), 1.45 (9H, s), 1.40–2.00 (5H, m), 2.70 (2H, dd, J=12 Hz), 3.44 (2H, t, J=7 Hz), 4.10 (2H, m)

(5) 1-Amino-2-(1-t-butoxycarbonyl-4-piperidyl)ethane

The compound (0.77 g) obtained in the above (4) is dissolved in DMF (5 ml), and thereto is added potassium phthalimide (0.537 g), and the mixture is stirred at 100° C. for 1.5 hour. The reaction mixture is diluted with water, and extracted three times with ethyl acetate. The extract is washed successively with 1N hydrochloric acid (twice), a saturated brine (once), a saturated aqueous sodium hydrogen carbonate solution (twice) and a saturated brine (twice), and dried over anhydrous magnesium sulfate. The desiccant is removed by the filtration, and the filtrate is concentrated under reduced pressure. The residue is dissolved in ethanol (20 ml) and thereto is added hydrazine monohydrate (2.3 g) and the mixture is stirred at room temperature for 48 hours. The mixture is diluted with ether, and the insoluble materials are removed by filtration, and the filtrate is concentrated under reduced pressure to give the title compound (0.63 g) as an oily product.

$^1$H-NMR (CDCl$_3$) δ (ppm): 1.10 (2H, m), 1.45 (9H, s), 1.30–1.75 (5H, m), 2.00–2.30 (2H, bs), 2.72 (2H, dd, J=12 Hz), 2.78 (2H, t, J=7 Hz), 4.07 (2H, m)

(6) N-(2-(1-t-Butoxycarbonyl-4-piperidyl)ethyl) succinamide Acid

The compound (100 mg) obtained in the above (5) is dissolved in dichloromethane (2 ml), and thereto are added succinic anhydride (53 mg) and triethylamine (73 μl), and the mixture is stirred at room temperature for 45 minutes. To the mixture is added 1N hydrochloric acid, and the mixture is extracted three time with ethyl acetate. The extract is washed twice with a saturated brine, and the organic layer is dried over anhydrous magnesium sulfate. The desiccant is removed by filtration, and the filtrate is concentrated under reduced pressure to give the title compound (139 mg).

$^1$H-NMR (CDCl$_3$) δ (ppm): 1.05–1.25 (2H, m), 1.45 (9H, s), 1.35–1.80 (5H, m), 2.49 (2H, t, J=7 Hz), 2.59–2.95 (4H, m), 3.30 (2H, m), 3.97–4.17 (2H, m), 6.26 (1H, m)

(7) (2S)-2-Benzenesulfonylamino-3-t-butoxycarbonylaminopropanoic Acid Methyl Ester The compound (210 mg) obtained in Example 1-(3) is dissolved in a mixture of ethanol (10 ml) and ethyl acetate (5 ml) and thereto is added 10% palladium-carbon (50% wet, 170 mg), and the mixture is stirred at room temperature for 3.5 hours under hydrogen atmosphere. The insoluble materials are removed by filtration, and the filtrate is concentrated under reduced pressure to give an amine compound.

The amine compound is dissolved in dichloromethane (10 ml), and thereto are added triethylamine (513 μl) and benzenesulfonyl chloride (468 μl) at room temperature, and the mixture is stirred for two hours. The mixture is evaporated under reduced pressure to remove the solvent, and to the residue is added ethyl acetate. The mixture is washed successively with 1N hydrochloric acid (twice), a saturated brine (once), a saturated aqueous sodium hydrogen carbonate solution (twice), and a saturated brine (twice), and dried over anhydrous magnesium sulfate. The desiccant is removed by filtration, and the filtrate is concentrated under reduced pressure. The residue is purified by silica gel column chromatography (silica gel; 30 g, solvent; hexane/ ethyl acetate=5:1 to 1:1). The fractions containing the title compound are concentrated under reduced pressure to give the title compound (191 mg).

$^1$H-NMR (CDCl$_3$) δ (ppm): 1.42 (9H, s), 3.47 (2H, m), 3.55 (3H, s), 4.01 (1H, m), 5.03 (1H, m), 5.78 (1H, m), 7.55 (3H, m), 7.86 (2H, m)

(8) (2S)-2-Benzenesulfonylamino-3-(N-(2-(1-t-butoxycarbonyl-4-piperidyl)ethyl)succinamylamino) propanoic Acid Methyl Ester The compound (138 mg) obtained in the above (7) is dissolved in acetonitrile (2 ml) and thereto is added dropwise a solution of methanesulfonic acid (185 mg) in acetonitrile (2 ml) at a temperature below 20° C., and the mixture is stirred at room temperature for 40 minutes. To the mixture are added successively DMF (4 ml) and a solution of triethylamine (195 mg) in DMF (1 ml) under ice-cooling, and the mixture is stirred for 10 minutes. To the mixture are added a solution of the compound (140 mg) obtained in the above (6) in DMF (3 ml) and HOBT.H$_2$O (71 mg), and further thereto is added WSC.HCl (89 mg), and the mixture is stirred for 30 minutes, and then stirred at room temperature for 12 hours. The mixture is poured into water, and extracted three times with ethyl acetate. The organic layer is washed successively with 1N hydrochloric acid (twice), a saturated aqueous sodium hydrogen carbonate solution (twice), and a saturated brine (twice), and dried over anhydrous magnesium sulfate. The desiccant is removed by filtration, and the filtrate is concentrated under reduced pressure to give the title compound (265 mg) as an oily product.

$^1$H-NMR (CDCl$_3$) δ (ppm): 1.00–1.20 (2H, m), 1.45 (9H, s), 1.40–1.80 (5H, m), 2.50–2.80 (6H, m), 3.30 (2H, m), 3.52 (3H, s), 3.58 (2H, m), 4.00–4.20 (3H, m), 6.25 (1H, m), 6.40 (1H, m), 7.00 (1H, m), 7.40–7.60 (3H, m), 7.86 (2H, m)

(9) (2S)-2-Benzenesulfonylamino-3-(N-(2-(4-piperidyl)ethyl)succinamylamino)propanoic Acid TFA Salt The compound (265 mg) obtained in the above (8) is dissolved in a mixture of methanol (3 ml) and THF (3 ml) and thereto is added an aqueous solution of lithium hydroxide solution (LiOH; 120 mg, water; 3 ml), and the mixture is stirred at room temperature for 3 hours. The mixture is evaporated under reduced pressure to remove the solvent, and the pH value of the residue is adjusted to pH 1 with 1N HCl, and extracted three times with ethyl acetate. The extract is washed twice with a saturated brine, and dried over anhydrous magnesium sulfate. The desiccant is removed by filtration, and the filtrate is concentrated under reduced pressure. The residue is dissolved in TFA (5 ml) under ice-cooling, and stirred for one hour. The reaction mixture is concentrated under reduced pressure, and the residue is purified by HPLC to give a white powder (16 mg).

MS (SIMS): 455 [M+1]$^+$

HPLC retention time: 15.4 min.

(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

$^1$H-NMR (DMSO-d$_6$) δ (ppm): 1.10–1.40 (4H, m), 1.52 (1H, m), 1.80 (2H, m), 2.21 (4H, m), 2.81 (2H, m), 3.00–3.40 (6H, m), 3.88 (1H, m), 7.58 (3H, m), 7.78 (3H, m), 7.90 (1H, t, J=5 Hz), 8.11 (1H, d, J=9 Hz), 8.20 (1H, bs), 8.50 (1H, bs)

Example 7

Synthesis of (2S)-2-butanesulfonylamino-3-(N-(3-(4-piperidyl)propanoyl)-N-methyl-L-alanylglycylamino)propanoic Acid TFA Salt (1) N-t-Butoxycarbonyl-N-methyl-L-alanylglycine N-t-Butoxycarbonyl-N-methyl-L-alanine (1.00 g) and glycine benzyl ester p-toluenesulfonate (1.66 g) are dissolved in DMF (20 ml), and thereto are added successively HOBT.H$_2$O (0.66 g), WSC.HCl (0.94 g) and triethylamine (0.50 g) under ice-cooling, and the mixture is stirred at room temperature for three hours. The mixture is poured into water, and extracted three times with ethyl acetate. The organic layer is washed successively with 10% aqueous citric acid solution (twice), a saturated brine (once), a saturated aqueous sodium hydrogen carbonate solution (twice), and a saturated brine (twice), and dried over anhydrous magnesium sulfate. The desiccant is removed by filtration, and the filtrate is concentrated under reduced pressure.

The residue is dissolved in methanol (10 ml), and thereto is added 10% palladium-carbon (50% wet, 1.5 g), and the mixture is stirred at room temperature for three hours under hydrogen atmosphere. The insoluble materials are removed by filtration, and the filtrate is concentrated under reduced pressure to give the title compound (1.168 g).

(2) (2S)-2-Benzyloxycarbonylamino-3-(N-t-butoxycarbonyl-N-methyl-L-alanylglycylamino)propanoic Acid Methyl Ester The compound (50 mg) obtained in Example 1-(3) is dissolved in acetonitrile (1 ml) and thereto is added methanesulfonic acid (68 mg) at a temperature below 20° C., and the mixture is stirred at room temperature for three hours. To the mixture are added successively DMF (1 ml), triethylamine (79 μl), the compound (37 mg) obtained in the above (1), HOBT.H$_2$O (19 mg) and WSC.HCl (27 mg) under ice-cooling, and thereto is further added triethylamine (20 μl). The mixture is stirred at room temperature for 12 hours, and the mixture is poured into water. The mixture is extracted three times with ethyl acetate, and the organic layer is washed successively with 10% aqueous citric acid solution (twice), a saturated brine (once), a saturated aqueous sodium hydrogen carbonate solution (twice), and a saturated brine (twice), and dried over anhydrous magnesium sulfate. The desiccant is removed by filtration, and the filtrate is concentrated under reduced pressure to give the title compound (70 mg) as an oily product.

(3) (2S)-2-Benzyloxycarbonylamino-3-(N-(3-(1-t-butoxycarbonyl-4-piperidyl)propanoyl)-N-methyl-L-alanylglycylamino)propanoic Acid Methyl Ester The compound (70 mg) obtained in the above (2) is dissolved in acetonitrile (1 ml) and thereto is added methanesulfonic acid (68 mg) at a temperature below 20° C., and the mixture is stirred at room temperature for 3 hours. To the mixture are added successively DMF (1 ml), triethylamine (79 μl), the compound (36 mg) obtained in Example 2-(3), HOBT.H$_2$O (19 mg) and WSC.HCl (27 mg) under ice-cooling, and thereto is further added triethylamine (20 μl). The mixture is stirred at room temperature for 12 hours, and thereto are further added triethylamine (10 μl) and BOP reagent (12 mg), and the mixture is stirred for four hours. The mixture is poured into water, and the mixture is extracted three times with ethyl acetate. The organic layer is washed successively with 10% aqueous citric acid solution (twice), a saturated brine (once), a saturated aqueous sodium hydrogen carbonate solution (twice), and a saturated brine (twice), and dried over anhydrous magnesium sulfate. The desiccant is removed by filtration, and the filtrate is concentrated under reduced pressure to give the title compound (84 mg) as an oily product.

(4) (2S)-2-Butanesulfonylamino-3-(N-(3-(1-t-butoxycarbonyl-4-piperidyl)propanoyl)-N-methyl-L-alanylglycylamino)propanoic Acid Methyl Ester The compound (84 mg) obtained in the above (3) is dissolved in methanol (2 ml) and thereto is added 10% palladium-carbon (50% wet, 100 mg), and the mixture is stirred at room temperature for two hours under hydrogen atmosphere. The insoluble materials are removed by filtration, and the filtrate is concentrated under reduced pressure.

The residue is dissolved in dichloromethane (2 ml), and thereto are added triethylamine (41 μl) and butanesulfonyl chloride (27 mg), and the mixture is stirred at room temperature for four hours. The mixture is evaporated under reduced pressure to remove the solvent, and the residue is purified by silica gel column chromatography (silica gel; 50 g, solvent; chloroform/methanol=20:1). The fractions containing the title compound are concentrated under reduced pressure to give the title compound (72 mg).

(5) (2S)-2-Butanesulfonylamino-3-(N-(3-(4-piperidyl)propanoyl)-N-methyl-L-alanylglycylamino)propanoic Acid TFA Salt The compound (72 mg) obtained in the above (4) is dissolved in DMF (1 ml) and thereto is added 1N aqueous sodium hydroxide solution (350 µl) under ice-cooling, and the mixture is stirred for one hour. The pH value of the mixture is adjusted to pH 1 with 10% aqueous citric acid solution, and the mixture is extracted three times with ethyl acetate. The extract is washed twice with a saturated brine, and dried over anhydrous magnesium sulfate. The desiccant is removed by filtration, and the filtrate is concentrated under reduced pressure. The residue is dissolved in TFA (2 ml) under ice-cooling, and the mixture is stirred for 25 minutes. The reaction mixture is concentrated under reduced pressure, and the residue is purified by HPLC to give a white powder (4.09 mg).

MS (SIMS): 506 [M+1]$^+$
HPLC retention time: 15.96 min.
(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

$^1$H-NMR (DMSO-d$_6$) δ (ppm): 0.87 (3H, t, J=7 Hz), 1.13–1.90 (14H, m), 2.25–2.65 (2H, m), 2.68–3.00 (4H, m), 2.70, 2.90 (3H, s), 3.26–3.50 (4H, m), 3.50–3.90 (3H, m), 4.63, 4.96 (1H, m), 6.53–7.35 (2H, m), 7.80–8.90 (3H, m)

Example 8

Synthesis of (2S)-2-butanesulfonylamino-3-(N-(6-(4-piperidyl)hexanoyl)glycylamino)propanoic Acid TFA Salt (1) 6-(1-t-Butoxycarbonyl-4-piperidyl)hexanoic Acid To a solution of dimethylsulfoxide (3.72 ml) in dichloromethane (20 ml) is added a solution of oxalyl chloride (2.29 ml) in dichloromethane (5 ml) at −78° C., and the mixture is stirred for five minutes. To the mixture is added dropwise a solution of the compound (2.0 g) obtained in Example 6-(3) in dichloromethane (25 ml), and the mixture is stirred for 15 minutes. To the reaction mixture is added triethylamine (9.72 ml), and the mixture is warmed to room temperature, and then stirred for 30 minutes. To the reaction mixture is added water, and the mixture is extracted three times with ethyl acetate. The organic layer is washed successively with 1N hydrochloric acid (twice), a saturated brine (once), a saturated aqueous sodium hydrogen carbonate solution (twice) and a saturated brine (twice), and dried over anhydrous magnesium sulfate. The desiccant is removed by filtration, and the filtrate is concentrated under reduced pressure. The residue is purified by silica gel column chromatography (silica gel; 50 g, solvent; hexane/ethyl acetate=4:1 to 3:1). The fractions containing the title compound are concentrated under reduced pressure to give an aldehyde compound.

To a solution of ethyl 4-diethylphosphonochrotonate (1.72 g) in THF (10 ml) is added dropwise 1.6M solution of butyl lithium in hexane (3.54 ml) at a temperature below −50° C., and the mixture is stirred at −78° C. for 15 minutes. To the mixture is added dropwise a solution of the above aldehyde compound (1.11 g) in THF (7 ml), and the mixture is stirred at −78° C. for 20 minutes, and stirred at −10° C. for two hours. Water is added to the reaction solution, and the mixture is extracted three times with ethyl acetate. The extract is washed successively with 1N hydrochloric acid (twice), a saturated brine (once), an aqueous sodium hydrogen carbonate solution (twice) and a saturated brine (twice), and dried over anhydrous magnesium sulfate. The desiccant is removed by the filtration, and the filtrate is concentrated under reduced pressure, and purified by silica gel column chromatography (silica gel; 76 g, solvent; hexane/ethyl acetate=4:1).

The fractions containing the title compound are concentrated under reduced pressure, and the residue is dissolved in ethanol (15 ml). To the mixture is added 10% palladium-carbon (50% wet, 0.8 g), and the mixture is stirred at room temperature for five hours under hydrogen atmosphere. The insoluble materials are removed by filtration, and the filtrate is evaporated under reduced pressure to remove the solvent. The residue is dissolved in a mixture of methanol (20 ml) and THF (10 ml), and thereto is added an aqueous solution of sodium hydroxide (NaOH; 1.08 g, water; 10 ml), and the mixture is stirred at room temperature for 30 minutes. The mixture is evaporated under reduced pressure to remove the solvent, and the pH value of the residue is adjusted to pH 1 with 1N HCl, and extracted three times with ethyl acetate. The extract is washed twice with a saturated brine, and dried over anhydrous magnesium sulfate. The desiccant is removed by filtration, and the filtrate is concentrated under reduced pressure to give the title compound (0.896 g) as a white solid.

$^1$H-NMR (CDCl$_3$) δ (ppm): 1.06 (2H, m), 1.20–1.72 (11H, m), 1.45 (9H, s), 2.35 (2H, t, J=7 Hz), 2.66 (2H, dd, J=12 Hz), 4.06 (2H, m)

(2) (2S)-2-Benzyloxycarbonylamino-3-(N-(6-(1-t-butoxycarbonyl-4-piperidyl)hexanoyl)glycylamino) propanoic Acid Methyl Ester The compound (200 mg) obtained in Example 5-(2) is dissolved in acetonitrile (2.5 ml) and thereto is added a solution of methanesulfonic acid (234 mg) in acetonitrile (1.5 ml) at a temperature below 20° C., and the mixture is stirred at room temperature for one hour. To the mixture are added successively DMF (4 ml), a solution of triethylamine (247 mg) in DMF (1.5 ml), the compound (161 mg) obtained in the above (1), HOBT.H$_2$O (90 mg), and WSC.HCl (113 mg) under ice-cooling, and then further added triethylamine (20 µl). The mixture is stirred for 30 minutes, and then stirred at room temperature for 12 hours. The mixture is poured into water, and extracted three times with ethyl acetate. The organic layer is washed successively with 10% aqueous citric acid solution (twice), a saturated brine (once), a saturated aqueous sodium hydrogen carbonate solution (twice) and a saturated brine (twice), and dried over anhydrous magnesium sulfate. The desiccant is removed by filtration, and the filtrate is concentrated under reduced pressure. The residue is purified by silica gel column chromatography (silica gel; 50 g, solvent; chloroform/acetone= 3:1). The fractions containing the title compound are concentrated under reduced pressure to give the title compound (171 mg) as an oily product.

$^1$H-NMR (CDCl$_3$) δ (ppm): 1.00 (2H, m), 1.10–1.80 (1 1H, m), 1.45 (9H, s), 2.19 (2H, t, J=8 Hz), 2.65 (2H, dd, J=12 Hz), 3.60 (2H, m), 3.70 (3H, s), 3.85 (2H, d, J=5 Hz), 4.05 (2H, m), 4.45 (1H, m), 5.10 (2H, s), 6.20 (1H, m), 6.66 (1H, m), 7.40 (6H, m)

(3) (2S)-2-Butanesulfonylamino-3-(N-(6-(1-t-butoxycarbonyl-4-piperidyl)hexanoyl)glycylamino) propanoic Acid Methyl Ester The compound (171 mg) obtained in the above (2) is dissolved in a mixture of ethanol (10 ml) and ethyl acetate (3 ml), and thereto is added 10% palladium-carbon (50% wet, 200 mg), and the mixture is stirred at room temperature for five hours under hydrogen atmosphere. The insoluble materials are removed by filtration, and the filtrate is concentrated under reduced pressure to give an amine compound.

The amine compound is dissolved in ethyl acetate (10 ml), and thereto are added sodium hydrogen carbonate (55 mg) and butanesulfonyl chloride (69 µl), and the mixture is refluxed with stirring for 12 hours. The mixture is evaporated under reduced pressure to remove the solvent, and to the residue is added ethyl acetate. The mixture is washed successively with 1N hydrochloric acid (twice), a saturated brine (once), a saturated aqueous sodium hydrogen carbonate solution (twice), and a saturated brine (twice), and dried over anhydrous magnesium sulfate. The desiccant is removed by filtration, and the filtrate is concentrated under reduced pressure to give the title compound (131 mg) as an oily product.

$^1$H-NMR (CDCl$_3$) δ (ppm): 0.90–1.15 (7H, m), 1.15–2.20 (13H, m), 1.45 (9H, s), 2.28 (2H, m), 2.70 (2H, dd, J=12 Hz), 2.95–3.20 (2H, m), 3.50–4.16 (6H, m), 3.80, 3.90 (3H, s), 4.20–4.40, 4.65–4.75 (1H, m), 5.82–6.10 (1H, m), 6.65 (1H, m), 7.20, 7.45 (1H, m)

(4) (2S)-2-Butanesulfonylamino-3-(N-(6-(4-piperidyl)hexanoyl)glycylamino)propanoic Acid TFA Salt The compound (131 mg) obtained in the above (3) is dissolved in a mixture of methanol (6 ml) and THF (3 ml) and thereto is added an aqueous solution of lithium hydroxide (LiOH; 110 mg, water; 1.5 ml), and the mixture is stirred at room temperature for 2 hours. The mixture is evaporated under reduced pressure to remove the solvent, and the pH value of the residue is adjusted to pH 1 with 1N HCl, and extracted three times with ethyl acetate. The extract is washed twice with a saturated brine, and dried over anhydrous magnesium sulfate. The desiccant is removed by filtration, and the filtrate is concentrated under reduced pressure. The residue is dissolved in TFA (5 ml) under ice-cooling, and stirred for one hour. The reaction mixture is concentrated under reduced pressure, and the residue is purified by HPLC to give the title compound (98 mg) as an oily product.

MS (SIMS): 463 [M+1]$^+$

HPLC retention time: 19.6 min.

(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

$^1$H-NMR (DMSO-d$_6$) δ (ppm): 0.87 (3H, t, J=7 Hz), 1.10–1.75 (15H, m), 1.80 (2H, m), 2.11 (2H, t, J=7 Hz), 2.83 (2H, m), 3.00 (2H, m), 3.15–3.60 (4H, m), 3.65, 3.72 (2H, d, J=5.5 Hz), 4.00, 4.35 (1H, m), 7.10–7.60 (1H, m), 7.90–8.10 (2H, m), 8.20 (1H, bs), 8.50 (1H, bs)

Example 9

Synthesis of (2R)-2-butanesulfonylamino-3-(3-(3-(4-piperidyl)propanoylamino)propanoylamino) propanoic Acid TFA Salt The title compound is prepared from N-benzyloxycarbonyl-D-asparagine in the same manner as in Example 1 or 2.

Yield: 64 mg

MS (SIMS): 435 [M+1]$^+$

HPLC retention time: 13.3 min.

(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

$^1$H-NMR (DMSO-d$_6$) δ (ppm): 0.87 (3H, t, J=7 Hz), 1.10–1.58 (7H, m), 1.65 (2H, m), 1.78 (2H, m), 2.06 (2H, t, J=7 Hz), 2.23 (2H, t, J=7 Hz), 2.82 (2H, m), 2.97 (2H, t, J=6 Hz), 3.20 (4H, m), 3.42 (2H, m), 4.00 (1H, m), 7.52 (1H, d, J=9 Hz), 7.76 (1H, t, J=5 Hz), 8.03 (1H, t, J=5 Hz), 8.20 (1H, bs), 8.50 (1H, bs)

Example 10

Synthesis of (2S)-2-benzylsulfonylamino-3-(3-(3-(4-piperidyl)propanoylamino)propanoylamino) propanoic Acid TFA Salt The title compound is prepared from the compound obtained in Example 2-(5) in the same manner as in Example 3.

Yield: 170 mg

MS (SIMS): 469 [M+1]$^+$

HPLC retention time: 16.2 min.

(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

$^1$H-NMR (DMSO-d$_6$) δ (ppm): 1.20 (2H, m), 1.42 (3H, m), 1.75 (2H, m), 2.04 (2H, t, J=6.5 Hz), 2.23 (2H, t, J=7 Hz), 2.80 (2H, m), 3.26 (4H, m), 3.40 (2H, m), 3.90–4.20 (1H, m), 4.38 (2H, s), 7.37 (5H, m), 7.55 (1H, d, J=9 Hz), 7.76 (1H, t, J=5 Hz), 7.99 (1H, t, J=6 Hz), 8.20 (1H, bs), 8.50 (1H, bs)

The chemical structures of the compounds of Example 6 to 10 are as follows.

Example 6

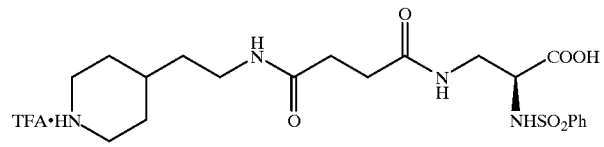

Example 7

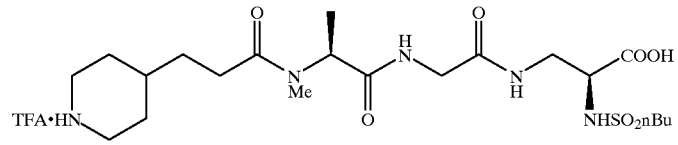

Example 8

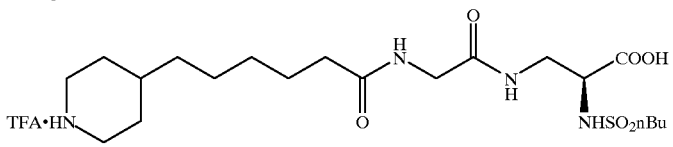

Example 9

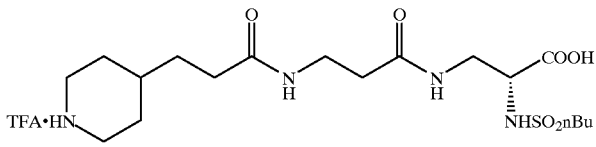

Example 10

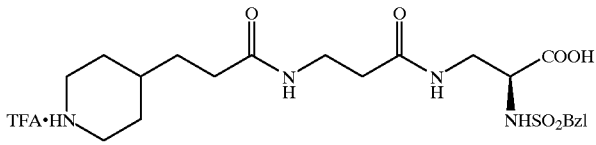

Example 11

Synthesis of (2S)-2-pentanoylamino-3-(3-(3-(4-piperidyl)propanoylamino)propanoylamino) propanoic Acid TFA Salt (1) (2S)-3-(3-(3-(1-t-Butoxycarbonyl-4-piperidyl) propanoylamino)propanoylamino)-2-pentanoylaminopropanoic Acid Methyl Ester The compound (100 mg) obtained in Example 2-(5) is dissolved in dichloromethane (2.5 ml) and thereto are added triethylamine (65 μl) and n-valeric anhydride (51 μl), and the mixture is stirred at room temperature for one hour. The reaction mixture is diluted with water, and extracted three times with ethyl acetate. The organic layer is washed successively with 1N hydrochloric acid (twice), a saturated brine (once), a saturated aqueous sodium hydrogen carbonate solution (twice) and a saturated brine (twice), and dried over anhydrous magnesium sulfate. The desiccant is removed by filtration, and the filtrate is concentrated under reduced pressure to give the title compound as a white powder (103 mg).

$^1$H-NMR (CDCl$_3$) δ (ppm): 0.88–0.98 (3H, m), 1.00–1.18 (2H, m), 1.30–1.48 (4H, m), 1.45 (9H, s), 1.52–1.85 (5H, m), 2.15–2.30 (2H, m), 2.35–2.50 (4H, m), 2.66 (2H, dd, J-12 Hz), 3.57–3.70 (4H, m), 3.77 (3H, s), 4.00–4.15 (2H, m), 4.60–4.70 (1H, m), 6.41 (1H, m), 6.67 (1H, m), 6.77 (1H, d, J=7 Hz)

(2) (2S)-3-(3-(3-(4-Piperidyl)propanoylamino) propanoylamino)-2-pentanoylaminopropanoic Acid TFA Salt The title compound is prepared from the compound obtained in the above (1) in the same manner as in Example 4.

Yield: 88 mg

MS (SIMS): 399 [M+1]$^+$

HPLC retention time: 11.1 min.

(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

$^1$H-NMR (DMSO-d$_6$) δ (ppm): 0.85 (3H, t, J=7 Hz), 1.27 (4H, m), 1.46 (5H, m), 1.80 (2H, m), 2.03–2.18 (4H, m), 2.20 (2H, t, J=7 Hz), 2.81 (2H, m), 3.23 (4H, m), 3.46 (2H, m), 4.30 (1H, m), 7.78 (1H, m), 8.00 (2H, m), 8.20 (1H, bs), 8.50 (1H, bs)

Example 12

Synthesis of (2S)-2-butanesulfonylamino-3-(N-(5-(4-piperidyl)pentanoyl)glycylamino)propanoic Acid TFA Salt (1) 5-(1-t-Butoxycarbonyl-4-piperidyl)pentanoic Acid To a solution of dimethylsulfoxide (4.40 ml) in dichloromethane (100 ml) is added a solution of oxalyl chloride (4.10 ml) in dichloromethane (15 ml) at −78° C., and the mixture is stirred for five minutes. To the mixture is added dropwise a solution of the compound (5.0 g) obtained in Example 2-(1) in dichloromethane (30 ml), and the mixture is stirred for 15 minutes. To the reaction mixture is added triethylamine (10.4 ml), and the mixture is warmed to room temperature, and then stirred for 30 minutes. To the reaction mixture is added water, and the mixture is extracted three times with ethyl acetate. The organic layer is washed successively with 1N hydrochloric acid (twice), a saturated brine (once), a saturated aqueous sodium hydrogen carbonate solution (twice) and a saturated brine (twice), and dried over anhydrous magnesium sulfate. The desiccant is removed by filtration, and the filtrate is concentrated under reduced pressure. The residue is purified by silica gel column chromatography (silica gel; 200 g, solvent; toluene/ ethyl acetate=1:1). The fractions containing the title compound are concentrated under reduced pressure to give an aldehyde compound (4.99 g).

To a solution of ethyl 4-diethylphosphonochrotonate (5.38 g) in THF (20 ml) is added dropwise 1.6M solution of butyl lithium in hexane (12.3 ml) at a temperature below −50° C., and the mixture is stirred at −78° C. for 15 minutes. To the mixture is added dropwise a solution of the above aldehyde compound (3.8 g) in THF (20 ml), and the mixture is stirred at −78° C. for 20 minutes, and stirred at −10° C. for two hours. Water is added to the reaction solution, and the mixture is extracted three times with ethyl acetate. The extract is washed successively with 1N hydrochloric acid (twice), a saturated brine (once), a saturated aqueous sodium hydrogen carbonate solution (twice) and a saturated brine (twice), and dried over anhydrous magnesium sulfate. The desiccant is removed by the filtration, and the filtrate is concentrated under reduced pressure, and the residue is purified by silica gel column chromatography (silica gel; 250 g, solvent; toluene/ethyl acetate=5:1). The fractions containing the title compound are concentrated under reduced pressure to an ester compound (3.943 g).

The ester compound (3.943 g) is dissolved in ethanol (50 ml). To the mixture is added 10% palladium-carbon (50% wet, 2.0 g), and the mixture is stirred at room temperature for 10 hours under hydrogen atmosphere. The insoluble materials are removed by filtration, and the filtrate is evaporated under reduced pressure to remove the solvent. The residue is dissolved in methanol (20 ml), and thereto is added 1N aqueous sodium hydroxide solution (26.4 ml), and the mixture is stirred at room temperature for five hours. The mixture is evaporated under reduced pressure to remove the solvent, and the pH value of the residue is adjusted to pH 2 with 1N HCl, and extracted three times with ethyl acetate. The extract is washed twice with a saturated brine, and dried over anhydrous magnesium sulfate. The desiccant is removed by filtration, and the filtrate is concentrated under reduced pressure to give the title compound (3.207 g) as a white solid.

$^1$H-NMR (CDCl$_3$) δ (ppm): 1.08 (2H, m), 1.20–1.72 (9H, m), 1.45 (9H, s), 2.36 (2H, t, J=7 Hz), 2.65 (2H, dd, J=12.5 Hz). 4.06 (2H, m)

(2) (2S)-2-Butanesulfonylamino-3-(N-(5-(4-piperidyl) pentanoyl)glycylamino)propanoic Acid TFA Salt The title compound is prepared from the compound obtained in the above (1) in the same manner as in Example 5.

Yield: 87 mg
MS (SIMS): 449 [M+1]$^+$
HPLC retention time: 16.50 min.
(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

$^1$H-NMR (DMSO-d$_6$) δ (ppm): 0.88 (3H, t, J=7 Hz), 1.10–1.58 (11H, m), 1.66 (2H, m), 1.78 (2H, m), 2.12 (2H, m), 2.82 (2H, m), 3.00 (2H, m), 3.20–3.50 (4H, m), 3.65 (2H, d, J=6 Hz), 3.97 (1H, m), 7.10–7.60 (1H, m), 7.90–8.08 (2H, m), 8.18 (1H, bs), 8.49 (1H, bs)

Example 13

Synthesis of (2S)-2-butanesulfonylamino-3-(3-(5-(4-piperidyl)pentanoylamino)propanoylamino) propanoic Acid TFA Salt The title compound is prepared from the compound obtained in Example 12-(1) and the compound obtained in Example 1-(4) in the same manner as in Example 2.

Yield: 159 mg
MS (SIMS): 463 [M+1]$^+$
HPLC retention time: 17.60 min.
(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

$^1$H-NMR (DMSO-d$_6$) δ (ppm): 0.87 (3H, t, J=7 Hz), 1.10–1.70 (13H, m), 1.78 (2H, m), 2.03 (2H, t, J=7 Hz), 2.22 (2H, t, J=7 Hz), 2.83 (2H, m), 2.96 (2H, t, J=6.5 Hz), 3.25 (4H, m), 3.40 (2H, m), 4.00 (1H, m), 7.52 (1H, d, J=9 Hz), 7.71 (1H, t, J=5.5 Hz), 8.02 (1H, t, J=6 Hz), 8.20 (1H, bs), 8.50 (1H, bs)

Example 14

Synthesis of (2S)-2-butanesulfonylamino-3-(N-(3-(4-piperidyl)propanoyl)-O-methyl-L-tyrosylglycylamino)propanoic Acid TFA Salt The title compound is prepared in the same manner as in Example 7.

Yield: 40 mg
MS (SIMS): 598 [M+1]$^+$
HPLC retention time: 24.23 min.
(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

$^1$H-NMR (DMSO-d$_6$) δ (ppm): 0.87 (3H, t, J=7 Hz), 1.05–1.50 (7H, m), 1.70 (4H, m), 2.08 (2H, m), 2.75 (2H, m), 2.96 (2H, m), 3.15–3.75 (8H, m), 3.70 (3H, s), 3.99 (1H, m), 4.47 (1H, m), 6.81 (2H, d, J=9 Hz), 7.15 (2H, d, J=9 Hz), 7.56 (1H, d, J=9 Hz), 7.98 (1H, m), 8.03–8.55 (4H, m)

The chemical structures of the compounds obtained in Examples 11 to 14 are as follows.

Example 11

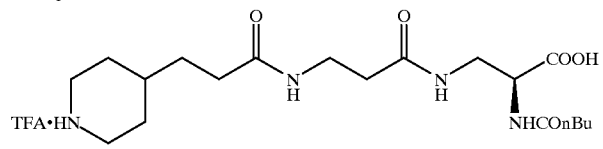

Example 12

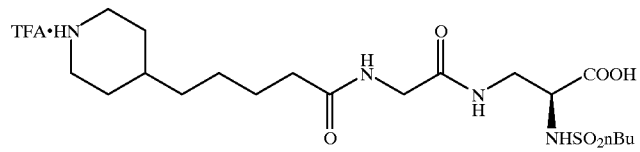

Example 13

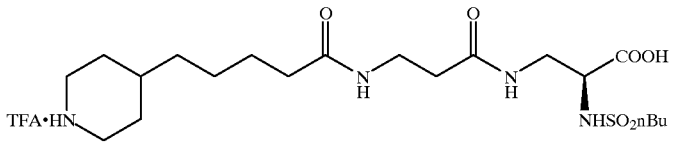

Example 14

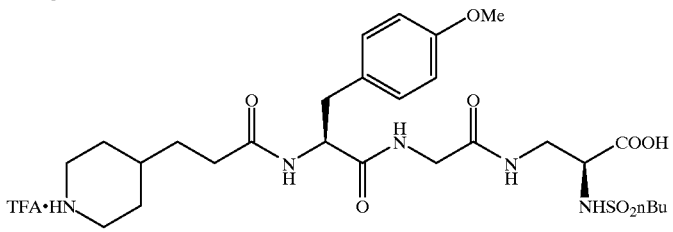

Example 15

Synthesis of (2S)-2-butanesulfonylamino-3-(N-(3-(4-piperidyl)propanoyl)-L-alanylglycylamino)propanoic Acid TFA Salt The title compound is prepared in the same manner as in Example 7.

Yield: 16.4 mg

MS (SIMS): 492 [M+1]$^+$

HPLC retention time: 13.39 min.

(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

$^1$H-NMR (DMSO-d$_6$) δ (ppm): 0.87 (3H, t, J=7 Hz), 1.20 (3H, d, J=7 Hz), 1.10–1.85 (11H, m), 2.18 (2H, m), 2.83 (2H, m), 2.98 (2H, m), 3.20–3.60 (4H, m), 3.67 (2H, d, J=6 Hz), 3.92 (1H, m), 4.23 (1H, m), 7.48 (1H, m), 7.95 (1H, m), 8.00–8.65 (4H, m)

Example 16

Synthesis of (2S)-2-methanesulfonylamino-3-(N-(3-(4-piperidyl)propanoyl)-O-methyl-L-tyrosylglycylamino)propanoic Acid TFA Salt The title compound is prepared in the same manner as in Example 7.

Yield: 15.6 mg

MS (SIMS): 556 [M+1]$^+$

HPLC retention time: 16.32 min.

(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

$^1$H-NMR (DMSO-d$_6$) δ (ppm): 1.00–1.40 (5H, m), 1.70 (2H, m), 2.10 (2H, m), 2.60–3.00 (4H, m), 2.92 (3H, s), 3.10–3.55 (4H, m), 3.65–3.80 (2H, m), 3.71 (3H, s), 4.00 (1H, m), 4.48 (1H, m), 6.82 (2H, d, J=8.5 Hz), 7.17 (2H, d, J=8.5 Hz), 7.55 (1H, d, J=9 Hz), 7.95 (1H, m), 8.07–8.20 (2H, m), 8.25 (1H, m), 8.42 (1H, m)

The chemical structures of the compounds obtained in Example 15 and 16 are as follows.

Example 15

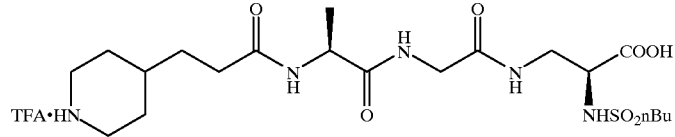

Example 16

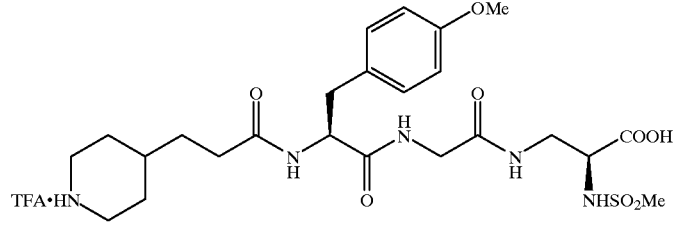

Example 17

Platelet Aggregation Inhibitory Activity

Method

The blood was collected from the elbow vein of a normal male volunteer with mixing thereof with ¹/₁₀ volume of 3.8% sodium citrate, and the blood was centrifuged at 1000 rpm (150 g) for 10 minutes to give the supernatant as platelet rich plasma (PRP). To PRP (200 μl) was added a test compound solution (2 μl), and the mixture was incubated with stirring at 1000 rpm at 37° C. for two minutes, and thereto was added a platelet aggregator, adenosine diphosphate (ADP, 22 μl) at a final concentration of 3 μg/ml. The platelet aggregation activity was determined by nephelometric analysis using a Hematracer (manufactured by Niko Bioscience, Ltd.). The test results of platelet aggregation inhibitory activity are expressed by $IC_{50}$, which is a concentration of the test compound being required to inhibit the platelet aggregation reaction by 50%. The test results of the test compounds are shown in Table 1.

TABLE 1

Test results

| Test Compound | $IC_{50}$ (M) |
| --- | --- |
| The compound of Example 1 | $1.60 \times 10^{-8}$ |
| The compound of Example 2 | $3.96 \times 10^{-8}$ |
| The compound of Example 3 | $1.62 \times 10^{-7}$ |
| The compound of Example 4 | $5.13 \times 10^{-7}$ |
| The compound of Example 5 | $2.99 \times 10^{-6}$ |
| The compound of Example 6 | $3.76 \times 10^{-7}$ |
| The compound of Example 7 | $1.22 \times 10^{-6}$ |
| The compound of Example 8 | $5.83 \times 10^{-7}$ |
| The compound of Example 9 | $3.63 \times 10^{-6}$ |
| The compound of Example 10 | $2.32 \times 10^{-7}$ |
| The compound of Example 11 | $8.73 \times 10^{-6}$ |
| The compound of Example 12 | $1.37 \times 10^{-6}$ |
| The compound of Example 13 | $1.81 \times 10^{-6}$ |
| The compound of Example 14 | $6.14 \times 10^{-6}$ |
| The compound of Example 15 | $5.24 \times 10^{-6}$ |
| The compound of Example 16 | $2.53 \times 10^{-6}$ |

Example 18

Synthesis of (2S)-3-(3-(4-amidinobenzoylamino)propanoylamino)-2-(4-methoxy)benzenesulfonylaminopropanoic Acid TFA Salt The title compound is prepared in the same manner as in Example 19.

Yield: 98 mg

MS (SIMS): 492 $[M+1]^+$

HPLC retention time: 16.7 min.

(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

$^1$H-NMR (DMSO-d$_6$) δ (ppm): 2.22–2.38 (2H, m), 3.05–3.30 (4H, m), 3.81 (3H, s), 3.71–3.90 (1H, m), 7.07 (2H, d, J=9 Hz), 7.69 (2H, d, J=6.9 Hz), 7.80–8.08 (6H, m), 8.65–8.75 (1H, m), 9.00–9.42 (4H, m)

Example 19

Synthesis of (2S)-3-(3-(4-amidinobenzoylamino)propanoylamino)-2-(2,4,6-trimethyl)benzenesulfonylaminopropanoic Acid TFA Salt (1) (2S)-3-(3-(4-Cyanobenzoylamino)propanoylamino)-2-(2,4,6-trimethyl)benzenesulfonylaminopropanoic Acid Ethyl Ester To a solution of (2S)-2-(2,4,6-trimethyl)benzenesulfonylamino-3-(3-(t-butoxycarbonylamino)propanoylamino)propanoic acid ethyl ester (0.579 g) obtained in the same manner as in Example 1-(3), -(4) and -(5) in acetonitrile (2 ml) is added dropwise a solution of methanesulfonic acid (0.573 g) in acetonitrile (2 ml) at a temperature below 20° C., and the mixture is stirred at room temperature for 30 minutes. To the mixture are added dropwise DMF (10 ml) and triethylamine (0.615 g) at a temperature below 20° C., and the mixture is stirred for 10 minutes. 4-Cyanobenzoic acid (0.193 g) and HOBT.H$_2$O (0.177 g) are added thereto, and thereto is further added WSC.HCl (0.251 g) at a temperature of from 5 to 10° C. The mixture is stirred for 30 minutes, and further stirred at room temperature for 12 hours. The reaction mixture is poured into water, and extracted three times with ethyl acetate. The organic layer is washed successively with 1N hydrochloric acid (twice), a saturated aqueous sodium hydrogen carbonate solution (twice) and a saturated brine (twice), and dried over anhydrous magnesium sulfate. The desiccant is removed by filtration, and the filtrate is concentrated under reduced pressure to give a residue.

(2) (2S)-3-(3-(4-Amidinobenzoylamino)propanoylamino)-2-( 2,4,6-trimethyl)benzenesulfonylaminopropanoic Acid TFA Salt The compound obtained in the above (1) is dissolved in a mixture of pyridine (12.5 ml) and triethylamine (2.5 ml), and thereto is blown hydrogen sulfide gas at room temperature for one hour, and then the mixture is allowed to stand for 12 hours. The hydrogen sulfide is removed by blowing nitrogen gas into the mixture, and the mixture is concentrated under reduced pressure. To the residue are added acetone (25 ml) and methyl iodide (0.5 ml), and the mixture is heated with stirring at 50–60° C. for three hours. After cooling, the mixture is concentrated under reduced pressure, and methanol (25 ml) and ammonium acetate (0.309 g) are added to the residue. The mixture is heated with stirring at 70–80° C. for 1 hour and 45 minutes. The mixture is concentrated under reduced pressure, and 1N hydrochloric acid (20 ml) and acetic acid (20 ml) are added to the residue, and the mixture is heated with stirring at 60–70° C. for 18 hours. The reaction mixture is concentrated under reduced pressure, and the residue is purified by HPLC to give a white powder (36 mg).

MS (SIMS): 504 $[M+1]^+$

HPLC retention time: 24.1 min.

(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

$^1$H-NMR (DMSO-d$_6$) δ (ppm): 2.17–2.30 (5H, m), 2.54 (6H, s), 3.13 (2H, m), 3.25–3.40 (2H, m), 3.84 (1H, m), 6.98 (2H, s), 7.86–8.03 (6H, m), 8.70 (1H, t, J=5.9 Hz), 9.27 (2H, m), 9.41 (2H, m)

Example 20

Synthesis of (2S)-3-(3-(4-amidinobenzoylamino)propanoylamino)-2-(1-naphthalene)sulfonylamino)propanoic Acid TFA Salt The title compound is prepared in the same manner as in Example 19.

Yield: 36 mg

MS (SIMS): 512 $[M+1]^+$

HPLC retention time: 21.9 min.

(Column: YMC-ODS 4.6 mmØ×250 mm, Detection: UV 220 nm, Eluent; A solution; 0.1% TFA/water, B solution;

0.1% TFA/acetonitrile, Flow rate: 1 ml/min., Gradient: The concentration of the B solution is increased from 10% at a rate of 1%/min.)

$^1$H-NMR (DMSO-d$_6$) δ (ppm): 2.05–2.28 (2H, m), 3.00–3.50 (4H, m), 3.85–3.95 (1H, m), 7.58–7.72 (3H, m), 7.72–8.14 (8H, m), 8.20, 8.48 (1H, d (J=7 Hz), d (J=8 Hz)), 8.61–8.68 (2H, m), 9.16 (2H, m), 9.39 (2H, s)

Example 21

Synthesis of (2S)-3-(3-(4-amidinobenzoylamino) propanoylamino)-2-(2-trifluoromethyl) benzenesulfonylaminopropanoic Acid TFA Salt The title compound is prepared in the same manner as in Example 19.

Yield: 71 mg

MS (SIMS): 530 [M+1]$^+$

HPLC retention time: 20.7 min.

(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

$^1$H-NMR (DMSO-d$_6$) δ (ppm): 2.33 (2H, m), 3.25 (2H, m), 3.50–3.90 (2H, m), 4.00 (1H, m), 7.77–7.97 (5H, m), 8.01 (2H, m), 8.12 (2H, m), 8.22 (1H, d, J=8.9 Hz), 8.72 (1H, t, J=5.3 Hz), 9.25 (2H, m), 9.40 (2H, m)

Example 22

Synthesis of (2S)-3-(3-(4-amidinobenzoylamino) propanoylamino)-2-benzenesulfonylaminopropanoic Acid Ethyl Ester (2S)-2-Benzenesulfonylamino-3-(3-(4-(N-t-butoxycarbonylamidino)benzoylamino)propanoylamino) propanoic acid ethyl ester (1.489) obtained in the same manner as in the synthesis of the compound of Example 1-(8) is dissolved in TFA (50 ml) under ice-cooling, and the mixture is stirred at room temperature for one hour. The reaction mixture is concentrated under reduced pressure, and the residue is washed with ether, and purified by HPLC to give the title compound (448 mg) as a colorless powder.

MS (SIMS): 490 [M+1]$^+$

HPLC retention time: 17.7 min.

(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 2%/min.)

$^1$H-NMR (DMSO-d$_6$) δ (ppm): 0.98 (3H, t, J=7 Hz), 2.32 (2H, t, J=7 Hz), 3.10–3.20 (4H, m), 3.77 (2H, q, J=7 Hz), 3.90–4.00 (1H, m), 7.52–7.68 (3H, m), 7.75 (2H, dd, J=2 Hz, 8 Hz), 7.88 (2H, d, J=8 Hz), 8.01 (2H, d, J=8 Hz), 8.08 (1H, m), 8.36 (1H, d, J=10 Hz), 8.72 (1H, m), 9.00–9.42 (4H, m)

Example 23

Synthesis of (2S)-3-(3-(4-amidinobenzoylamino) propanoylamino)-2-benzenesulfonylaminopropanoic Acid Methyl Ester The title compound is prepared in the same manner as in Example 22.

Yield: 58 mg

MS (SIMS): 476 [M+1]$^+$

HPLC retention time: 23.9 min.

(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

$^1$H-NMR (DMSO-d$_6$) δ (ppm): 2.31 (2H, t, J=8 Hz), 3.10–3.40 (4H, m), 3.40 (2H, s), 3.90–4.10 (1H, m), 7.50–7.69 (3H, m), 7.73 (2H, dd, J=2 Hz, 5 Hz), 7.77 (2H, d, J=2 Hz, 9 Hz), 8.01 (2H, dd, J=2 Hz, 9 Hz), 8.08 (1H, t, J=6 Hz), 8.37 (1H, d, J-9 Hz), 8.71 (1H, t, J=6 Hz), 9.19 (2H, bs), 9.40 (2H, bs)

The chemical structures of the compounds obtained in Examples 18 to 23 are as follows.

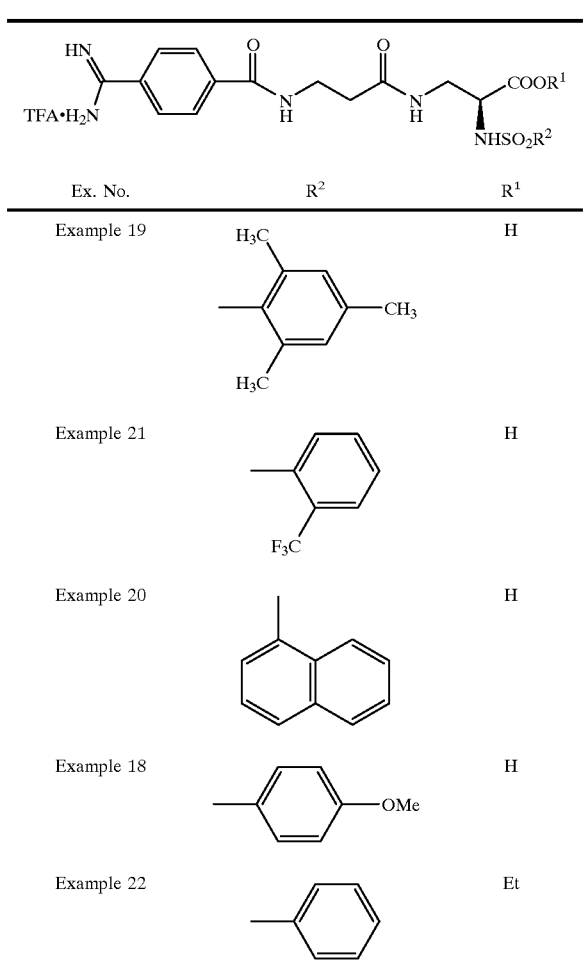

-continued

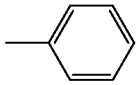

| Ex. No. | R² | R¹ |
|---|---|---|
| Example 23 | ⌬— | Me |

Example 24

Synthesis of (2S)-2-(2-methyl)
benzenesulfonylamino-3-(3-(3-(4-piperidyl)
propanoylamino)propanoylamino)propanoic Acid
TFA Salt The title compound is prepared in the same manner as in Example 2.

Yield: 102 mg

MS (SIMS): 469 [M+1]⁺

HPLC retention time: 18.2 min.

(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

¹H-NMR (DMSO-d₆) δ (ppm): 1.23 (2H, m), 1.43 (3H, m), 1.77 (2H, m), 2.06 (4H, m), 2.59 (3H, s), 2.80 (2H, m), 3.10–3.40 (6H, m), 3.82 (1H, m), 7.37 (2H, m), 7.49 (1H, m), 7.70–7.80 (2H, m), 7.97 (1H, t, J=5.4 Hz), 8.14 (1H, d, J=9.2 Hz), 8.20 (1H, m), 8.50 (1H, m)

Example 25

Synthesis of (2S)-2-(3-methyl)
benzenesulfonylamino-3-(3-(3-(4-piperidyl)
propanoylamino)propanoylamino)propanoic Acid
TFA Salt The title compound is prepared in the same manner as in Example 2.

Yield: 180 mg

MS (SIMS): 469 [M+1]⁺

HPLC retention time: 18.9 min.

(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

¹H-NMR (DMSO-d₆) δ (ppm): 1.23 (2H, m), 1.43 (3H, m), 1.77 (2H, m), 2.06 (4H, m), 2.37 (3H, s), 2.80 (2H, m), 3.10–3.40 (6H, m), 3.88 (1H, m), 7.41 (2H, m), 7.56 (1H, m), 7.57 (1H, s), 7.74 (1H, t, J=5.6 Hz), 7.97 (1H, t, J=4.8 Hz), 8.07 (1H, d, J=8.9 Hz), 8.21 (1H, m), 8.52 (1H, m)

Example 26

Synthesis of (2S)-2-(4-methyl)
benzenesulfonylamino-3-(3-(3-(4-piperidyl)
propanoylamino)propanoylamino)propanoic Acid
TFA Salt The title compound is prepared in the same manner as in Example 2.

Yield: 40 mg

MS (SIMS): 469 [M+1]⁺

HPLC retention time: 20.0 min.

(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

¹H-NMR (DMSO-d₆) δ (ppm): 1.23 (2H, m), 1.43 (3H, m), 1.77 (2H, m), 2.06 (4H, m), 2.36 (3H, s), 2.81 (2H, m), 3.03–3.35 (6H, m), 3.85 (1H, m), 7.35 (2H, d, J=7.9 Hz), 7.64 (2H, d, J=8.6 Hz), 7.73 (1H, t, J=5.3 Hz), 7.96 (1H, t, J=5.6 Hz), 8.03 (1H, d, J=8.9 Hz), 8.13 (1H, m), 8.47 (1H, m)

Example 27

Synthesis of (2S)-3-(3-(3-(4-piperidyl)
propanoylamino)-2-(2-trifluoromethyl)
benzenesulfonylaminopropanoic Acid TFA Salt The title compound is prepared in the same manner as in Example 2.

Yield: 161 mg

MS (SIMS): 523 [M+1]⁺

HPLC retention time: 21.1 min.

(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

¹H-NMR (DMSO-d₆) δ (ppm): 1.22 (2H, m), 1.43 (3H, m), 1.76 (2H, m), 2.06 (2H, m), 2.16 (2H, m), 2.80 (2H, m), 3.10–3.40 (6H, m), 4.00 (1H, m), 7.75 (1H, t, J=5.3 Hz), 7.83 (2H, m), 7.95 (1H, m), 8.05 (1H, t, J=5.9 Hz), 8.12 (1H, m), 8.21 (1H, d, J=8.9 Hz), 8.20 (1H, m), 8.55 (1H, m)

Example 28

Synthesis of (2S)-3-(3-(3-(4-piperidyl)
propanoylamino)propanoylamino)-2-(3-
trifluoromethyl)benzenesulfonylaminopropanoic
Acid TFA Salt The title compound is prepared in the same manner as in Example 2.

Yield: 306 mg

MS (SIMS): 523 [M+1]⁺

HPLC retention time: 23.7 min.

(Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.)

¹H-NMR (DMSO-d₆) δ (ppm): 1.23 (2H, m), 1.44 (3H, m), 1.77 (2H, m), 2.06 (2H, m), 2.14 (2H, t, J=6.6 Hz), 2.80 (2H, m), 3.05–3.45 (6H, m), 3.95 (1H, m), 7.72–7.85 (2H, m), 8.04 (4H, m), 8.17 (1H, m), 8.48 (1H, d, J=9.2 Hz), 8.48 (1H, m)

Example 29

Synthesis of (2S)-3-(3-(3-(4-piperidyl)propanoylamino)propanoylamino)-2-(4-trifluoromethyl)benzenesulfonylaminopropanoic Acid TFA Salt The title compound is prepared in the same manner as in Example 2.

Yield: 187 mg. MS (SIMS): 523 [M+1]$^+$. HPLC retention time: 24.5 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.22 (2H, m), 1.43 (3H, m), 1.76 (2H, m), 2.03–2.15 (4H, m), 2.80 (2H, m), 3.05–3.35 (6H, m), 3.95 (1H, m), 7.74 (1H, t, J=5.3 Hz), 7.96 (4H, s), 8.01 (1H, t, J=5.3 Hz), 8.15 (1H, m), 8.48 (1H, d, J=9.2 Hz), 8.48 (1H, m).

Example 30

Synthesis of (2S)-2-(2-nitro)benzenesulfonylamino-3-(3-(3-(4-piperidyl)propanoylamino)propanoylamino)propanoic Acid TFA Salt The title compound is prepared in the same manner as in Example 2.

Yield: 123 mg. MS (SIMS): 500 [M+1]$^+$. HPLC retention time: 19.9 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.20 (2H, m), 1.43 (3H, m), 1.76 (2H, m), 2.06 (2H, t, J=6.6 Hz), 2.17 (2H, t, J=7.6 Hz), 2.80 (2H, m), 3.10–3.50 (6H, m), 4.06 (1H, m), 7.74 (1H, t, J=5.3 Hz), 7.85 (2H, m), 7.92–8.07 (3H, m), 8.19 (1H, m), 8.39 (1H, m), 8.49 (1H, m).

The chemical structures of the compounds obtained in Examples 24 to 30 are as follows.

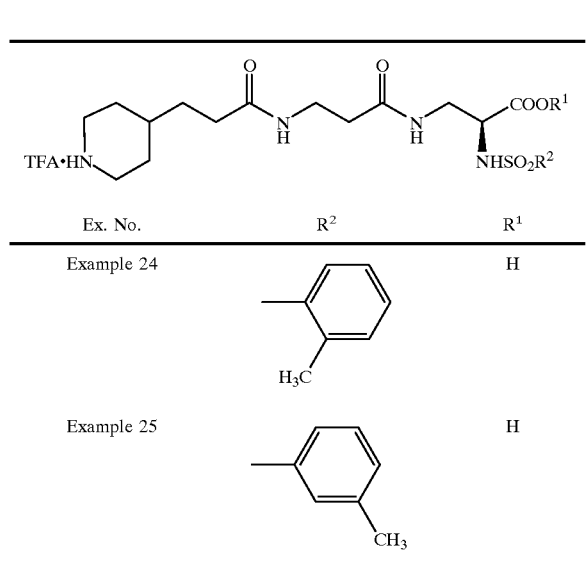

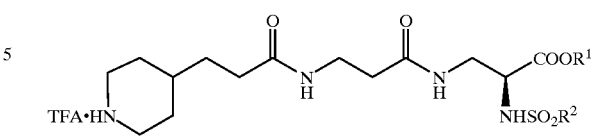

| Ex. No. | R$^2$ | R$^1$ |
|---|---|---|
| Example 26 | 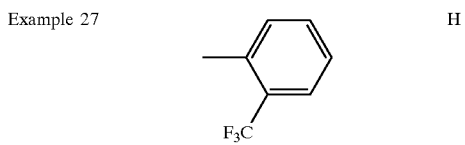 | H |
| Example 27 | 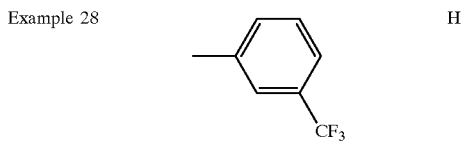 | H |
| Example 28 | 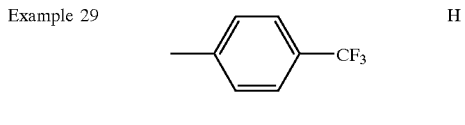 | H |
| Example 29 | 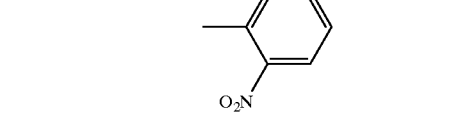 | H |
| Example 30 | | H |

Example 31

Synthesis of (2S)-2-(3-nitro)benzenesulfonylamino-3-(3-(3-(4-piperidyl)propanoylamino)propanoylamino)propanoic Acid TFA Salt The title compound is prepared in the same manner as in Example 2.

Yield: 199 mg. MS (SIMS): 500 [M+1]$^+$. HPLC retention time: 18.4 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.12–1.31 (2H, m), 1.37–1.53 (3H, m), 1.77 (2H, d, J=7 Hz), 2.06 (2H, t, J=7 Hz), 2.12 (2H, t, J=7 Hz), 2.70–2.90 (2H, m), 3.04–3.42 (6H, m), 3.90–4.01 (1H, m), 7.75 (1H, t, J=6 Hz), 7.87 (1H, t, J=8 Hz), 8.03 (1H, t, J=6 Hz), 8.13 (1H, d, J=7 Hz), 8.10–8.30 (1H, m), 8.40–8.66 (4H, m).

Example 32

Synthesis of (2S)-2-(4-nitro)benzenesulfonylamino-3-(3-(3-(4-piperidyl)propanoylamino)propanoylamino)propanoic Acid TFA Salt The title compound is prepared in the same manner as in Example 2.

Yield: 54 mg. MS (SIMS): 500 [M+1]$^+$. HPLC retention time: 20.7 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.21 (2H, m), 1.43 (3H, m), 1.77 (2H, m), 2.05 (2H, m), 2.13 (2H, m), 2.80 (2H, m), 3.05–3.43 (6H, m), 3.96 (1H, m), 7.74 (1H, t, J=5.3 Hz), 8.01 (3H, m), 8.17 (1H, m), 8.38 (2H, m), 8.50 (1H, m), 8.60 (1H, d, J=9.2 Hz).

Example 33

Synthesis of (2S)-3-(3-(3-(4-piperidyl)propanoylamino)propanoylamino)-2-(2,4,6-trimethyl)benzenesulfonylaminopropanoic Acid TFA Salt The title compound is prepared in the same manner as in Example 2.

Yield: 113 mg. MS (SIMS): 497 [M+1]$^+$. HPLC retention time: 24.5 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.23 (2H, m), 1.44 (3H, m), 1.76 (2H, m), 2.06 (4H, m), 2.24 (3H, s), 2.54 (6H, s), 2.80 (2H, m), 3.10–3.30 (6H, m), 3.80 (1H, m), 6.98 (2H, s), 7.73 (1H, t, J=5.6 Hz), 7.91 (2H, m), 8.18 (1H, m), 8.46 (1H, m).

Example 34

Synthesis of (2S)-2-(2,3,4,5,6-pentafluoro)benzenesulfonylamino-3-(3-(3-(4-piperidyl)propanoylamino)propanoylamino)propanoic Acid TFA Salt The title compound is prepared in the same manner as in Example 2.

Yield: 8.0 mg. MS (SIMS): 545 [M+1]$^+$. HPLC retention time: 23.5 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.21 (2H, m), 1.44 (3H, m), 1.77 (2H, m), 2.06 (2H, t, J=6.6 Hz), 2.19 (2H, m), 2.81 (2H, m), 3.10–3.40 (6H, m), 4.11 (1H, m), 7.76 (1H, t, J=5.6 Hz), 8.08 (1H, t, J=5.8 Hz), 8.10 (1H, m), 8.43 (1H, m), 9.23 (1H, d, J=9.2 Hz).

Example 35

Synthesis of (2S)-2-(4-fluoro)benzenesulfonylamino-3-(3-(3-(4-piperidyl)propanoylamino)propanoylamino)propanoic Acid TFA Salt The title compound is prepared in the same manner as in Example 2.

Yield: 141 mg. MS (SIMS): 473 [M+1]$^+$. HPLC retention time: 19.1 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.21 (2H, m), 1.44 (3H, m), 1.76 (2H, m), 2.06 (2H, t, J=7.6 Hz), 2.14 (2H, t, J=6.9 Hz), 2.80 (2H, m), 3.05–3.40 (6H, m), 3.88 (1H, m), 7.39 (2H, m), 7.84–7.75 (3H, m), 8.00 (1H, t, J=5.6 Hz), 8.21 (1H, d, J =9.2 Hz), 8.21 (1H, m), 8.51 (1H, m).

Example 36

Synthesis of (2S)-2-(4-chloro)benzenesulfonylamino-3-(3-(3-(4-piperidyl)propanoylamino)propanoylamino)propanoic Acid TFA Salt The title compound is prepared in the same manner as in Example 2.

Yield: 144 mg MS (SIMS): 489 [M+1]$^+$. HPLC retention time: 20.4 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.13–1.33 (2H, m), 1.38–1.53 (3H, m), 1.77 (2H, d, J=14 Hz), 2.09 (2H, t, J=7 Hz), 2.14 (2H, t, J=7 Hz), 2.70–2.90 (2H, m), 3.02–3.50 (6H, m), 3.83–3.97 (1H, m), 7.63 (2H, d, J=8 Hz), 7.70–7.80 (3H, m), 8.00 (1H, bs), 8.22 (1H, bs), 8.29 (1H, d, J=9 Hz), 8.54 (1H, bs).

Example 37

Synthesis of (2S)-2-(4-bromo)benzenesulfonylamino-3-(3-(3-(4-piperidyl)propanoylamino)propanoylamino)propanoic Acid TFA Salt The title compound is prepared in the same manner as in Example 2.

Yield: 59 mg. MS (SIMS): 535, 533 [M+1]$^+$. HPLC retention time: 23.5 min. (Column: YMC-ODS 4.6 mmØ× 250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1 %/min.). $^1$H-NMR (DMSO-d$_6$) δ (ppm): 1.12–1.30 (2H, m), 1.37–1.52 (3H, m), 1.70–1.85 (2H, m), 2.06 (2H, t, J=7 Hz), 2.14 (2H, t, J=7 Hz), 2.70–2.90 (2H, m), 3.02–3.95 (7H, m), 7.68 (2H, d, J=9 Hz), 7.78 (2H, d, J=9 Hz), 7.70–7.80 (1H, m), 8.00 (1H, t, J=6 Hz), 8.19 (1H, bs), 8.29 (1H, d, J=9 Hz), 8.49 (1H, bs).

The chemical structures of the compounds obtained in Examples 31 to 37 are as follows.

3.80–3.92 (1H, m), 7.39 (2H, d, J=8 Hz), 7.67 (2H, d, J=8 Hz), 7.70–7.80 (1H, m), 7.91–7.99 (1H, m), 8.04 (1H, d, J=9 Hz), 8.15, 8.50 (2H, bs).

Example 39

Synthesis of (2S)-2-(4-t-butyl) benzenesulfonylamino-3-(3-(3-(4-piperidyl) propanoylamino)propanoylamino)propanoic Acid TFA Salt The title compound is prepared in the same manner as in Example 2.

Yield: 125 mg. MS (SIMS): 511 [M+1]$^+$. HPLC retention time: 28.4 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.22 (2H, m), 1.29 (9H, s), 1.43 (3H, m), 1.75 (2H, m), 2.05 (4H, m), 2.80 (2H, m), 3.00–3.40 (6H, m), 3.87 (1H, m), 7.56 (2H, d, J=8.6 Hz), 7.68 (2H, d, J=8.6 Hz), 7.74 (1H, t, J=5.6 Hz), 7.94 (1H, t, J=5.6 Hz), 8.04 (1H, d, J=8.9 Hz), 8.12 (1H, m), 8.47 (1H, m).

Example 40

Synthesis of (2S)-2-(4-methoxy) benzenesulfonylamino-3-(3-(3-(4-piperidyl) propanoylamino)propanoylamino)propanoic Acid TFA Salt The title compound is prepared in the same manner as in Example 2.

Yield: 74 mg. MS (SIMS): 485 [M+1]$^+$. HPLC retention time: 17.3 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.13–1.30 (2H, m), 1.36–1.53 (3H, m), 1.77 (2H, d, J=12 Hz), 2.06 (2H, t, J=7 Hz), 2.14 (2H, t, J=7 Hz), 2.70–2.90 (2H, m), 3.00–3.95 (7H, m), 3.82 (3H, s), 7.07 (2H, d, J=8 Hz), 7.69 (2H, d, J=8 Hz), 7.74 (1H, t, J=6 Hz), 7.95 (1H, d, J=9 Hz), 7.95–8.02 (1H, m), 8.17, 8.48 (2H, bs).

Example 41

Synthesis of (2S)-2-(1-naphthalene)sulfonylamino-3-(3-(3-(4-piperidyl)propanoylamino) propanoylamino)propanoic Acid TFA Salt The title compound is prepared in the same manner as in Example 2.

Yield: 154 mg. MS (SIMS): 505 [M+1]$^+$. HPLC retention time: 12.4 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.12–1.30 (2H, m), 1.36–1.53 (3H, m), 1.76 (2H, d, J=12 Hz), 1.90–2.10 (4H, m), 2.72–2.90 (2H, m), 3.00–3.70 (6H, m), 3.85–3.95 (1H, m), 7.58–7.77 (4H, m), 7.88 (1H, t, J=6 Hz), 8.00–8.25 (4H, m), 8.40–8.54 (2H, m), 8.64 (1H, d, J=8 Hz).

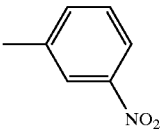

| Ex. No. | R$^2$ | R$^1$ |
|---|---|---|
| Example 31 | 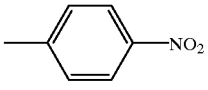 | H |
| Example 32 | 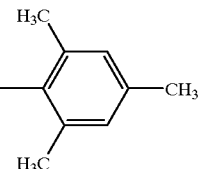 | H |
| Example 33 | 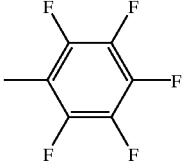 | H |
| Example 34 | 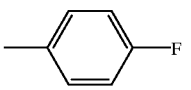 | H |
| Example 35 | 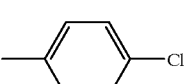 | H |
| Example 36 | 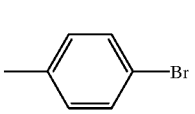 | H |
| Example 37 | (4-Br-C$_6$H$_4$) | H |

Example 38

Synthesis of (2S)-2-(4-ethyl)benzenesulfonylamino-3-(3-(3-(4-piperidyl)propanoylamino) propanoylamino)propanoic Acid TFA Salt The title compound is prepared in the same manner as in Example 2.

Yield: 152 mg. MS (SIMS): 483 [M+1]$^+$. HPLC retention time: 22.3 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.19 (3H, t, J=7 Hz), 1.00–1.25 (2H, m), 1.36–1.52 (3H, m), 1.77 (2H, d, J=13 Hz), 2.00–2.20 (4H, m), 2.67 (2H, q, J=7 Hz), 2.74–2.90 (2H, m), 3.03–3.54 (6H, m),

Example 42

Synthesis of (2S)-2-(5-dimethylamino-1-naphthalene)sulfonylamino-3-(3-(3-(4-piperidyl)propanoylamino)propanoylamino)propanoic Acid TFA Salt The title compound is prepared in the same manner as in Example 2.

Yield: 192 mg. MS (SIMS): 548 [M+1]$^+$. HPLC retention time: 15.6 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.21 (2H, m), 1.42 (3H, m), 1.75 (2H, m), 1.90–2.06 (4H, m), 2.80 (2H, m), 2.82 (6H, s), 3.03–3.35 (6H, m), 3.80–4.00 (1H, m), 7.25 (1H, d, J=7.6 Hz), 7.59 (2H, m), 7.69 (1H, t, J=5.6 Hz), 7.85 (1H, t, J=5.6 Hz), 8.10 (1H, m), 8.20 (1H, m), 8.28 (1H, d, J=8.6 Hz), 8.42 (2H, t, J=9.6 Hz), 8.45 (1H, m).

Example 43

Synthesis of (2S)-2-(2-naphthalene)sulfonylamino-3-(3-(3-(4-piperidyl)propanoylamino)propanoylamino)propanoic Acid TFA Salt The title compound is prepared in the same manner as in Example 2.

Yield: 159 mg. MS (SIMS): 505 [M+1]$^+$. HPLC retention time: 13.8 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.11–1.30 (2H, m), 1.35–1.51 (3H, m), 1.76 (2H, d, J=12 Hz), 2.00–2.16 (4H, m), 2.70–2.90 (2H, m), 3.05–3.55 (6H, m), 3.89–4.00 (1H, m), 7.60–7.85 (4H, m), 7.95–8.60 (8H, m).

Example 44

Synthesis of (2S)-2-ethanesulfonylamino-3-(3-(3-(4-piperidyl)propanoylamino)propanoylamino)propanoic Acid TFA Salt The title compound is prepared in the same manner as in Example 2.

Yield: 82 mg. MS (SIMS): 407 [M+1]$^+$. HPLC retention time: 12.1 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.20 (5H, m), 1.36–1.55 (3H, m), 1.77 (2H, d, J=14 Hz), 2.06 (2H, t, J=7 Hz), 2.23 (2H, t, J=7 Hz), 2.81 (2H, q, J=12 Hz), 2.97 (2H, q, J=7 Hz), 3.10–3.60 (6H, m), 3.90–4.04 (1H, m), 7.53 (1H, d, J=9 Hz), 7.76 (1H, t, J=6 Hz), 8.03 (1H, t, J=6 Hz), 8.20, 8.49 (2H, bs).

The chemical structures of the compounds obtained in Examples 38 to 44 are as follows.

| Ex. No. | R$^2$ | R$^1$ |
|---|---|---|
| Example 38 | 4-Et-C$_6$H$_4$– | H |
| Example 39 | 4-t-Bu-C$_6$H$_4$– | H |
| Example 40 | 4-OMe-C$_6$H$_4$– | H |
| Example 41 | 1-methyl-naphthalenyl | H |
| Example 42 | 5-dimethylamino-1-naphthalenyl | H |
| Example 43 | 2-naphthalenyl | H |
| Example 44 | –Et | H |

Example 45

Synthesis of (2S)-3-(3-(3-(4-piperidyl)propanoylamino)propanoylamino)-2-propanesulfonylaminopropanoic Acid TFA Salt The title compound is prepared in the same manner as in Example 2.

Yield: 54 mg. MS (SIMS): 421 [M+1]$^+$. HPLC retention time: 8.88 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 0.94 (3H, t, J=7 Hz), 1.10–1.35 (2H, m), 1.36–1.55 (3H, m), 1.60–1.85 (4H, m), 1.95–2.10 (2H, m), 2.18–2.30 (2H, m), 2.80–3.75 (10H, m), 3.90–4.02 (1H, m), 7.53 (1H, d, J=9 Hz), 7.72 (1H, m), 8.00–8.08 (1H, m), 8.10–8.65 (2H, m).

Example 46

Synthesis of (2S)-2-(4-methoxy-2,3,6-trimethyl)benzenesulfonylamino-3-(3-(3-(4-piperidyl)propanoylamino)propanoylamino)propanoic Acid TFA Salt The title compound is prepared in the same manner as in Example 2.

Yield: 219 mg. MS (SIMS): 527 [M+1]$^+$. HPLC retention time: 24.5 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.10–1.32 (2H, m), 1.39–1.53 (3H, m), 1.77 (2H, d, J=13 Hz), 2.07 (3H, s), 1.98–2.18 (4H, m), 2.51 (3H, s), 2.56 (3H, s), 2.71–2.90 (2H, m), 3.05–4.00 (7H, m), 3.81 (3H, s), 6.76 (1H, s), 7.70–7.76 (1H, m), 7.80 (1H, d, J=10 Hz), 7.90–7.98 (1H, m), 8.19 (1H, bs), 8.47 (1H, m).

Example 47

Synthesis of (2S)-3-(3-(3-(4-piperidyl)propanoylamino)propanoylamino)-2-(4-trifluoromethoxy)benzenesulfonylaminopropanoic Acid TFA Salt The title compound is prepared in the same manner as in Example 2.

Yield: 216 mg. MS (SIMS): 539 [M+1]$^+$. HPLC retention time: 25.6 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.12–1.31 (2H, m), 1.38–1.53 (3H, m), 1.76 (2H, d, J=13 Hz), 2.00–2.20 (4H, m), 2.72–2.90 (2H, m), 3.05–3.75 (6H, m), 3.88–4.00 (1H, m), 7.56 (2H, d, J=9 Hz), 7.75 (1H, t, J=6 Hz), 7.89 (2H, d, J=9 Hz), 7.90 (1H, t, J=6 Hz), 8.20 (1H, bs), 8.34 (1H, d, J=9 Hz), 8.52 (1H, bs).

Example 48

Synthesis of (2S)-2-(4-butoxy)benzenesulfonylamino-3-(3-(3-(4-piperidyl)propanoylamino)propanoylamino)propanoic Acid TFA Salt The title compound is prepared in the same manner as in Example 2.

Yield: 143 mg. MS (SIMS): 527 [M+1]$^+$. HPLC retention time: 29.7 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 0.94 (3H, t, J=7 Hz), 1.12–1.31 (2H, m), 1.38–1.54 (5H, m), 1.64–1.83 (4H, m), 2.06 (2H, d, J=7 Hz), 2.15 (2H, t, J=7 Hz), 2.73–2.90 (2H, m), 3.03–3.60 (6H, m), 3.79–3.88 (1H, m), 4.03 (2H, t, J=7 Hz), 7.06 (2H, d, J=9 Hz), 7.67 (2H, d, J=9 Hz), 7.74 (1H, t, J=6 Hz), 7.93 (1H, d, J=9 Hz), 7.97 (1H, t, J=6 Hz), 8.17 (1H, bs), 8.46 (1H, bs).

Example 49

Synthesis of (2S)-3-(3-(3-(4-piperidyl)propanoylamino)propanoylamino)-2-(4-propyl)benzenesulfonylaminopropanoic Acid TFA Salt The title compound is prepared in the same manner as in Example 2.

Yield: 146 mg. MS (SIMS): 497 [M+1]$^+$. HPLC retention time: 26.4 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 0.88 (3H, t, J=7 Hz), 1.12–1.32 (2H, m), 1.35–1.51 (3H, m), 1.55–1.69 (2H, m), 1.70–1.85 (2H, m), 2.00–2.20 (4H, m), 2.56–2.70 (2H, m), 2.72–2.80 (2H, m), 3.00–3.95 (7H, m), 7.37 (2H, d, J=8 Hz), 7.66 (2H, d, J=8 Hz), 7.72–7.80 (1H, m), 7.91–8.10 (2H, m), 8.10–8.76 (2H, m).

Example 50

Synthesis of (2S)-2-(4-isopropyl)benzenesulfonylamino-3-(3-(3-(4-piperidyl)propanoylamino)propanoylamino)propanoic Acid TFA Salt The title compound is prepared in the same manner as Example 2.

Yield: 226 mg. MS (SIMS): 497 [M+1]$^+$. HPLC retention time: 25.8 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.21 (6H, d, J=7 Hz), 1.05–1.25 (2H, m), 1.38–1.54 (3H, m), 1.77 (2H, d, J=14 Hz), 2.00–2.20 (4H, m), 2.72–2.90 (2H, m), 2.91–3.90 (8H, m), 7.42 (2H, d, J=8 Hz), 7.68 (2H, d, J=8 Hz), 7.74 (1H, bs), 7.95 (1H, bs), 8.26 (1H, d, J=9 Hz), 8.20, 8.52 (2H, bs).

Example 51

Synthesis of (2S)-2-benzenesulfonylamino-3-(3-(3-(4-piperidyl)propanoylamino)propanoylamino)propanoic Acid Ethyl Ester (2S)-2-Benzenesulfonylamino-3-(3-(3-(1-t-butoxycarbonyl-4-piperidyl)propanoylamino)propanoylamino)propanoic acid ethyl ester (462 mg), which is prepared in the same manner as in the synthesis of the compound of Example 2-(6), is dissolved in a mixture of TFA (10 ml) and anisole (1 ml) under ice-cooling, and the mixture is stirred for 30 minutes. The reaction mixture is concentrated under reduced pressure, and the residue is dissolved in water. The mixture is washed with ether, and the aqueous layer is concentrated under reduced pressure. The residue is purified by HPLC to give the title compound (227 mg) as a colorless powder.

MS (SIMS): 483 [M+1]$^+$. HPLC retention time: 22.1 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 0.99 (3H, t, J=7 Hz), 1.11–1.30 (2H, m), 1.36–1.50 (3H, m), 1.77 (2H, d, J=14 Hz), 2.08 (2H, t, J=7 Hz), 2.14 (2H, t, J=7 Hz), 2.72–2.90 (2H, m), 3.05–3.50 (6H, m), 3.78 (2H, q, J=7 Hz), 3.90–4.00 (1H, m), 7.52–7.68 (3H, m), 7.71–7.80 (3H, m), 7.98–8.55 (4H, m).

Example 52

Synthesis of (2S)-2-benzenesulfonylamino-3-(3-(3-(4-piperidyl)propanoylamino)propanoylamino)propanoic Acid (5-indanyl) Ester The title compound is prepared in the same manner as Example 51.

Yield: 239 mg. MS (SIMS): 571 [M+1]$^+$. HPLC retention time: 35.1 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.10–1.30 (2H, m), 1.35–1.50 (3H, m), 1.68–1.80 (2H, m), 1.90–2.10 (4H, m), 2.15–2.25 (2H, m), 2.70–2.90 (6H, m), 3.10–3.30 (6H, m), 4.13–4.25 (1H, m), 6.52–6.65 (2H, m), 7.16 (1H, d, J=8 Hz), 7.55–7.90 (6H, m), 8.10–8.30 (2H, m), 8.40–8.65 (2H, m).

The chemical structures of the compounds obtained in Examples 45 to 52 are as follows.

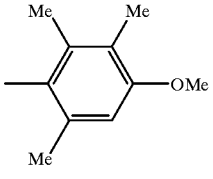

| Ex. No. | R$^2$ | R$^1$ |
|---|---|---|
| Example 45 | —Pr | H |
| Example 46 | 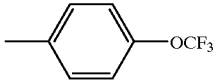 | H |
| Example 47 | 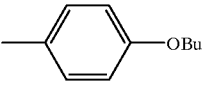 | H |
| Example 48 | 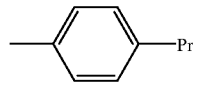 | H |
| Example 49 | 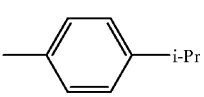 | H |
| Example 50 | 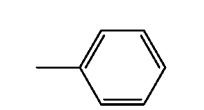 | H |
| Example 51 | 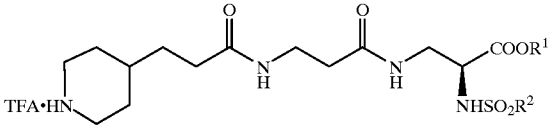 | Et |

-continued

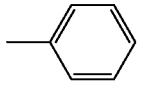

| Ex. No. | R$^2$ | R$^1$ |
|---|---|---|
| Example 52 | 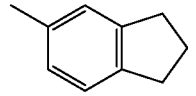 | |

Example 53

Synthesis of (2S)-2-benzenesulfonylamino-3-(3-(4-(4-piperidyl)butanoylamino)propanoylamino)propanoic Acid TFA Salt (1) (2S)-2-Benzyloxycarbonylamino-3-(3-(4-(1-t-butoxycarbonyl-4-piperidyl)butanoyl)aminopropanoyl)aminopropanoic Acid Ethyl Ester (2S)-2-Benzyloxycarbonylamino-3-(3-t-butoxycarbonylaminopropanoyl)aminopropanoic acid ethyl ester (500 mg), which is prepared in the same manner as in the synthesis of the compound of Example 1-(4), is dissolved in acetonitrile (5 ml), and thereto is added dropwise methanesulfonic acid (371 μl) under ice-cooling, and the mixture is stirred for 1.5 hour. To the mixture are added successively DMF (5 ml) and triethylamine (637 μl) under ice-cooling, and to the mixture are added the compound (335 mg) obtained in Example 5-(1), HOBT.H$_2$O (170 mg), and further thereto are added WSC.HCl (241 mg), and triethylamine (159 μl), and the mixture is stirred at room temperature for 20 hours. The mixture is poured into water, and extracted three times with ethyl acetate. The organic layer is washed successively with a saturated aqueous sodium hydrogen carbonate solution (twice) and a saturated brine (twice), and dried over anhydrous magnesium sulfate. The desiccant is removed by filtration, and the filtrate is concentrated under reduced pressure to give the title compound (738 mg).

(2) (2S)-2-Benzenesulfonylamino-3-(3-(4-(1-t-butoxycarbonyl-4-piperidyl)butanoyl)aminopropanoyl)aminopropanoic Acid Ethyl Ester The compound (738 mg) obtained in the above (1) is dissolved in ethanol (20 ml) and thereto is added 10% palladium-carbon (50% wet, 300 mg), and the mixture is stirred at room temperature for two hours under hydrogen atmosphere. The insoluble materials are removed by filtration, and the filtrate is concentrated under reduced pressure to give an amine compound (597 mg).

The amine compound (339 mg) is dissolved in dichloromethane (10 ml), and thereto are added benzenesulfonyl chloride (146 mg) and triethylamine (250 μl) and the mixture is stirred for one hour. The mixture is evaporated under reduced pressure to remove the solvent, and to the residue is added ethyl acetate. The mixture is washed successively with 1N hydrochloric acid (twice), a saturated brine (once), a saturated aqueous sodium hydrogen carbonate solution (twice), and a saturated brine (twice), and dried over anhydrous magnesium sulfate. The desiccant is removed by filtration, and the filtrate is concentrated under reduced pressure. The residue is purified by silica gel column chromatography (silica gel; 30 g, solvent; chloroform/methanol= 20:1). The fractions containing the title compound are concentrated under reduced pressure to give the title compound (483 mg).

(3) (2S)-3-(3-(4-(4-Piperidyl)butanoyl)aminopropanoyl)amino-2-benzenesulfonylaminopropanoic Acid TFA Salt The compound (40 mg) obtained in the above (2) is dissolved in ethanol (5 ml) and thereto is added an aqueous solution of lithium hydroxide (LiOH; 195 mg, water; 5 ml), and the mixture is stirred at room temperature for 12 hours. The mixture is evaporated under reduced pressure to remove the solvent, and the pH value of the residue is adjusted to pH 2 with 10% citric acid, and extracted three times with ethyl acetate. The extract is washed twice with a saturated brine, and dried over anhydrous magnesium sulfate. The desiccant is removed by filtration, and the filtrate is concentrated under reduced pressure. The residue is dissolved in TFA (10 ml) under ice-cooling, and the mixture is stirred for 30 minutes. The reaction mixture is concentrated under reduced pressure, and the residue is purified by HPLC to give a white powder (277 mg).

MS (SIMS): 469 [M+1]$^+$. HPLC retention time: 19.8 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.17 (4H, m), 1.47 (3H, m), 1.76 (2H, m), 2.02 (2H, t, J=7.6 Hz), 2.11 (2H, m), 2.80 (2H, m), 3.00–3.35 (6H, m), 3.88 (1H, m), 7.57 (3H, m), 7.69 (1H, t, J=5.9 Hz), 7.76 (2H, m), 7.96 (1H, t, J=6.3 Hz), 8.14 (1H, d, J=8.9 Hz), 8.14 (1H, m), 8.43 (1H, m).

Example 54

Synthesis of (2S)-2-benzenesulfonylamino-3-(4-(4-piperidylmethylcarbamoyl)butanoylamino)propanoic Acid TFA Salt (1) (1-t-Butoxycarbonyl-4-piperidyl)methylamine 4-Piperidylmethylamine (1.0 g) is dissolved in DMF (20 ml), and thereto are added 18-crown-6 (3.47 g), p-toluenesulfonic acid monohydrate (3.66 g) and triethylamine (1.46 ml) under ice-cooling, and the mixture is stirred for two hours. To the mixture is added di-t-butyl dicarbonate (2.29 g), and the mixture is further stirred for two hours. The mixture is evaporated under reduced pressure to remove the solvent, and 10% aqueous citric acid solution is added to the residue. The mixture is washed twice with ether, and the aqueous layer is basified with sodium hydrogen carbonate. The mixture is extracted three times with ethyl acetate, and the organic layer is dried over anhydrous sodium sulfate. The desiccant is removed by filtration, and the filtrate is concentrated under reduced pressure to give the title compound (1.46 g).

(2) 4-(1-t-Butoxycarbonyl-4-piperidy)methylcarbamoylbutanoic Acid

The compound (1.46 g) obtained in the above (1) is dissolved in dichloromethane (20 ml), and thereto are added glutaric anhydride (0.86 g) and triethylamine (1.14 ml), and the mixture is stirred for two hours. To the mixture is added dropwise N-(3-aminopropyl)morpholine (0.3 ml), and the mixture is further stirred for 30 minutes. The mixture is evaporated under reduced pressure to remove the solvent, and thereto is added 10% aqueous citric acid solution, and extracted with ethyl acetate. The organic layer is dried over anhydrous magnesium sulfate, and the desiccant is removed by filtration, and the filtrate is concentrated under reduced pressure to give the title compound (1.54 g).

(3) (2S)-2-Amino-3-t-butoxycarbonylaminopropanoic Acid Ethyl Ester (2S)-2-Benzyloxycarbonylamino-3-t-butoxycarbonylaminopropanoic acid ethyl ester (3.0 g), which is prepared in the same manner as the synthesis of the compound of Example 1-(3), is dissolved in a mixture of ethyl acetate (10 ml) and ethanol (15 ml), and thereto is 10% palladium-carbon (50% wet, 1.5 g), and the mixture is stirred at room temperature for 4.5 hours under hydrogen atmosphere. The insoluble materials are removed by filtration, and the filtrate is concentrated under reduced pressure to give the title compound (1.84 g) as an oily product.

(4) (2S)-2-Benzenesulfonylamino-3-t-butoxycarbonylaminopropanoic Acid Ethyl Ester The compound obtained in the above (3) is dissolved in dichloromethane (15 ml), and thereto are added triethylamine (2.0 ml) and benzenesulfonyl chloride (1.57 ml) at room temperature, and the mixture is stirred for 30 minutes. To the mixture are further added triethylamine (0.57 ml) and benzenesulfonyl chloride (0.52 ml), and the mixture is further stirred for 30 minutes. The reaction mixture is poured into water, and the mixture is extracted three times with ethyl acetate. The extract is washed successively with 1N hydrochloric acid (twice), a saturated brine (once), a saturated aqueous sodium hydrogen carbonate solution (twice) and a saturated brine (twice), and dried over anhydrous magnesium sulfate. The desiccant is removed by filtration, and the filtrate is concentrated under reduced pressure. The residue is purified by silica gel column chromatography (silica gel; 100 g, solvent; hexane/ethyl acetate=1:1). The fractions containing the title compound are concentrated under reduced pressure to give the title compound (2.69 g) as a colorless powder.

(5) (2S)-2-Benzenesulfonylamino-3-(4-((1-t-butoxycarbonyl-4-piperidyl)methylcarbamoyl)butanoylamino)propanoic Acid Ethyl Ester The compound (100 mg) obtained in the above (4) is dissolved in acetonitrile (3 ml) and thereto is added dropwise methanesulfonic acid (87 µl) under ice-cooling, and the mixture is stirred for one hour. To the mixture are added successively DMF (3 ml), triethylamine (150 µl), the compound (100 mg) obtained in the above (2), HOBT.H$_2$O (40 mg) and WSC.HCl (60 mg) under ice-cooling, and further thereto is added dropwise triethylamine (37 µl), and the mixture is stirred at room temperature for 20 hours. The reaction mixture is poured into water, and the mixture is extracted three times with ethyl acetate. The organic layer is washed successively with a saturated aqueous sodium hydrogen carbonate solution (twice), 10% aqueous citric acid solution (twice), and a saturated brine (twice), and dried over anhydrous magnesium sulfate. The desiccant is removed by filtration, and the filtrate is concentrated under reduced pressure to give the title compound (160 mg).

(6) (2S)-2-Benzenesulfonylamino-3-(4-(4-piperidylmethylcarbamoyl)butanoylamino)propanoic Acid TFA Salt The compound (160 mg) obtained in the above (5) is dissolved in ethanol (3 ml) and thereto is added an aqueous solution of lithium hydroxide (LiOH; 60 mg, water; 3 ml), and the mixture is stirred at room temperature for 3 hours. The mixture is evaporated under reduced pressure to remove the solvent, and the pH value of the residue is adjusted to pH 2 with 10% aqueous citric acid solution, and extracted three times with ethyl acetate. The extract is washed twice with a saturated brine, and dried over anhydrous magnesium sulfate. The desiccant is removed by filtration, and the filtrate is concentrated under reduced pressure. The residue is dissolved in TFA (5 ml) under ice-cooling, and the mixture is stirred for 40 minutes. The reaction mixture is concentrated under reduced pressure, and the residue is purified by HPLC to give a white powder (126 mg).

MS (SIMS): 455 [M+1]$^+$. HPLC retention time: 14.7 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.25 (2H, m), 1.58–1.76 (5H, m), 1.92–2.06 (4H, m), 2.81 (2H, m), 2.95 (2H, t, J=6.3 Hz), 3.07 (1H, m), 3.27 (3H, m), 3.86 (1H, m), 7.57 (3H, m), 7.75 (2H, m), 7.85 (2H, m), 8.13 (1H, d, J=8.9 Hz), 8.15 (1H, m), 8.49 (1H, m).

Example 55

Synthesis of (2S)-2-benzenesulfonylamino-3-(3-(2-(4-piperidyloxy)ethanoylamino)propanoylamino) propanoic Acid TFA Salt (1) 2-(1-Benzyloxycarbonyl-4-piperidyl)oxyacetic Acid t-Butyl 2-(1-benzyloxycarbonyl-4-piperidyl)oxyacetate (11.0 g), which is prepared by the method disclosed in J. Med. Chem., 35, 4393 (1992), is stirred in 4N hydrogen chloride/dioxane at room temperature for four hours, and the mixture is evaporated under reduced pressure to remove the solvent to give the title compound (9.2 g) as a pale yellow oil.

$^1$H-NMR (CDCl$_3$) δ (ppm): 1.52–1.70 (2H, m), 1.78–1.96 (2H, m), 3.15–3.28 (2H, m), 3.56–3.68 (1H, m), 3.74–3.92 (2H, m), 4.17 (2H, s), 5.15 (2H, s), 7.28–7.42 (5H, m).

(2) (2S)-2-Benzenesulfonylamino-3-(3-(2-(1-benzyloxycarbonyl-4-piperidyl)oxyethanoylamino) propanoylamino)propanoic Acid Ethyl Ester (2S)-2-Benzenesulfonylamino-3-(3-(t-butoxycarbonylamino)propanoylamino)propanoic acid ethyl ester (100 mg), which is prepared in the same manner as the synthesis of the compound of Example 1-(5), is subjected to de-t-butoxycarbonylation in the same manner as in Example 1-(8), and the resulting compound is condensed with the compound (73 mg) obtained in the above (1) to give the title compound (144 mg).

(3) (2S)-2-Benzenesulfonylamino-3-(3-(2-(1-benzyloxycarbonyl-4-piperidyl)oxyethanoylamino) propanoylamino)propanoic Acid The compound (144 mg) obtained in the above (2) is dissolved in DMF (3 ml), and thereto is added 1N aqueous sodium hydroxide solution (698 μl) under ice-cooling, and the mixture is stirred for 1.5 hour. The pH value thereof is adjusted to pH 2 with 10% aqueous citric acid solution, and extracted three times with ethyl acetate. The extract is washed twice with a saturated brine, and dried over anhydrous magnesium sulfate. The desiccant is removed by filtration, and the filtrate is concentrated under reduced pressure to give the title compound (92 mg).

(4) (2S)-2-Benzenesulfonylamino-3-(3-(2-(4-piperidyl) oxyethanoylamino)propanoylamino)propanoic Acid TFA Salt The compound (92 mg) obtained in the above (3) is dissolved in methanol (20 ml), and thereto are added acetic acid (100 μl) and 10% palladium-carbon (50% wet, 100 mg), and the mixture is stirred at room temperature for three hours under hydrogen atmosphere. The insoluble materials are removed by filtration, and the filtrate is evaporated under reduced pressure to remove the solvent. The residue is purified by HPLC to give a white powder (31 mg).

MS (SIMS): 483 [M+1]$^+$. HPLC retention time: 14.8 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.65–1.80 (2H, m), 1.85–2.00 (2H, m), 2.10–2.25 (2H, m), 2.90–3.40 (7H, m), 3.45–4.20 (5H, m), 7.50–7.65 (3H, m), 7.70–7.80 (3H, m), 7.98–8.16 (1H, m), 8.15 (1H, d, J=9 Hz), 8.46 (2H, s).

The chemical structures of the compounds obtained in Examples 53 to 55 are as follows.

Example 53

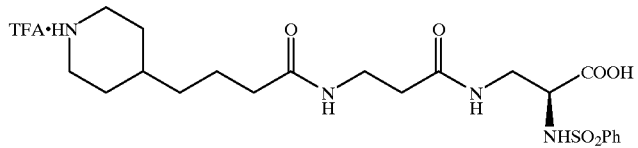

Example 54

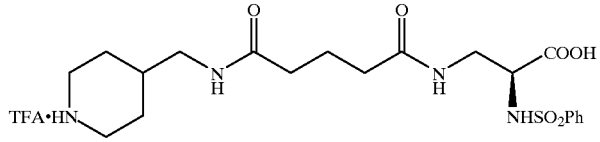

Example 55

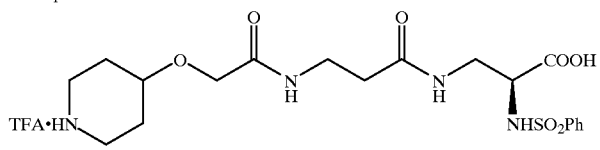

Example 56

Synthesis of (2S)-3-(4-(4-amidinophenoxy) butanoylamino)-2-butanesulfonylaminopropanoic Acid TFA Salt (1) 4-(4-Cyanophenoxy)butanoic Acid Ethyl Ester 4-Cyanophenol (5.0 g) is dissolved in DMF (6 ml), and thereto are added ethyl 4-bromobutanate (7.94 ml) and potassium carbonate (6.4 g), and the mixture is stirred at room temperature for 74 hours. The reaction mixture is poured into water, and the colorless precipitates are collected by filtration and washed with water to give the title compound (9.5 g).

$^1$H-NMR (CDCl$_3$) δ (ppm): 1.26 (3H, t, J=7 Hz), 2.05–2.25 (2H, m), 2.52 (2H, t, J=7 Hz), 4.07 (2H, t, J=6.3 Hz), 4.15 (2H, q, J=7 Hz), 6.94 (2H, d, J=9.2 Hz), 7.58 (2H, d, J=9.2 Hz).

(2) 4-(4-Amidinophenoxy)butanoic Acid Ethyl Ester Hydroiodide

The compound (3 g) obtained in the above (1) is dissolved in a mixture of pyridine (75 ml) and triethylamine (15 ml), and thereto is blown hydrogen sulfide gas for 30 minutes under ice-cooling. To the mixture is further blown hydrogen sulfide gas for three hours at room temperature, and the mixture is stirred for 20 hours. The hydrogen sulfide is removed by blowing nitrogen gas into the mixture, and the mixture is concentrated under reduced pressure. The residue is dissolved in acetone (60 ml) and thereto is added methyl iodide (5 ml), and the mixture is heated with stirring at 50° C. for 30 minutes. After cooling, the mixture is concentrated under reduced pressure, and the residue is dissolved in methanol (100 ml) and thereto is added ammonium acetate (2.05 g). The mixture is heated with stirring at 70° C. for 3.5 hours. After cooling, nitrogen gas is blown into the mixture, and the mixture is concentrated under reduced pressure. Ether is added to the residue, and the precipitates are collected by filtration to give the title compound (2.74 g).

MS (SIMS): 251 [M+1]$^+$. $^1$H-NMR (CD$_3$OD) δ (ppm): 1.16 (3H, t, J=7 Hz), 1.95–2.1 (2H, m), 2.45 (2H, t, J=7.3 Hz), 4.0–4.15 (4H, m), 7.05 (2H, d, J=9.2 Hz), 7.71 (2H, d, J=9.2 Hz).

(3) 4-(4-Amidinophenoxy)butanoic Acid

The compound (500 mg) obtained in the above (2) is dissolved in a mixture of 1N hydrochloric acid (5 ml) and acetic acid (5 ml), and the mixture is stirred at 50° C. for 8 hours. The reaction mixture is concentrated under reduced pressure, and the residue is dried to give the title compound (388 mg) as a brown solid.

MS (SIMS): 323 [M+1]$^+$. $^1$H-NMR (CD$_3$OD) δ (ppm): 1.95–2.1 (2H, m), 2.43 (2H, t, J=7.3 Hz), 4.08 (2H, t, J=6.3 Hz), 7.06 (2H, d, J=9 Hz), 7.71 (2H, d, J=9 Hz).

(4) (2S)-2-Butanesulfonylamino-3-t-butoxycarbonylaminopropanoic Acid Ethyl Ester The title compound is prepared from the compound (350 mg) obtained in Example 54-(3) by using butanesulfonyl chloride in the same manner as in Example 54-(4).

Yield: 438 mg. $^1$H-NMR (CDCl$_3$) δ (ppm): 0.94 (3H, t, J=7 Hz), 1.31 (3H, t, J=7 Hz), 1.44 (9H, s), 1.35–1.55 (2H, m), 1.7–1.9 (2H, m), 2.95–3.1 (2H, m), 3.4–3.65 (2H, m), 4.1–4.35 (3H, m), 4.94 (1H, bs), 5.42 (1H, bd, J=8.3 Hz).

(5) (2S)-3-(4-(4-Amidinophenoxy)butanoylamino)-2-butanesulfonylaminopropanoic Acid TFA Salt The compound (151 mg) obtained in the above (4) is dissolved in acetonitrile (1.5 ml) and thereto is added a solution of methanesulfonic acid (206 mg) in acetonitrile (0.8 ml) under ice-cooling, and the mixture is stirred at room temperature for 30 minutes. To the reaction mixture are added successively DMF (2 ml), triethylamine (300 μl), the compound (133 mg) obtained in the above (3), HOBT.H$_2$O (80 mg) and WSC.HCl (100 mg) under ice-cooling, and the mixture is stirred at room temperature for 22 hours. The reaction mixture is concentrated under reduced pressure.

The residue is washed with ether, and thereto is added a mixture of 1N hydrochloric acid (10 ml) and acetic acid (10 ml), and the mixture is stirred at 60° C. for 16 hours. The reaction mixture is concentrated under reduced pressure, and the residue is purified by HPLC to give the title compound (92 mg) as a colorless powder.

MS (SIMS): 429 [M+1]$^+$. HPLC retention time: 20.1 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 0.87 (3H, t, J=7.3 Hz), 1.30–1.50 (2H, m), 1.55–1.80 (2H, m), 1.90–2.10 (2H, m), 2.25 (2H, t, J=8 Hz), 2.90–3.05 (2H, m), 3.10–3.30 (1H, m), 3.35–3.50 (1H, m), 3.90–4.05 (1H, m), 4.08 (2H, t, J=6.6 Hz), 7.15 (2H, d, J=8.9 Hz), 7.54 (1H, d, J=8.9 Hz), 7.80 (2H, d, J=8.9 Hz), 8.05 (1H, bt, J=6 Hz), 8.82 (2H, bs), 9.12 (2H, bs).

Example 57

Synthesis of (2S)-3-(4-(4-amidinophenoxy) butanoylamino)-2-(4-methoxy) benzenesulfonylaminopropanoic Acid TFA Salt (1) (2S)-3-t-Butoxycarbonylamino-2-(4-methoxy) benzenesulfonylaminopropanoic Acid Ethyl Ester The title compound is prepared from the compound (300 mg) obtained in Example 54-(3) by using 4-methoxybenzenesulfonyl chloride in the same manner as in Example 54-(4).

Yield: 500 mg. $^1$H-NMR (CDCl$_3$) δ (ppm): 1.15 (3H, t), 1.42 (9H, s), 3.46 (2H, m), 3.86 (3H, s), 3.85–4.10 (1H, m), 4.02 (2H, q, J=7 Hz), 4.92 (1H, bs), 5.49 (1H, bd, J=7.6 Hz), 6.96 (2H, d, J=8.9 Hz), 7.77 (2H, d, J=8.9 Hz).

(2) (2S)-3-(4-Amidinophenoxy)butanoylamino)-2-(4-methoxy)benzenesulfonylaminopropanoic Acid TFA Salt The title compound is prepared from the compound (133 mg) obtained in Example 56-(3) and the compound (172 mg) obtained in the above (1) in the same manner as in Example 56-(5).

Yield: 100 mg. MS (SIMS): 479 [M+1]$^+$. HPLC retention time: 22.3 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.80–2.00 (2H, m), 2.10–2.25 (2H, m), 3.00–3.20 (1H, m), 3.25–3.40 (1H, m), 3.80–3.95 (1H, m), 3.81 (3H, s), 4.05 (2H, t, J=6 Hz), 7.06 (2H, d, J=9 Hz), 7.14 (2H, d, J=8.9 Hz), 7.69 (2H, d, J=9 Hz), 7.80 (2H, d, J=8.9 Hz), 7.90–8.10 (2H, m), 8.87 (2H, bs), 9.13 (2H, bs).

Example 58

Synthesis of (2S)-3-(4-(4-amidinophenoxy) butanoylamino)-2-benzenesulfonylaminopropanoic Acid TFA Salt The title compound is prepared in the same manner as in Example 57.

Yield: 47 mg. MS (SIMS): 449 [M+1]$^+$. HPLC retention time: 16.6 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 2%/min.). $^1$H-NMR (DMSO-d$_6$) δ (ppm): 1.80–2.00 (2H, m), 2.10–2.25 (2H, m), 3.00–3.20 (1H, m), 3.225–3.50 (1H, m), 3.85–4.00 (1H, m), 4.05 (2H, t, J=6.3 Hz), 7.15 (2H, d, J=8.9 Hz), 7.50–7.70 (3H, m), 7.70–7.90 (4H, m), 7.95–8.05 (1H, m), 8.15 (1H, d, J=8.9 Hz), 8.89 (2H, bs), 9.13 (2H, bs).

Example 59

Synthesis of (2S)-(3-(4-(4-amidinophenoxy) butanoylamino)-2-(2-nitro) benzenesulfonylaminopropanic Acid TFA Salt The title compound is prepared in the same manner as in Example 57.

Yield: 61 mg. MS (SIMS): 494 [M+1]$^+$. HPLC retention time: 23.5 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.80–2.00 (2H, m), 2.15–2.30 (2H, m), 3.15–3.35 (1H, m), 3.24–3.60 (1H, m), 4.00–4.15 (3H, m), 7.14 (2H, d, J=8.9 Hz), 7.70–8.15 (7H, m), 8.42 (1H, d, J=8.9 Hz), 9.03 (2H, bs), 9.13 (2H, bs).

Example 60

Synthesis of (2S)-3-(4-(4-amidinophenoxy) butanoylamino)-2-(2,4,6-trimethyl) benzenesulfonylaminopropanic Acid TFA Salt The title compound is prepared in the same manner as in Example 57.

Yield: 43 mg. MS (SIMS): 491 [M+1]$^+$. HPLC retention time: 29.4 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.75–1.95 (2H, m), 2.00–2.20 (2H, m), 2.19 (3H, s), 2.50 (6H, s), 3.00–3.20 (1H, m), 3.25–3.40 (1H, m), 3.70–3.90 (1H, m), 4.01 (2H, t, J=6 Hz), 6.94 (2H, s), 7.11 (2H, d, J=8.9 Hz), 7.77 (2H, d, J=8.9 Hz), 7.85–8.00 (2H, m), 8.88 (2H, bs), 9.09 (2H, bs).

Example 61

Synthesis of (2S)-3-(4-(4-amidinophenoxy) butanoylamino)-2-(4-fluoro) benzenesulfonylaminopropanic Acid TFA Salt The title compound is prepared in the same manner as in Example 57.

Yield: 220 mg. MS (SIMS): 467 [M+1]$^+$. HPLC retention time: 22.4 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.80–2.00 (2H, m), 2.10–2.25 (2H, m), 3.05–3.20 (1H, m), 3.25–3.40 (1H, m), 3.80–4.00 (1H, m), 4.06 (2H, t, J=6 Hz), 7.15 (2H, d, J=8.9 Hz), 7.40 (2H, dd, J=8.9 Hz), 7.75–7.90 (4H, m), 8.02 (1H, bt, J=5.9 Hz), 8.23 (1H, d, J=9.2 Hz), 8.82 (2H, bs), 9.13 (2H, bs).

Example 62

Synthesis of (2S)-3-(4-(4-amidinophenoxy) butanoylamino)-2-(1-naphthalene) sulfonylaminopropanoic Acid TFA Salt The title compound is prepared in the same manner as in Example 57.

Yield: 67 mg. MS (SIMS): 499 [M+1]$^+$. HPLC retention time: 27.3 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.75–2.10 (4H, m), 3.05–3.20 (1H, m), 3.25–3.40 (1H, m), 3.75–3.90 (1H, m), 4.00 (2H, t, J=6 Hz), 7.13 (2H, d, J=8.9 Hz), 7.55–7.85 (4H, m.), 7.80 (2H, d, J=8.9 Hz), 8.00–8.25 (4H, m), 8.64 (1H, d, J=8.3 Hz), 9.05 (2H, bs), 9.10 (2H, bs).

The chemical structures of the compounds obtained in Examples 56 to 62 are as follows.

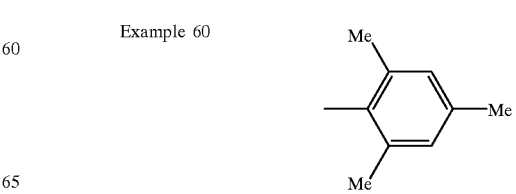

| Example No. | R$^2$ |
|---|---|
| Example 56 | —Bu |
| Example 57 | 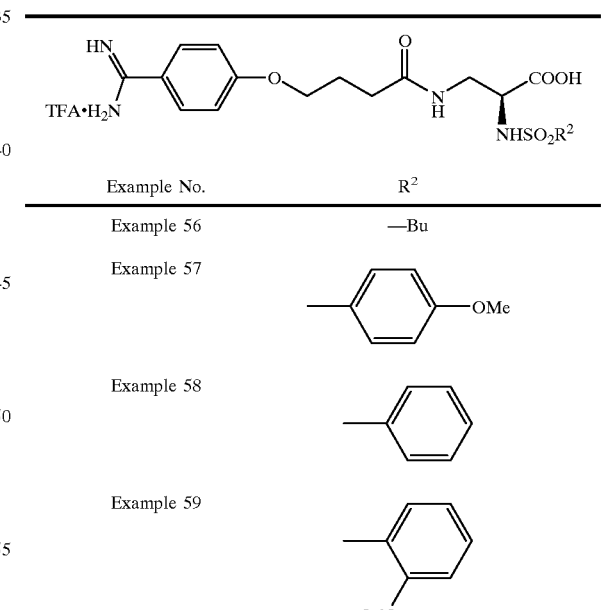 |
| Example 58 | |
| Example 59 | |
| Example 60 | |

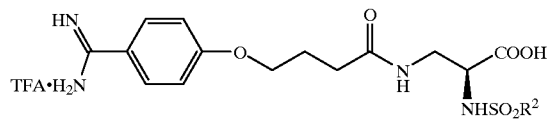

| Example No. | R² |
|---|---|
| Example 61 |  |
| Example 62 | 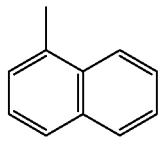 |

Example 63

Synthesis of (2S)-3-(5-(4-amidinophenoxy) pentanoylamino)-2-(4-methoxy) benzenesulfonylaminopropanoic Acid TFA Salt (1) 5-(4-Cyanophenoxy)pentanoic Acid Ethyl Ester 4-Cyanophenol (5.0 g) is dissolved in DMF (40 ml), and thereto are added ethyl 5-bromopentanoate (11.4 g) and potassium carbonate (6.38 g), and the mixture is stirred at room temperature for 24 hours. The reaction mixture is poured into water, and the mixture is extracted three times with ethyl acetate. The organic layer is washed successively with a saturated aqueous sodium hydrogen carbonate solution, water and a saturated brine, and dried over anhydrous magnesium sulfate. The desiccant is removed by filtration, and the filtrate is concentrated under reduced pressure. The residue is purified by silica gel column chromatography (silica gel; 100 g, solvent; hexane/ethyl acetate= 5:1 to 5:2). The fractions containing the title compound are concentrated under reduced pressure to give the title compound (9.86 g).

$^1$H-NMR (CDCl$_3$) δ (ppm): 1.26 (3H, t, J=7 Hz), 1.75–1.95 (4H, m), 2.39 (2H, t, J=6.9 Hz), 4.02 (2H, t, J=5.9 Hz), 4.14 (2H, q, J=7 Hz), 6.93 (2H, d, J=9 Hz), 7.57 (2H, d, J=9 Hz).

(2) 5-(4-Amidinophenoxy)pentanoic Acid

The title compound is prepared from the compound (1.30 g) obtained in the above (1) in the same manner as in Example 56-(2) and -(3).

Yield: 1.66 g. $^1$H-NMR (CD$_3$OD) δ (ppm): 1.6–1.9 (4H, m), 2.31 (2H, t, J=7 Hz), 4.05 (2H, t, J=5.9 Hz), 7.06 (2H, d, J=9 Hz), 7.71 (2H, d, J=9 Hz).

(3) (2S)-3-(5-(4-Amidinophenoxy)pentanoylamino)-2-(4-methoxy)benzenesulfonylaminopropanoic Acid TFA Salt The title compound is prepared from the compound (134 mg) obtained in the above (2) and the compound (154 mg) obtained in Example 57-(1) in the same manner as in Example 56-(5).

Yield: 91 mg. MS (SIMS): 493 [M+1]⁺. HPLC retention time: 24.1 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.50–1.80 (4H, m), 2.00–2.15 (2H, m), 3.00–3.20 (1H, m), 3.20–3.20 (1H, m), 3.75–3.90 (1H, m), 3.81 (3H, s), 4.06 (2H, bt, J=6 Hz), 7.06 (2H, d, J=8.9 Hz), 7.14 (2H, d, J=8.9 Hz), 7.69 (2H, d, J=8.9 Hz), 7.80 (2H, d, J=8.9 Hz), 7.85–8.00 (2H, m), 8.86 (2H, bs), 9.12 (2H, bs).

Example 64

Synthesis of (2S)-3-(5-(4-amidinophenoxy) pentanoylamino)-2-benzenesulfonylaminopropanoic Acid TFA Salt The title compound is prepared in the same manner as in Example 63.

Yield: 283 mg. MS (SIMS): 463 [M+1]⁺. HPLC retention time: 22.5 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 1.50–1.80 (4H, m), 2.00–2.10 (2H, m), 3.00–3.15 (1H, m), 3.25–3.35 (1H, m), 3.80–3.95 (1H, m), 4.06 (2H, bt, J=6 Hz), 7.15 (2H, d, J=8.9 Hz), 7.50–7.65 (3H, m), 7.70–7.85 (4H, m), 7.90 (1H, bt, J=5.6 Hz), 8.12 (1H, d, J=9.2 Hz), 8.90 (2H, bs), 9.12 (2H, bs).

Example 65

Synthesis of (2S)-3-(5-(4-amidinophenoxy) pentanoylamino)-2-butanesulfonylaminopropanoic Acid TFA Salt The title compound is prepared in the same manner as in Example 63.

Yield: 324 mg. MS (SIMS): 443 [M+1]⁺. HPLC Retention time: 22.1 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 0.84 (3H, t, J=7 Hz), 1.25–1.45 (2H, m), 1.50–1.80 (6H, m), 2.15 (2H, bt, J=7 Hz), 2.90–3.00 (2H, m), 3.15–3.50 (2H, m), 3.90–4.00 (1H, m), 4.07 (2H, bt, J=6 Hz), 7.14 (2H, d, J=8.9 Hz), 7.53 (1H, d, J=9.2 Hz), 7.81 (2H, d, J=8.9 Hz), 7.99 (1H, bt, J=6 Hz), 8.95 (2H, bs), 9.12 (2H, bs).

Example 66

Synthesis of (2S)-3-(5-(4-amidinophenyl) pentanoylamino)-2-(4-methoxy) benzenesulfonylaminopropanoic Acid TFA Salt (1) 5-(4-Cyanophenyl)pentanoic Acid 4-Bromobenzonitrile (2.82 g) is dissolved in DMF (17 ml), and thereto are added tetrabutylammonium chloride (2.83 g), which is made anhydrous form by azeothropic distillation in benzene, triphenylphosphine (137 mg), palladium (II) acetate (117 mg) and potassium acetate (6.13 g), and thereto is added dropwise a solution of 4-pentenoic acid (1.05 g) in DMF (6 ml). The mixture is stirred at room temperature for 24 hours, and poured into 3% aqueous sodium hydrogen carbonate solution (70 ml), and the aqueous layer is washed with ethyl acetate. The pH value of the aqueous layer is adjusted to pH 2 with 10% hydrochloric acid, and extracted with ethyl acetate. The organic layer is washed with a saturated brine, and dried over anhydrous magnesium sulfate. The desiccant is removed by filtration, and the filtrate is concentrated under reduced pressure.

The residue (816 mg) is dissolved in methanol (50 ml), and thereto is added 5% palladium-calcium carbonate (100 mg), and the mixture is stirred for one hour under hydrogen atmosphere. The insoluble materials are removed by filtration, and the filtrate is concentrated under reduced pressure to give the title compound (824 mg).

$^1$H-NMR (CD$_3$OD) δ (ppm): 1.45–1.70 (4H, m), 2.15–2.3 (2H, m), 2.55–2.7 (2H, m), 7.30 (2H, d, J=8 Hz), 7.54 (2H, d, J=8 Hz).

(2) (2S)-3-(5-(4-Cyanophenyl)pentanoylamino)-2-(4-methoxy)benzenesulfonylaminopropanoic Acid Ethyl Ester The compound (140 mg) obtained in Example 57-(1) is dissolved in acetonitrile (1.5 ml), and thereto is added a solution of methanesulfonic acid (168 mg) in acetonitrile (0.8 ml) under ice-cooling, and the mixture is stirred at room temperature for 30 minutes. To the reaction mixture are added successively DMF (1 ml), triethylamine (240 μl), the compound (85 mg) obtained in the above (1), HOBT.H$_2$O (64 mg) and WSC.HCl (81 mg) under ice-cooling, and the mixture is stirred at room temperature for 5 hours. The mixture is poured into water, and the mixture is extracted three times with ethyl acetate. The organic layer is washed successively with a saturated aqueous sodium hydrogen carbonate solution (twice), 10% aqueous citric acid solution (twice) and a saturated brine (twice), and dried over anhydrous magnesium sulfate. The desiccant is removed by filtration, and the filtrate is concentrated under reduced pressure. The residue is purified by silica gel column chromatography (silica gel; 30 g, solvent; chloroform/methanol= 25:1). The fractions containing the title compound are concentrated under reduced pressure to give the title compound (133 mg).

$^1$H-NMR (CDCl$_3$) δ (ppm): 1.13 (3H, t, J=7 Hz), 1.55–1.75 (4H, m), 2.15–2.3 (2H, m), 2.6–2.75 (2H, m), 3.4–3.75 (2H, m), 3.86 (3H, s), 3.85–4.05 (1H, m), 4.01 (2H, q, J=7 Hz), 5.80 (1H, bd, J=8.3 Hz), 6.25 (1H, bt, J=5.9 Hz), 6.95 (2H, d, J=8.9 Hz), 7.27 (2H, d, J=8 Hz), 7.55 (2H, d, J=8 Hz), 7.76 (2H, d, J=8.9 Hz).

(3) (2S)-3-(5-(4-Amidinophenyl)pentanoylamino)-2-(4-methoxy)benzenesulfonylaminopropanoic Acid Ethyl Ester Hydroiodide The title compound is prepared from the compound (130 mg) obtained in the above (2) in the same manner as in Example 56-(2).

Yield: 150 mg.

(4) (2S)-3-(5-(4-Amidinophenyl)pentanoylamino)-2-(4-methoxy)benzenesulfonylaminopropanoic Acid TFA Salt To the compound (150 mg) obtained in the above (3) is added a mixture of 1N hydrochloric acid (7 ml) and acetic acid (7 ml), and the mixture is heated with stirring at 60° C. for 22 hours. The reaction mixture is concentrated under reduced pressure, and the residue is purified by HPLC to give the title compound (11 mg) as a colorless powder.

MS (SIMS): 477 [M+1]$^+$. HPLC retention time: 12.5 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 20% at a rate of 2%/min.). $^1$H-NMR (DMSO-d$_6$) δ (ppm): 1.35–1.65 (4H, m), 1.95–2.10 (2H, m), 2.66 (2H, t, J=7 Hz), 3.00–3.20 (1H, m), 3.20–3.40 (1H, m), 3.70–3.85 (1H, m), 3.82 (3H, s), 7.06 (2H, d, J=8.9 Hz), 7.44 (2H, d, J=8 Hz), 7.69 (2H, d, J=8.9 Hz), 7.73 (2H, d, J=8 Hz), 7.80–7.95 (2H, m), 9.02 (2H, bs), 9.22 (2H, bs).

Example 67

Synthesis of (2S)-3-(5-(4-amidinophenyl) pentanoylamino-2-benzenesulfonylaminopropanoic Acid TFA Salt The title compound is prepared in the same manner as in Example 66.

Yield: 39 mg. MS (SIMS): 447 [M+1]$^+$. HPLC retention time: 11.5 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 20% at a rate of 2%/min.). $^1$H-NMR (DMSO-d$_6$) δ (ppm): 1.35–1.65 (4H, m), 1.95–2.10 (2H, m), 2.66 (2H, t, J=7 Hz), 3.00–3.20 (1H, m), 3.20–3.40 (1H, m), 3.80–3.95 (1H, m), 7.40–7.95 (10H, m), 8.13 (1H, d, J=8.9 Hz), 9.03 (2H, bs), 9.23 (2H, bs).

The chemical structures of the compounds obtained in Example 63 to 67 are as follows.

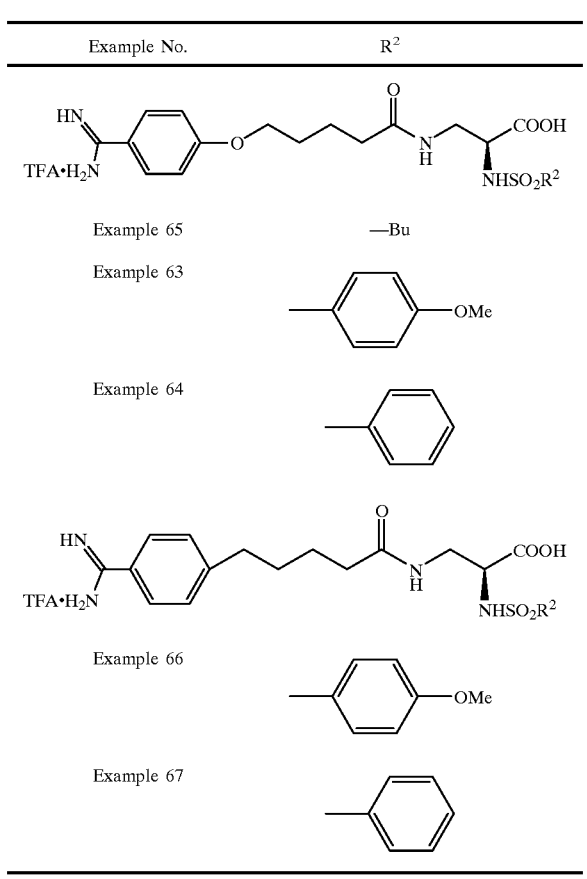

Example 68

Synthesis of (2S)-3-(2-(4'-amidino-4-biphenylyl) ethanoylamino)-2-(4-methoxy) benzenesulfonylaminopropanoic Acid TFA Salt (1) 4'-Bromo-4-acetylbiphenyl 4-Bromobiphenyl (35 g) is dissolved in nitrobenzene (200 ml), and thereto is added aluminum chloride (25 g) under ice-cooling, and the mixture is stirred at room temperature for four hours. The reaction mixture is poured into a mixture of 12N hydrochloric acid (150 ml) and ice-water (150 ml), and extracted with chloroform. The organic layer is washed with water, and dried over anhydrous magnesium sulfate. The desiccant is removed by filtration, and the filtrate is concentrated under reduced pressure. The residue is recrystallized from acetone-ethanol to give the title compound (33.5 g).

(2) 4'-Bromo-4-carboxymethylbiphenyl

The compound (3 g) obtained in the above (1) is suspended in morpholine (20 ml), and thereto is added sulfur (0.71 g), and the mixture is refluxed with stirring for five hours. After cooling, the reaction mixture is poured into water, and extracted with ethyl acetate. The organic layer is washed with 1N hydrochloric acid (twice) and a saturated brine (twice), and dried over anhydrous sodium sulfate. The desiccant is removed by filtration, and the filtrate is concentrated under reduced pressure. The residue is suspended in ethanol, and the precipitates are collected by filtration.

The precipitates (3.32 g) are suspended in a mixture of ethanol (40 ml) and 20% aqueous sodium hydroxide solution (7 ml), and the mixture is refluxed with stirring for 3.5 hours. After cooling, the mixture is evaporated to remove the solvent, and the pH value of the residue is adjusted to pH 1 to 2 with 1N hydrochloric acid, and extracted twice with ethyl acetate. The organic layer is washed with a saturated brine, and dried over anhydrous magnesium sulfate. The desiccant is removed by filtration, and the filtrate is concentrated under reduced pressure. The residue is suspended in ethanol, and the precipitates are collected by filtration to give the title compound (840 mg) as a pale yellow powder.

(3) 4'-Cyano-4-carboxymethylbiphenyl

The compound (840 mg) obtained in the above (2) is dissolved in DMF (7 ml), and thereto are added pyridine (10 µl) and cuprous cyanide (I) (410 mg), and the mixture is refluxed with stirring for 8 hours. To the mixture is further added cuprous cyanide (I) (410 mg), and the mixture is refluxed with stirring for 7.5 hours. After cooling, to the mixture is added a mixture of conc. aqueous ammonia (5 ml) and water (60 ml), and the precipitates are removed by filtration. The filtrate is concentrated under reduced pressure, and the pH value of the residue is adjusted to pH 11 with 1N aqueous sodium hydroxide solution, and washed twice with ether. The pH value of the residue is adjusted to pH 1 with conc. hydrochloric acid, and extracted three times with ethyl acetate. The organic layer is washed with a saturated brine, and dried over anhydrous magnesium sulfate. The desiccant is removed by filtration, and the filtrate is concentrated under reduced pressure to give the title compound (654 mg).

$^1$H-NMR (CDCl$_3$) δ (ppm): 3.72 (2H, s), 7.43 (2H, d, J=9 Hz), 7.53 (2H, d, J=9 Hz), 7.62–7.78 (4H, m).

(4) (2S)-3-(2-(4'-Cyano-4-biphenylyl)ethanoylamino)-2-(4-methoxy)benzenesulfonylaminopropanoic Acid Ethyl Ester The compound (300 mg) obtained in Example 57-(1) is subjected to de-t-butoxycarbonylation in the same manner as in Example 66-(2), and the resultant is condensed with the compound (284 mg) obtained in the above (3) to give the title compound (350 mg).

(5) (2S)-3-(2-(4'-Amidino-4-biphenylyl)ethanoylamino)-2-(4-methoxy)benzenesulfonylaminopropanoic Acid Ethyl Ester Hydroiodide The title compound is prepared from the compound (350 mg) obtained in the above (4) in the same manner as in Example 56-(2).

Yield: 181 mg.

(6) (2S)-3-(2-(4'-Amidino-4-biphenylyl)ethanoylamino)-2-(4-methoxy)benzenesulfonylaminopropanoic Acid TFA Salt The title compound is prepared from the compound (181 mg) obtained in the above (5) in the same manner as in Example 66-(4).

Yield: 95 mg. MS (SIMS): 511 [M+1]$^+$. HPLC retention time: 29.0 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). $^1$H-NMR (DMSO-d$_6$) δ (ppm): 3.05–3.50 (4H, m), 3.81 (3H, s), 3.75–3.90 (1H, m), 7.08 (2H, d, J=9 Hz), 7.35 (2H, d, J=9 Hz), 7.68–7.77 (4H, m), 7.87–8.03 (5H, m), 8.21 (1H, bs), 9.00–9.42 (4H, m).

Example 69

Synthesis of (2S)-3-(2-(1-(4-amidinophenyl)-4-piperidyl)ethanoylamino)-2-benzenesulfonylaminopropanoic Acid TFA Salt (1) 4-Carboxyethoxymethylpiperidine Hydrochloride The compound (2.19 g) obtained in Example 6-(1) is dissolved in 4N hydrogen chloride-dioxane (30 ml), and the mixture is stirred at room temperature for 30 minutes. The reaction mixture is concentrated under reduced pressure to give the title compound (1.77 g) as a colorless powder.

(2) 2-(1-(4-Cyanophenyl)-4-piperidyl)ethanoic Acid Ethyl Ester

The compound (1.77 g) obtained in the above (1) is dissolved in DMSO (30 ml), and thereto are added 4-chlorobenzonitrile (982 mg), and sodium carbonate (3.03 g), and the mixture is heated with stirring at 160° C. for 12.5 hours. After cooling, the reaction mixture is poured into water, and extracted three times with chloroform. The organic layer is washed with a saturated brine, and dried over anhydrous magnesium sulfate. The desiccant is removed by filtration, and the filtrate is concentrated under reduced pressure. The residue is purified by silica gel column chromatography (silica gel; 100 g, solvent; hexane/ethyl acetate=3:1). The fractions containing the title compound are concentrated under reduced pressure to give the title compound (1.38 g) as an oily product.

$^1$H-NMR (CDCl$_3$) δ (ppm): 1.27 (3H, t, J=7 Hz), 1.35 (2H, m), 1.90 (2H, m), 2.10 (1H, m), 2.27 (2H, d, J=6.9 Hz), 2.90 (2H, m), 3.86 (2H, m), 4.15 (2H, q, J=7 Hz), 6.85 (2H, d, J=9 Hz), 7.47 (2H, d, J=9 Hz).

(3) 2-(1-(4-Cyanophenyl)-4-piperidyl)ethanoic Acid

The compound (1.38 g) obtained in the above (2) is dissolved in a mixture of methanol (20 ml) and THF (10 ml), and thereto is added an aqueous sodium hydroxide solution (NaOH; 2.1 g, water; 10 ml), and the mixture is stirred at room temperature for 30 minutes. The pH value of the mixture is adjusted to pH 1 with conc. hydrochloric acid, and the reaction mixture is concentrated under reduced pressure. To the residue is added isopropanol, and the mixture is stirred at room temperature for one hour, and the precipitates are removed by filtration. The filtrate is concentrated under reduced pressure to give the title compound (1.20 g) as a powder.

(4) (2S)-2-Benzenesulfonylamino-3-(2-(1-(4-cyanophenyl)-4-piperidyl)ethanoylamino)propanoic Acid Ethyl Ester The compound (300 mg) obtained in Example 54-(4) is subjected to de-t-butoxycarbonylation in the same manner as in Example 66-(2), and the resultant is condensed with the compound (236 mg) obtained in the above (3) to give the title compound (411 mg).

¹H-NMR (CDCl₃) δ (ppm): 1.15 (3H, t, J=8.9 Hz), 1.30–2.30 (7H, m), 2.90 (2H, m), 3.40–4.20 (7H, m), 5.68 (1H, m), 6.10 (1H, m), 6.85 (2H, d, J=9 Hz), 7.40–7.70 (5H, m), 7.85 (2H, d, J=9 Hz).

(5) (2S)-3-(2-(1-(4-Amidinophenyl)-4-piperidyl)ethanoylamino)-2-benzenesulfonylaminopropanoic Acid Ethyl Ester Hydroiodide The title compound is prepared from the compound (411 mg) obtained in the above (4) in the same manner as in Example 56-(2).

Yield: 739 mg.

(6) (2S)-3-(2-(1-(4-Amidinophenyl)-4-piperidyl)ethanoylamino)-2-benzenesulfonylaminopropanoic Acid TFA Salt The title compound is prepared from the compound (739 mg) obtained in the above (5) in the same manner as in Example 66-(4).

Yield: 150 mg. MS (SIMS): 488 [M+1]⁺. HPLC retention time: 22.9 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). ¹H-NMR (DMSO-d₆) δ (ppm): 1.05–1.22 (2H, m), 1.60–1.78 (2H, m), 1.82–2.00 (3H, m), 2.87–2.95 (2H, m), 3.05–3.18 (1H, m), 3.21–3.37 (1H, m), 3.83–4.00 (3H, m), 7.04 (2H, d, J=9 Hz), 7.50–7.80 (7H, m), 7.93 (1H, t, J=6 Hz), 8.14 (1H, d, J=9 Hz), 8.54 (2H, bs), 8.88 (2H, s).

Example 70

Synthesis of (2S)-2-(4-methoxy)benzenesulfonylamino-3-(1-(3-(4-piperidyl)propanoyl)-3-piperidylcarbonylamino)propanoic Acid TFA Salt (1) N-t-Butoxycarbonylnipecotic Acid Nipecotic acid (5.0 g) is suspended in a mixture of 1,4-dioxane (30 ml) and aqueous sodium hydroxide solution (NaOH; 1.6 g, water; 30 ml), and thereto is added (Boc)₂O (9.3 g) under ice-cooling, and the mixture is stirred for five hours. The reaction mixture is washed with ether, and the pH value of the mixture is adjusted to pH 1 with 1N hydrochloric acid, and extracted twice with ethyl acetate. The organic layer is washed with a saturated brine, and dried over anhydrous magnesium sulfate. The desiccant is removed by filtration, and the filtrate is concentrated under reduced pressure to give the title compound (8.78 g) as a colorless powder.

(2) (2S)-3-(1-t-Butoxycarbonyl-3-piperidyl)carbonylamino-2-(4-methoxy)benzenesulfonylaminopropanoic Acid Ethyl Ester The compound (300 mg) obtained in Example 57-(1) is subjected to de-t-butoxycarbonylation in the same manner as in Example 66-(2), and the resultant is condensed with the compound (178 mg) obtained in the above (1) to give the title compound (440 mg).

(3) (2S)-3-(1-(3-(1-t-Butoxycarbonyl-4-piperidyl)propanoyl)-3-piperidyl)carbonylamino-2-(4-methoxy)benzenesulfonylaminopropanoic Acid Ethyl Ester The compound (440 mg) obtained in the above (2) is subjected to de-t-butoxycarbonylation in the same manner as in Example 66-(2), and the resultant is condensed with the compound (249 mg) obtained in Example 2-(3) to give the title compound (600 mg).

(4) (2S)-2-(4-Methoxy)benzenesulfonylamino-3-(1-(3-(4-piperidyl)propanoyl)-3-piperidyl)carbonylaminopropanoic Acid TFA Salt The title compound is prepared from the compound (600 mg) obtained in the above (3) in the same manner as in Example 2-(7) to give the title compound as a colorless powder.

Yield: 388 mg. MS (SIMS): 525 [M+1]⁺. HPLC retention time: 23.80 min., 24.5 min. (diastereomer mixture). (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 1%/min.). ¹H-NMR (DMSO-d₆) δ (ppm): 1.10–1.88 (11H, m), 1.95–2.62 (5H, m), 2.70–3.90 (11H, m), 4.10–4.40 (1H, m), 7.07 (2H, d, J=9 Hz), 7.69 (2H, d, J=9 Hz), 7.90–8.10 (2H, m), 8.20 (1H, bs), 8.50 (1H, bs).

The chemical structures of the compounds obtained in Example 68 to 70 are as follows.

Example 68

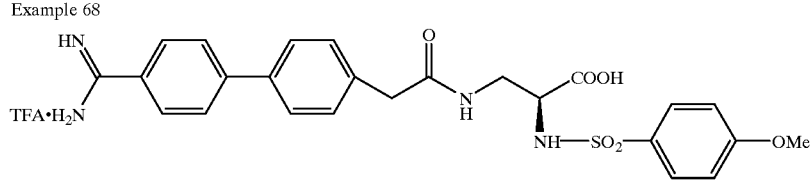

Example 69

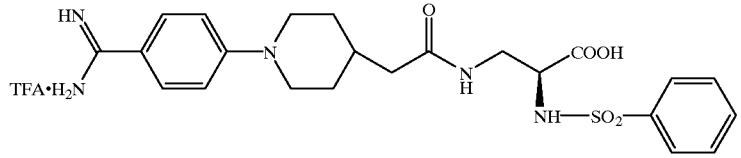

Example 70

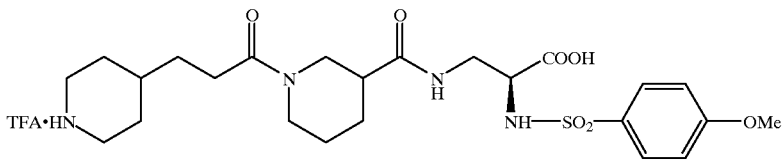

Platelet Aggregation Inhibitory Activity

The compounds of Examples 18 to 70 were tested in the same manner as in Example 17. The test results of the test compounds are shown in Table 2.

TABLE 2

Test results

| Test Compound | $IC_{50}$ (nM) |
| --- | --- |
| The compound of Example 18 | 33 |
| The compound of Example 19 | 30 |
| The compound of Example 20 | 57 |
| The compound of Example 21 | 15 |
| The compound of Example 24 | 30 |
| The compound of Example 25 | 22 |
| The compound of Example 26 | 29 |
| The compound of Example 27 | 26 |
| The compound of Example 28 | 58 |
| The compound of Example 29 | 170 |
| The compound of Example 30 | 16 |
| The compound of Example 31 | 142 |
| The compound of Example 32 | 151 |
| The compound of Example 33 | 15 |
| The compound of Example 34 | 126 |
| The compound of Example 35 | 25 |
| The compound of Example 36 | 62 |
| The compound of Example 37 | 48 |
| The compound of Example 38 | 35 |
| The compound of Example 39 | 185 |
| The compound of Example 40 | 3 |
| The compound of Example 41 | 35 |
| The compound of Example 42 | 233 |
| The compound of Example 43 | 260 |
| The compound of Example 44 | 263 |
| The compound of Example 45 | 121 |
| The compound of Example 46 | 32 |
| The compound of Example 47 | 238 |
| The compound of Example 48 | 67 |
| The compound of Example 49 | 170 |
| The compound of Example 50 | 203 |
| The compound of Example 53 | 111 |
| The compound of Example 54 | 79 |
| The compound of Example 55 | 300 |
| The compound of Example 56 | 90 |
| The compound of Example 57 | 18 |
| The compound of Example 58 | 96 |
| The compound of Example 59 | 34 |
| The compound of Example 60 | 31 |
| The compound of Example 61 | 24 |
| The compound of Example 62 | 26 |
| The compound of Example 63 | 15 |
| The compound of Example 64 | 32 |
| The compound of Example 65 | 79 |
| The compound of Example 66 | 16 |
| The compound of Example 67 | 32 |
| The compound of Example 68 | 43 |
| The compound of Example 69 | 29 |
| The compound of Example 70 | 57 |

Example 72

Synthesis of (2S)-2-(5-methoxy-1-naphthalene) sulfonylamino-3-(3-(3-(4-piperidyl)propanoylamino) propanoylamino)propanoic Acid TFA Salt The title compound is prepared in the same manner as in Example 2.

Yield: 162 mg. MS (SIMS): 535 [M+1]$^+$. HPLC retention time: 24.9 min. (under the same conditions as Example 1). $^1$H-NMR (DMSO-d$_6$) δ (ppm): 1.12–1.32 (2H, m), 1.37–1.52 (3H, m), 1.70–1.82 (2H, m), 1.90–2.10 (4H, m), 2.72–2.90 (2H, m), 3.00–3.30 (4H, m), 3.75–3.90 (1H, m), 4.05 (3H, s), 7.06 (1H, d, J=8 Hz), 7.59–7.76 (3H, m), 7.86 (1H, t, J=8 Hz), 8.07 (1H, d, J=8 Hz), 8.15–8.31 (3H, m), 8.46–8.62 (2H, m).

Example 73

Synthesis of (2R)-3-(3-(4-amidinobenzoylamino) propanoylamino)-2-benzenesulfonylaminopropanoic Acid TFA Salt The title compound is prepared in the same manner as in Example 1.

Yield: 99 mg. MS (SIMS): 462 [M+1]$^+$. HPLC retention time: 14.6 min. (under the same conditions as Example 1). $^1$H-NMR (DMSO-d$_6$) δ (ppm): 2.20–2.36 (2H, m), 3.05–3.55 (4H, m), 3.85–3.96 (1H, m), 7.50–7.76 (3H, m), 7.77 (2H, d, J=6 Hz), 7.88 (2H, d, J=8 Hz), 7.96–8.09 (4H, m), 8.15 (1H, d, J=9 Hz), 8.70 (1H, t, J=6 Hz), 9.23 (2H, s), 9.40 (2H, s).

The chemical structures of the compounds obtained in Examples 72 and 73 are as follows.

Example 72

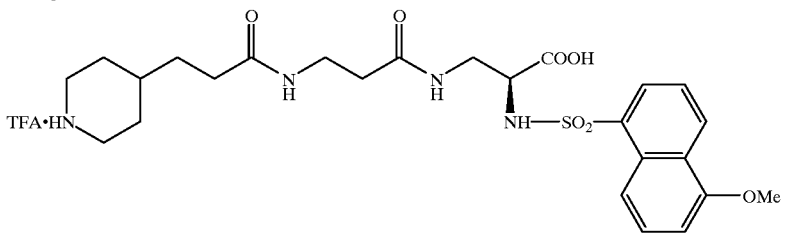

Example 73

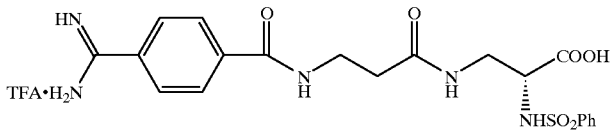

Example 74

Synthesis of (2S)-3-(3-(4-amidinobenzoylamino)propanoylamino)-2-(2-methyl)benzenesulfonylaminopropanoic Acid TFA Salt The title compound is prepared in the same manner as in Example 19.

Yield: 73 mg. MS (SIMS): 476 [M+1]+. HPLC retention time: 18.7 min. (under the same conditions as Example 1). $^1$H-NMR (DMSO-$d_6$) δ (ppm): 2.20–2.40 (2H, m), 2.58 (3H, s), 3.08–3.40 (4H, m), 3.78–3.90 (1H, m), 7.30–7.55 (3H, m), 7.79 (1H, d, J=8 Hz), 7.85–8.09 (5H, m), 8.15 (1H, d, J=8 Hz), 8.70 (1H, m), 9.25 (2H, s), 9.40 (2H, s).

Example 75

Synthesis of (2S)-3-(3-(4-amidinobenzoylamino)propanoylamino)-2-(3-methyl)benzenesulfonylaminopropanoic Acid TFA Salt The title compound is prepared in the same manner as in Example 19.

Yield: 90 mg. MS (SIMS): 476 [M+1]+. HPLC retention time: 19.5 min. (under the same conditions as Example 1). $^1$H-NMR (DMSO-$d_6$) δ (ppm): 2.20–2.35 (2H, m), 2.36 (3H, s), 3.05–3.45 (4H, m), 3.85–3.95 (1H, m), 7.37–7.62 (4H, m), 7.81–8.14 (6H, m), 8.70 (1H, m), 9.28 (2H, m), 9.40 (2H, s).

Example 76

Synthesis of (2S)-3-(3-(4-amidinobenzoylamino)propanoylamino)-2-(4-methyl)benzenesulfonylaminopropanoic Acid TFA Salt The title compound is prepared in the same manner as in Example 19.

Yield: 186 mg. MS (SIMS): 476 [M+1]+. HPLC retention time: 19.5 min. (under the same conditions as Example 1). $^1$H-NMR (DMSO-$d_6$) δ (ppm): 2.23–2.35 (2H, m), 2.36 (3H, s), 3.05–3.50 (4H, m), 3.83–3.94 (1H, m), 7.36 (2H, d, J=8 Hz), 7.65 (2H, d, J=8 Hz), 7.84–8.10 (6H, m), 8.66–8.75 (1H, m), 9.29 (2H, s), 9.40 (2H, s).

Example 77

Synthesis of (2S)-3-(3-(4-amidinobenzoylamino)propanoylamino)-2-(2-nitro)benzenesulfonylaminopropanoic Acid TFA Salt To a solution of (2S)-2-(2-nitro)benzenesulfonylamino-3-(3-(t-butoxycarbonylamino)propanoylamino)propanoic acid ethyl ester (0.701 g), which is prepared in the same manner as in Example 1-(4) and -(5), in acetonitrile (2 ml) is added dropwise a solution of methanesulfonic acid (0.690 g) in acetonitrile at a temperature below 20° C., and the mixture is stirred at room temperature for 30 minutes. To the mixture are added successively DMF (10 ml) and triethylamine (741 mg) at a temperature below 20° C. To the mixture are added N-t-butoxycarbonyl-4-amidinobenzoic acid (0.417 g), which is prepared in Example 1-(7), and HOBT.H$_2$O (0.213 g), and further thereto is added WSC.HCl (0.303 g) at 5–10° C., and the mixture is stirred for 30 minutes. The mixture is further stirred at room temperature for 12 hours, and the reaction mixture is concentrated under reduce pressure. To the residue is added TFA (10 ml) under ice-cooling, and the mixture is stirred at room temperature for one hour. The mixture is evaporated under reduced pressure to remove the TFA, and thereto is added ether, and the supernatant is removed. To the residue are added acetic acid (20 ml) and 1N hydrochloric acid (20 ml), and the mixture is heated with stirring at 50–60° C. for 13 hours. The reaction mixture is concentrated under reduced pressure, and the residue is purified by HPLC to give a white powder (357 mg).

MS (SIMS): 507 [M+1]+. HPLC retention time: 18.3 min. (under the same conditions as Example 1). $^1$H-NMR (DMSO-$d_6$) δ (ppm): 2.28–2.42 (2H, m), 3.15–3.40 (4H, m), 4.03–4.16 (1H, m), 7.80–8.07 (8H, m), 8.09–8.17 (1H, m), 8.41 (1H, d, J=8 Hz), 8.71 (1H, t, J=5 Hz), 9.28 (2H, s), 9.40 (2H, s).

Example 78

Synthesis of (2S)-3-(3-(4-amidinobenzoylamino)propanoylamino)-2-(4-fluoro)benzenesulfonylaminopropanoic Acid TFA Salt The title compound is prepared in the same manner as in Example 19.

Yield: 137 mg. MS (SIMS): 480 [M+1]+. HPLC retention time: 17.3 min. (under the same conditions as Example 1). $^1$H-NMR (DMSO-$d_6$) δ (ppm): 2.31 (2H, t, J=8 Hz), 3.05–3.45 (4H, m), 3.85–3.97 (1H, m), 7.40 (2H, dd, J=8.5, 9 Hz), 7.82 (2H, dd, J=8.5, 9 Hz), 7.88 (2H, d, J=8.5 Hz), 8.01 (2H, d, J=8.5 Hz), 8.06 (1H, m), 8.22 (1H, d, J=9 Hz), 8.71 (1H, t, J=5 Hz), 9.23 (2H, s), 9.40 (2H, s).

Example 79

Synthesis of (2S)-3-(3-(4-amidinobenzoylamino)propanoylamino)-2-(4-ethyl)benzenesulfonylaminopropanoic Acid Ethyl Ester The title compound is prepared in the same manner as in Example 22.

Yield: 120 mg. MS (SIMS): 518 [M+1]$^+$. HPLC retention time: 29.1 min. (under the same conditions as Example 1). $^1$H-NMR (DMSO-d$_6$) δ (ppm): 0.97 (3H, t, J=7 Hz), 1.17 (3H, t, J=7 Hz), 2.31 (2H, t, J=7 Hz), 2.66 (2H, q, J=7 Hz), 3.10–3.49 (4H, m), 3.76 (2H, q, J=7 Hz), 3.89–4.00 (1H, m), 7.40 (2H, d, J=9 Hz), 7.66 (2H, d, J=9 Hz), 7.88 (2H, d, J=9 Hz), 8.06 (2H, d, J=9 Hz), 8.09 (1H, t, J=6 Hz), 8.26 (1H, d, J=9 Hz), 8.72 (1H, t, J=5.5 Hz), 9.29 (2H, s), 9.40 (2H, s).

Example 80

Synthesis of (2S)-3-(3-(4-amidinobenzoylamino)propanoylamino)-2-(4-ethyl)benzenesulfonylaminopropanoic Acid TFA Salt To the compound (120 mg) obtained in Example 79 are added 1N hydrochloric acid (5 ml) and acetic acid (5 ml), and the mixture is heated with stirring at 60° C. for 18 hours. The reaction mixture is concentrated under reduced pressure, and purified by HPLC to give the title compound (90.4 mg) as a white powder.

MS (SIMS): 490 [M+1]$^+$. HPLC retention time: 23.5 min. (under the same conditions as Example 1). $^1$H-NMR (DMSO-d$_6$) δ (ppm): 1.17 (3H, t, J=8 Hz), 2.23–2.36 (2H, m), 2.66 (2H, q, J=8 Hz), 3.08–3.50 (4H, m), 3.78 (1H, m), 7.38 (2H, d, J=8 Hz), 7.68 (2H, d, J=8 Hz), 7.87 (2H, d, J=8 Hz), 7.80–7.90 (1H, m), 7.94–8.05 (1H, m), 8.02 (2H, d, J=8 Hz), 8.72 (1H, t, J=5 Hz), 9.36 (2H, s), 9.42 (2H, s).

Example 81

Synthesis of (2S)-3-(3-(4-amidinobenzoylamino)propanoylamino)-2-(2-amino)benzenesulfonylaminopropanoic Acid TFA Salt To a solution of the compound (85 mg) obtained in Example 77 in ethanol (5 ml) is added 10% palladium-carbon (50% wet, 100 mg), and the mixture is stirred at room temperature for 3 hours under hydrogen atmosphere. The insoluble materials are removed by filtration and the filtrate is concentrated under reduced pressure. The residue is purified by HPLC to give the title compound (58 mg).

MS (SIMS): 477 [M+1]$^+$. HPLC retention time: 15.1 min. (under the same conditions as Example 1). $^1$H-NMR (DMSO-d$_6$) δ (ppm): 2.28–2.37 (2H, m), 3.06–3.19 (2H, m), 3.6–3.49 (4H, m), 3.72–3.85 (1H, m), 6.57 (1H, t, J=7 Hz), 6.78 (1H, d, J=7 Hz), 7.23 (1H, t, J=7 Hz), 7.45 (1H, d, J=7 Hz), 7.84–8.05 (6H, m), 8.70 (1H, t, J×5.5 Hz) 9.18 (2H, s), 9.40 (2H, s).

The chemical structures of the compounds obtained in Examples 74 to 81 are as follows.

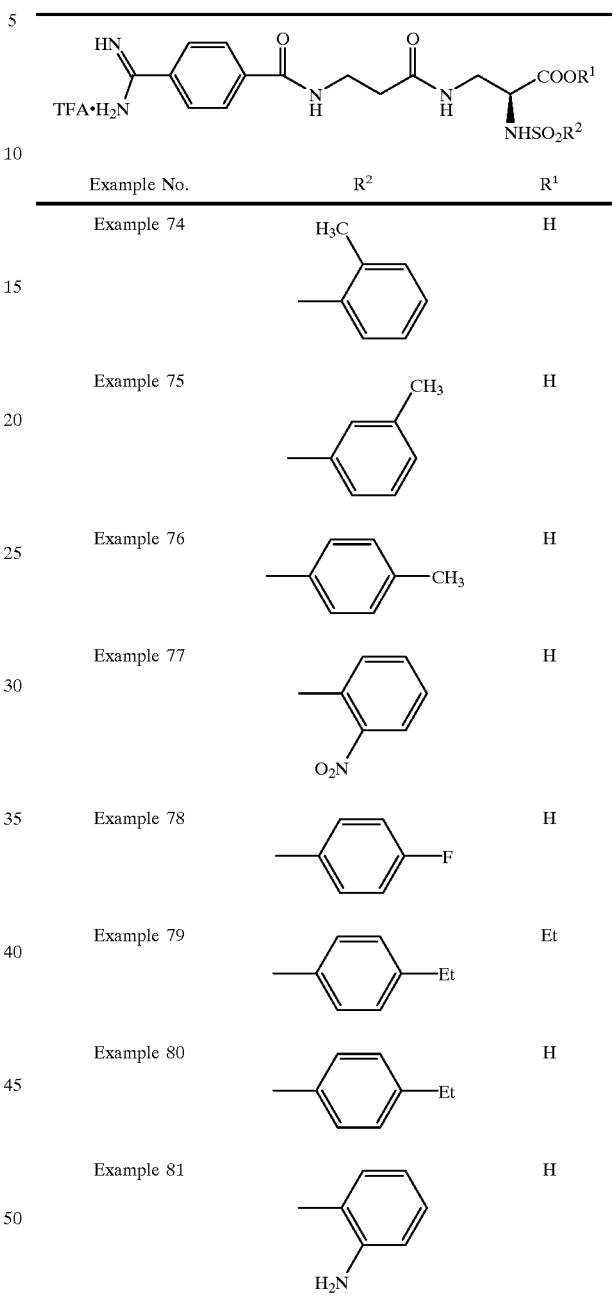

Example 82

Synthesis of (2S)-3-(4-(4-amidinophenoxy)butanoylamino)-2-(2-trifluoromethyl)benzenesulfonylaminopropanoic Acid TFA Salt The title compound is prepared in the same manner as in Example 57.

Yield: 295 mg. MS (SIMS): 517 [M+1]$^+$. HPLC retention time: 26.2 min. (under the same conditions as Example 1). $^1$H-NMR (DMSO-d$_6$) δ (ppm): 1.80–2.00 (2H, m), 2.15–2.25 (2H, m), 3.25–3.50 (2H, m), 3.95–4.15 (3H, m), 7.14 (2H, d, J=8.9 Hz), 7.70–8.00 (5H, m), 8.00–8.20 (2H, m), 8.21 (1H, d, J=9.2 Hz), 8.87 (2H, bs), 9.13 (2H, bs).

Example 83

Synthesis of (2S)-3-(4-(4-amidinophenoxy) butanoylamino)-2-(4-ethyl) benzenesulfonylaminopropanoic Acid TFA Salt The title compound is prepared in the same manner as in Example 57.

Yield: 241 mg. MS (SIMS): 477 [M+1]$^+$. HPLC retention time: 27.1 min. (under the same conditions as Example 1). $^1$H-NMR (DMSO-d$_6$) δ (ppm): 1.17 (3H, t, J=8 Hz), 1.80–2.00 (2H, m), 2.05–2.25 (2H, m), 2.65 (2H, q, J=8 Hz), 3.00–3.20 (1H, m), 3.25–3.45 (1H, m), 3.80–3.95 (1H, m), 4.05 (2H, t, J=6.0 Hz), 7.14 (2H, d, J=8.9 Hz), 7.38 (2H, d, J=8.6 Hz), 7.67 (2H, d, J=8.6 Hz), 7.81 (2H, d, J=8.9 Hz), 7.99 (1H, t, J=6 Hz), 8.06 (1H, d, J=8.9 Hz), 9.02 (2H, bs), 9.14 (2H, bs).

Example 84

Synthesis of (2S)-3-(4-(4-amidinophenoxy) butanoylamino)-2-(2-amino) benzenesulfonylaminopropanoic Acid TFA Salt To a solution of the compound (100 mg) obtained in Example 59 in ethanol (10 ml) is added 10% palladium-carbon (50% wet, 150 mg), and the mixture is subjected to hydrogenation at room temperature for 3.5 hours. The catalyst is removed by filtration, and the filtrate is concentrated under reduced pressure. The residue is purified by HPLC to give the title compound (50 mg) as a white powder.

MS (SIMS): 464 [M+1]$^+$. HPLC retention time: 19.8 min. (under the same conditions as Example 1). $^1$H-NMR (DMSO-d$_6$) δ (ppm): 1.80–2.00 (2H, m), 2.05–2.25 (2H, m), 3.00–3.50 (2H, m), 3.70–3.85 (1H, m), 4.05 (2H, bt, J=6 Hz), 6.50–6.60 (1H, m), 6.77 (1H, dd, J=0.7, 8.2 Hz), 7.14 (2H, d, J=8.9 Hz), 7.22 (1H, ddd, J=1.7, 7.3, 8.6 Hz), 7.44 (1H, dd, J=1.3, 7.9 Hz), 7.80 (2H, d, J=8.9 Hz), 7.90 (1H, bt, J=5.9 Hz), 7.95 (1H, d, J=8.9 Hz), 8.87 (2H, bs), 9.12 (2H, bs).

Example 85

Synthesis of (2S)-3-(5-(4-amidinophenoxy) pentanoylamino)-2-(2-nitro) benzenesulfonylaminopropanoic Acid TFA Salt The title compound is prepared in the same manner as in Example 63.

Yield: 69 mg MS (SIMS): 508 [M+1]$^+$. HPLC retention time: 25.5 min. (under the same conditions as Example 1). $^1$H-NMR (DMSO-d$_6$) δ (ppm): 1.50–1.80 (4H, m), 2.00–2.20 (2H, m), 3.15–3.55 (2H, m), 4.00–4.15 (3H, m), 7.15 (2H, d, J=8.9 Hz), 7.75–8.10 (7H, m), 8.39 (1H, d, J=8.9 Hz), 8.88 (2H, bs), 9.12 (2H, bs).

Example 86

Synthesis of (2S)-3-(5-(4-amidinophenoxy) pentanoylamino)-2-(2,4,6-trimethyl) benzenesulfonylaminopropanoic Acid TFA Salt The title compound is prepared in the same manner as in Example 63.

Yield: 191 mg. MS (SIMS): 505 [M+1]$^+$. HPLC retention time: 30.6 min. (under the same conditions as Example 1). $^1$H-NMR (DMSO-d$_6$) δ (ppm): 1.45–1.80 (4H, m), 1.90–2.10 (2H, m), 2.23 (3H, s), 2.49 (3H, s), 2.51 (3H, s), 3.00–3.40 (2H, m), 3.70–3.90 (1H, m), 4.00–4.15 (2H, m), 6.98 (2H, s), 7.14 (2H, d, J=8.9 Hz), 7.80 (2H, d, J=8.9 Hz), 7.85–8.00 (2H, m), 8.85 (2H, bs), 9.12 (2H, bs).

The chemical structures of the compounds obtained in Examples 82 to 86 are as follows.

| Example No. | R$^2$ |
|---|---|
| | 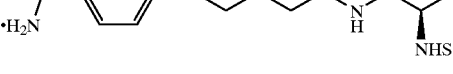 |
| Example 82 | 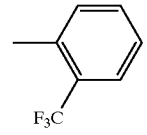 |
| Example 83 | 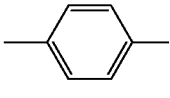 |
| Example 84 | 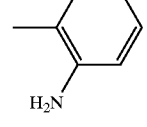 |
| | 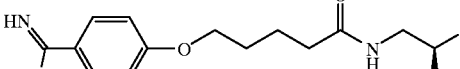 |
| Example 85 | 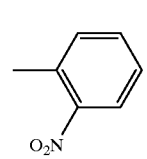 |
| Example 86 | 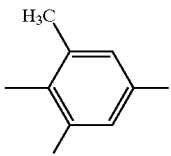 |

Example 87

Synthesis of (2S)-3-(5-(4-amidinophenyl) pentanoylamino)-2-(2,4,6-trimethyl) benzenesulfonylaminopropanoic Acid TFA Salt The title compound is prepared in the same manner as in Example 66.

Yield: 225 mg. MS (SIMS): 489 [M+1]$^+$. HPLC retention time: 30.7 min. (under the same conditions as Example 1). $^1$H-NMR (DMSO-d$_6$) δ (ppm): 1.35–1.65 (4H, m), 1.90–2.10 (2H, m), 2.23 (3H, s), 2.50 (3H, s), 2.53 (3H, s), 2.66 (2H, t, J=7 Hz), 3.00–3.20 (1H, m), 3.20–3.50 (1H, m), 3.70–3.90 (1H, m), 6.98 (2H, s), 7.44 (2H, d, J=8 Hz), 7.73 (2H, d, J=8 Hz), 7.80–8.00 (2H, m), 9.03 (2H, bs), 9.22 (2H, bs).

Example 88

Synthesis of (2S)-3-(5-(4-amidinophenyl)pentanoylamino)-2-(1-naphthalene)sulfonylaminopropanoic Acid TFA Salt The title compound is prepared in the same manner as in Example 66.

Yield: 211 mg. MS (SIMS): 497 [M+1]$^+$. HPLC retention time: 29.2 min. (under the same conditions as Example 1). $^1$H-NMR (DMSO-d$_6$) δ (ppm): 1.20–1.55 (4H, m), 1.65–1.95 (2H, m), 2.62 (2H, t, J=7.3 Hz), 2.95–3.15 (1H, m), 3.20–3.40 (1H, m), 3.75–3.95 (1H, m), 7.42 (2H, d, J=8.3 Hz), 7.55–7.80 (4H, m), 7.73 (2H, d, J=8.3 Hz), 8.00–8.30 (3H, m), 8.47 (1H, d, J=8.9 Hz), 8.63 (1H, d, J=7.9 Hz), 9.01 (2H, bs), 9.23 (2H, bs).

Example 89

Synthesis of (2S)-3-(5-(4-amidinophenyl)pentanoylamino)-2-(4-ethyl)benzenesulfonylaminopropanoic Acid TFA Salt The title compound is prepared in the same manner as in Example 66.

Yield: 167 mg. MS (SIMS): 475 [M+1]$^+$. HPLC retention time: 29.4 min. (under the same conditions as Example 1). $^1$H-NMR (DMSO-d$_6$) δ (ppm): 1.18 (3H, t, J=7.6 Hz), 1.30–1.65 (4H, m), 1.85–2.10 (2H, m), 2.55–2.75 (4H, m), 2.90–3.20 (1H, m), 3.20–3.40 (1H, m), 3.70–3.90 (1H, m), 7.37 (2H, d, J=8.3 Hz), 7.44 (2H, d, J=8.3 Hz), 7.67 (2H, d, J=8.3 Hz), 7.73 (2H, d, J=8.3 Hz), 7.80–7.90 (1H, m), 8.02 (1H, d, J=8.6 Hz), 9.04 (2H, bs), 9.23 (2H, bs).

Example 90

Synthesis of (2S)-3-(5-(4-amidinophenyl)pentanoylamino)-2-(2-trifluoromethyl)benzenesulfonylaminopropanoic Acid TFA Salt The title compound is prepared in the same manner as in Example 66.

Yield: 127 mg. MS (SIMS): 515 [M+1]$^+$. HPLC retention time: 28.5 min. (under the same conditions as Example 1). $^1$H-NMR (DMSO-d$_6$) δ (ppm): 1.35–1.70 (2H, m), 1.95–2.15 (2H, m), 2.66 (2H, t, J=7 Hz), 3.15–3.50 (2H, m), 3.90–4.10 (1H, m), 7.44 (2H, d, J=8.3 Hz), 7.72 (2H, d, J=8.3 Hz), 7.80–8.20 (6H, m), 8.88 (2H, bs), 9.22 (2H, bs).

Example 91

Synthesis of (2S)-3-(6-(4-amidinophenyl)hexanoylamino)-2-benzenesulfonylaminopropanoic Acid TFA Salt The title compound is prepared by using 6-(p-amidinophenyl)hexanoic acid (J. Med. Chem., 36, 1811 (1993)) in the same manner as in Example 66.

Yield: 197 mg. MS (SIMS): 461 [M+1]$^+$. HPLC retention time: 25.2 min. (under the same conditions as Example 1). $^1$H-NMR (DMSO-d$_6$) δ (ppm): 1.10–1.30 (2H, m), 1.35–1.70 (4H, m), 1.94 (2H, bt, J=7 Hz), 2.66 (2H, t, J=8 Hz), 3.00–3.15 (1H, m), 3.20–3.40 (1H, m), 3.80–3.95 (1H, m), 7.35–7.80 (9H, m), 7.87 (1H, bt, J=5 Hz), 8.14 (1H, d, J=8.9 Hz), 9.01 (2H, bs), 9.23 (2H, bs).

Example 92

Synthesis of (2S)-3-(6-(4-amidinophenyl)hexanoylamino)-2-(2,4,6-trimethyl)benzenesulfonylaminopropanoic Acid TFA Salt The title compound is prepared in the same manner as in Example 91.

Yield: 168 mg MS (SIMS): 503 [M+1]+. HPLC retention time: 32.2 min. (under the same conditions as Example 1). $^1$H-NMR (DMSO-d$_6$) δ (ppm): 1.10–1.30 (2H, m), 1.30–1.70 (4H, m), 1.80–2.00 (2H, m), 2.22 (3H, s), 2.50 (3H, s), 2.53 (3H, s), 2.66 (2H, t, J=7.6 Hz), 3.00–3.20 (1H, m), 3.20–3.40 (1H, m), 3.70–3.90 (1H, m), 6.98 (2H, s), 7.44 (2H, d, J=8 Hz), 7.73 (2H, d, J=8 Hz), 7.84 (1H, bs), 7.93 (1H, d, J=8.9 Hz), 9.08 (2H, bs), 9.23 (2H, bs).

The chemical structures of the compounds obtained in Examples 87 to 92 are as follows.

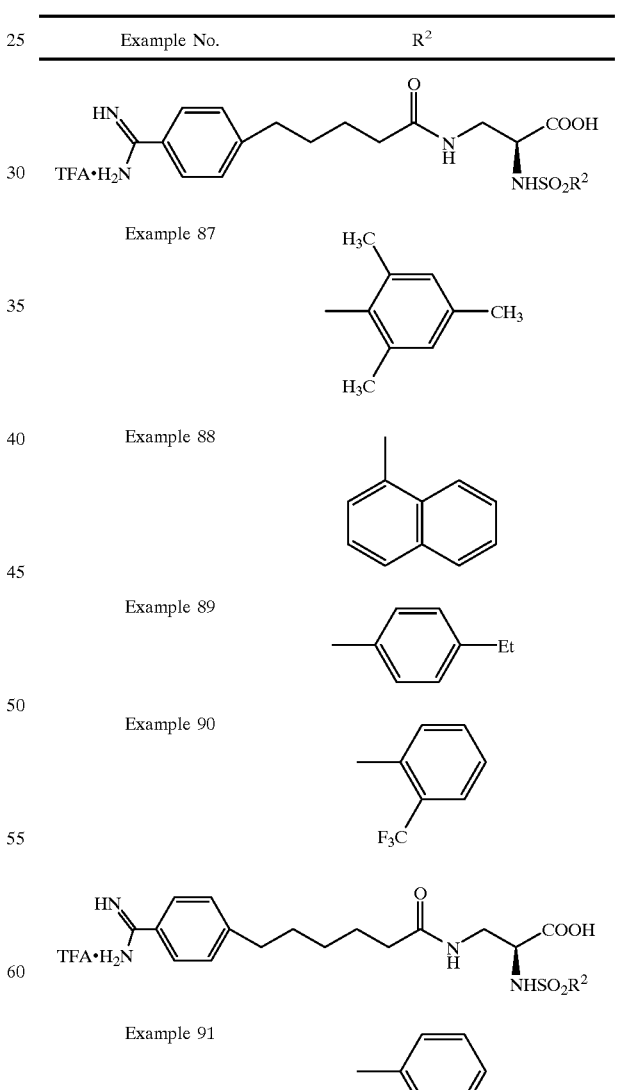

| Example No. | R² |
|---|---|
| Example 92 | 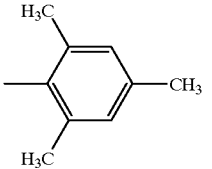 |

Example 93

Synthesis of (2S)-3-(2-(1-(4-amidinophenyl)-4-piperidyl)ethanoylamino)-2-(4-methoxy)benzenesulfonylaminopropanoic Acid TFA Salt The title compound is prepared in the same manner as in Example 69.

Yield: 160 mg. MS (SIMS): 518 [M+1]⁺. HPLC retention time: 24.3 min. (under the same conditions as Example 1). ¹H-NMR (DMSO-d₆) δ (ppm): 1.05–1.22 (2H, m), 1.61–1.74 (2H, m), 1.80–2.00 (3H, m), 2.80–2.95 (2H, m), 3.05–3.18 (2H, m), 3.24–3.36 (2H, m), 3.85–4.00 (1H, m), 3.81 (3H, s), 6.99–7.14 (4H, m), 7.68–7.75 (4H, m), 7.94 (2H, d, J=9 Hz), 8.53 (2H, s), 8.88 (2H, s).

Example 94

Synthesis of (2S)-3-(5-(4-amidinobenzoyl)pentanoylamino)-2-benzenesulfonylaminopropanoic Acid TFA Salt (1) 6-(p-Cyanophenyl)hexanoic Acid Methyl Ester To a solution of 6-(p-cyanophenyl)hexanoic acid (1.0 g), which is disclosed in J. Med. Chem., 36, 1811 (1993), in methylene chloride (10 ml) are added methanol (0.2 ml), WSC.HCl (883 mg) and 4-dimethylaminopyridine (561 mg), and the mixture is stirred at room temperature for 30 minutes. The mixture is diluted with ethyl acetate, and washed with 1N hydrochloric acid and a saturated aqueous sodium hydrogen carbonate solution, and purified by silica gel column chromatography (n-hexane/ethyl acetate=5:1) to give the title compound (600 mg).

Yield: 56%. ¹H-NMR (CDCl₃) δ (ppm): 1.25–1.45 (2H, m), 1.55–1.75 (4H, m), 2.31 (2H, t, J=7 Hz), 2.67 (2H, t, J=8 Hz), 3.66 (3H, s), 7.27 (2H, d, J=8.6 Hz), 7.57 (2H, d, J=8.6 Hz).

(2) 5-(4-Cyanobenzoyl)pentanoic Acid Methyl Ester

The compound (620 mg) obtained in the above (1) is dissolved in a mixture of acetic acid (30 ml) and water (5 ml), and thereto is added chromic anhydride (1.3 g)/acetic acid (2 ml), and the mixture is stirred at room temperature for 17.5 hours. The mixture is diluted with ethyl acetate, and washed with a saturated aqueous sodium hydrogen carbonate solution, and purified by silica gel column chromatography (n-hexane/ethyl acetate=5:1→2:1) to give the title compound (70 mg, 11%), and the starting compound (365 mg, 59%) is also recovered.

¹H-NMR (CDCl₃) δ (ppm): 1.60–1.90 (4H, m), 2.39 (2H, t, J=7 Hz), 3.02 (2H, t, J=6.9 Hz), 3.68 (3H, s), 7.78 (2H, d, J=8.6 Hz), 8.05 (2H, d, J=8.6 Hz).

(3) (2S)-2-Benzenesulfonylamino-3-(5-(4-cyanobenzoyl)pentanoylamino)propanoic Acid Ethyl Ester The compound (70 mg) obtained in the above (2) is dissolved in a mixture of methanol (1.5 ml) and THF (1.5 ml), and thereto is added a solution of lithium hydroxide (34 mg) in water (1.5 ml), and the mixture is stirred at room temperature for one hour. The mixture is concentrated under reduced pressure, and the pH value of the residue is adjusted to pH 2 with 1N hydrochloric acid, and extracted with ethyl acetate. The extract is evaporated to remove the solvent to give a carboxylic acid compound (58 mg, 87%). The carboxylic acid compound and the compound obtained in Example 54-(4), (2S)-2-benzenesulfonylamino-3-t-butoxycarbonylaminopropanoic acid ethyl ester (130 mg) are treated in the same manner as in Example 66-(2) to give the title compound (93 mg, 73%).

¹H-NMR (CDCl₃) δ (ppm): 1.11 (3H, t, J=7.3 Hz), 1.60–1.90 (4H, m), 2.25 (2H, t, J=7 Hz), 3.02 (2H, t, J=7 Hz), 3.50–3.75 (2H, m), 3.90–4.05 (3H, m), 6.11 (1H, bs), 6.47 (1H, m), 7.40–7.65 (3H, m), 7.70–7.90 (4H, m), 8.05 (2H, d, J=8.6 Hz).

(4) (2S)-3-(5-(4-Amidinobenzoyl)pentanoylamino)-2-benzenesulfonylaminopropanoic Acid TFA Salt The compound obtained in the above (3) is treated in the same manner in Example 66-(3), -(4) to give the title compound.

Yield: 16 mg. MS (SIMS): 475 [M+1]⁺. HPLC retention time: 21.1 min. (under the same conditions as Example 1). ¹H-NMR (DMSO-d₆) δ (ppm): 1.35–1.70 (4H, m), 1.90–2.15 (2H, m), 3.00–3.40 (4H, m), 3.70–4.00 (1H, m), 7.50–7.65 (3H, m), 7.70–8.00 (5H, m), 8.05–8.25 (3H, m), 9.26 (2H, bs), 9.44 (2H, bs).

Example 95

Synthesis of (2S)-3-((1-(4-amidinobenzoyl)-3-piperidyl)carbonylamino)-2-benzenesulfonylaminopropanoic Acid TFA Salt (1) (2S)-3-(1-t-Butoxycarbonyl-3-piperidyl)carbonylamino-2-benzenesulfonylaminopropanoic Acid Ethyl Ester To a solution of the compound (252 mg) obtained in Example 54-(4) in acetonitrile (1.5 ml) is added dropwise a solution of methanesulfonic acid (325 mg) in acetonitrile (1.5 ml), and the mixture is stirred at 20° C. for 30 minutes. To the mixture are added dropwise DMF (5 ml) and triethylamine (343 mg) at 5–10° C., and further thereto are added the compound (162 mg) obtained in Example 70-(1), HOBT.H₂O (124 mg) and then further WSC.HCl (156 mg). The mixture is stirred at 5–10° C. for 30 minutes, and further stirred at room temperature for four hours. The reaction mixture is poured into water, and extracted three times with ethyl acetate. The combined ethyl acetate layers are washed successively with 1N hydrochloric acid, a saturated aqueous sodium hydrogen carbonate solution and a saturated brine (each twice), and dried over magnesium sulfate. The desiccant is removed by filtration, and the filtrate is concentrated under reduced pressure to give the title compound (373 mg) as an oily product.

(2) (2S)-3-((1-(4-Cyanobenzoyl)-3-piperidyl)carbonylamino)-2-benzenesulfonylaminopropanoic Acid To a solution of the compound (373 mg) obtained in above (1) in acetonitrile (1.5 ml) is added dropwise a solution of methanesulfonic acid (380 mg) in acetonitrile (1.5 ml), and the mixture is stirred at room temperature for 30 minutes. To the mixture are added dropwise DMF (4 ml) and triethylamine (400 mg) at 5–10° C. under ice-cooling, and further thereto are added 4-cyanobenzoic acid (129 mg), HOBT.H₂O (146 mg) and then further WSC.HCl (183 mg). The mixture is stirred at 5–10° C. for 30 minutes, and further stirred at room temperature for 12 hours. The reaction mixture is poured into water, and extracted with ethyl acetate. The combined organic layers are washed successively with 1N hydrochloric acid, a saturated aqueous sodium hydrogen carbonate solution and a saturated brine (each twice), and dried over magnesium sulfate. The desiccant is removed by filtration, and the filtrate is concentrated under reduced pressure to give the title compound (390 mg) as a white powder.

(3) (2S)-3-((1-(4-amidinobenzoyl)-3-piperidyl)carbonylamino)-2-benzenesulfonylaminopropanoic Acid TFA Salt To a solution of the compound (390 mg) obtained in the above (2) in a mixture of pyridine (10 ml) and triethylamine (2 ml) is brown hydrogen sulfide gas for one hour, and the mixture is allowed to stand at room temperature for 20 hours. The hydrogen sulfide gas is removed by using nitrogen gas, and the reaction mixture is concentrated to dryness under reduced pressure. To the residue are added acetone (10 ml) and methyl iodide (0.25 ml), and the mixture is heated with stirring at 50–60° C. for 1.5 hour, and the mixture is concentrated to dryness under reduced pressure. To the resulting residue are added methanol (10 ml) and ammonium acetate (121 mg), and the mixture is heated with stirring at 70–80° C. for two hours, and then the reaction mixture is concentrated to dryness under reduced pressure. To the residue are added 1N hydrochloric acid (15 ml) and acetic acid (15 ml), and the mixture is heated with stirring at 60° C. for 30 hours. The mixture is concentrated under reduced pressure, and purified by HPLC to give the title compound (118 mg) as a white powder.

MS (SIMS): 502 [M+1]$^+$. HPLC retention time: 20.4 min., 21.7 min. (a diastereomer mixture) (under the same conditions as Example 1). $^1$H-NMR (DMSO-d$_6$) δ (ppm): 1.30–1.95 (4H, m), 2.15–2.38 (1H, m), 2.75–3.60 (5H, m), 3.75–3.99 (1H, m), 4.25–4.50 (1H, m), 7.47–8.22 (11H, m), 9.25 (2H, s), 9.37 (2H, s).

Example 96

Synthesis of (2S)-3-(3-(4-amidinobenzoylmethylamino)propanoylamino)-2-benzensulfonylaminopropanoic Acid TFA Salt (1) (2S)-2-Benzenesulfonylamino-3-(3-(t-butoxycarbonylmethylamino)propanoylamino)propanoic Acid Ethyl Ester The compound (500 mg) obtained in Example 54-(3) and N-methyl-N-Boc-β-alanine (333 mg) are treated in the same manner as in Example 1-(4), -(5) to give the title compound (659 mg).

(2) (2S)-3-(3-(4-Amidinobenzoylmethylamino)propanoylamino)-2-benzenesulfonylaminopropanoic Acid TFA Salt The compound (659 mg) obtained in the above (1) is treated in the same manner as in Example 77 to give the title compound (187 mg) as a white powder.

MS (SIMS): 476 [M+1]$^+$. HPLC retention time: 15.3 min. (under the same conditions as Example 1). $^1$H-NMR (DMSO-d$_6$) δ (ppm): 2.20–2.43 (2H, m), 2.83, 2.93 (total 3H, each s), 3.02–3.67 (4H, m), 3.76–4.00 (1H, m), 7.50–7.95 (9H, m), 8.04–8.23 (2H, m), 9.20 (2H, s), 9.38 (2H, s).

Example 97

Synthesis of (2S)-3-(3-(4-amidinobenzoylmethylamino)propanoylamino)-2-(4-ethyl)benzenesulfonylaminopropanoic Acid TFA Salt The title compound is prepared in the same manner as in Example 96.

Yield: 141 mg. MS (SIMS): 504 [M+1]$^+$. HPLC retention time: 23.5 min. (under the same conditions as Example 1). $^1$H-NMR (DMSO-d$_6$) δ (ppm): 1.18 (3H, t, J=8 Hz), 2.20–2.46 (2H, m), 2.66 (2H, q, J=8 Hz), 2.83, 2.93 (total 3H, each s), 3.00–3.68 (4H, m), 3.75–3.95 (1H, m), 7.35–7.45 (2H, m), 7.55–7.72 (3H, m), 7.85 (2H, d, J=8 Hz), 8.00–8.17 (3H, m), 9.03–9.22 (2H, m), 9.37 (2H, s).

The chemical structures of the compounds obtained in Examples 93 to 97 are as follows.

Example 93

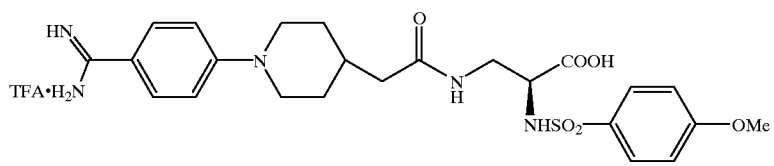

Example 94

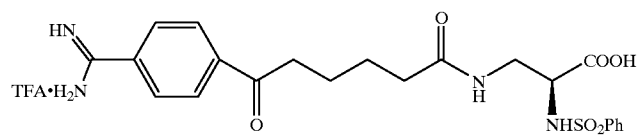

Example 95

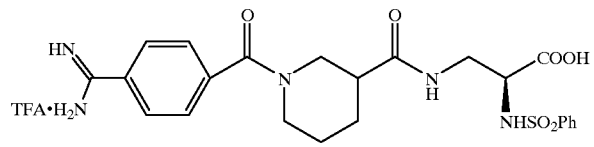

-continued

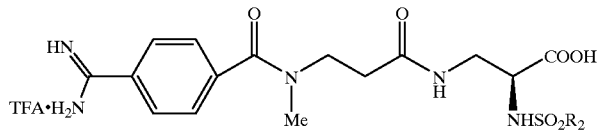

| Example No. | R² |
|---|---|
| Example 96 | phenyl |
| Example 97 | 4-ethylphenyl |

Example 98

Synthesis of (2S)-2-benzenesulfonylamino-3-(3-(4-(N-methylamidino)benzoylamino)propanoylamino) propanoic Acid TFA Salt (1) (2S)-2-Benzenesulfonylamino-3-(3-(4-cyanobenzoylamino)propanoylamino)propanoic Acid Ethyl Ester (2S)-2-Benzenesulfonylamino-3-(3-(t-butoxycarbonylamino)propanoylamino)propanoic acid ethyl ester, which is prepared in the same manner as in Example 1-(4), -(5) by using the compound obtained in Example 54-(3), and 4-cyanobenzoic acid are condensed in the same manner as in Example 1-(4) to give the title compound (735 mg) as a white powder.

(2) (2S)-2-Benzenesulfonylamino-3-(3-(4-(N-methylamidino)benzoylamino)propanoylamino)propanoic Acid TFA Salt The compound (208 mg) obtained in the above (1) is treated in the same manner as in Example 19-(2) by using methylamine acetate instead of ammonium acetate to give the title compound (29 mg).

MS (SIMS): 476 [M+1]⁺. HPLC retention time: 15.6 min. (under the same conditions as Example 1). $^1$H-NMR (DMSO-d$_6$) δ (ppm): 2.23–2.36 (2H, m), 3.01 (3H, d, J=5 Hz), 20 3.06–3.19 (1H, m), 3.24–3.50 (4H, m), 7.51–7.65 (3H, m), 7.73–7.87 (4H, m), 7.97–8.08 (3H, m), 8.15 (1H, d, J=9 Hz), 8.70 (1H, t, J=5 Hz), 9.04 (1H, s), 9.54 (1H, s), 10.30 (1H, s).

Example 99

Synthesis of (2S)-2-benzenesulfonylamino-3-(3-(4-(N-ethylamidino)benzoylamino)propanoylamino) propanoic Acid TFA Salt The title compound is prepared in the same manner as in Example 98 by using ethylamine acetate.

Yield: 33 mg. MS (SIMS): 490 [M+1]⁺. HPLC retention time: 16.9 min. (under the same conditions as Example 1). $^1$H-NMR (DMSO-d$_6$) δ (ppm): 1.25 (3H, t, J=7 Hz), 2.25–2.37 (2H, m), 3.05–3.45 (6H, m), 3.80–3.90 (1H, m), 7.51–7.67 (3H, m), 7.74–7.87 (5H, m), 7.95–8.10 (4H, m), 8.72 (1H, t, J=4 Hz), 9.05, 9.49, 9.81 (total 3H, each s).

Example 100

Synthesis of (2S)-2-benzenesulfonylamino-3-(3-(4-(N,N-dimethylamidino)benzoylamino) propanoylamino)propanoic Acid TFA Salt The title compound is prepared in the same manner as in Example 98 by using dimethylamine acetate.

Yield: 31 mg. MS (SIMS): 490 [M+1]⁺. HPLC retention time: 16.6 min. (under the same conditions as Example 1). $^1$H-NMR (DMSO-d$_6$) δ (ppm): 2.20–2.37 (2H, m), 2.95 (3H, s), 3.05–3.20 (2H, m), 3.22 (3H, s), 3.25–3.55 (2H, m), 3.85–3.98 (1H, m), 7.50–7.81 (7H, m), 7.95–8.19 (4H, m), 8.66 (1H, t, J=4 Hz), 8.99 (1H, s), 9.36 (1H, s).

Example 101

Synthesis of (2S)-2-benzenesulfonylamino-3-(3-(4-hydrazinoiminobenzoylamino)propanoylamino) propanoic Acid TFA Salt The title compound is prepared in the same manner as in Example 98 by using a solution of hydrazine acetate in methanol.

Yield: 17 mg. MS (SIMS): 477 [M+1]⁺. HPLC retention time: 14.4 min. (under the same conditions as Example 1). $^1$H-NMR (DMSO-d$_6$) δ (ppm): 2.21–2.37 (2H, m), 3.05–3.50 (4H, m), 3.84–3.95 (1H, m), 7.50–8.20 (12H, m), 8.55–8.79 (2H, m), 9.82 (1H, m).

Example 102

Synthesis of (2S)-2-benzenesulfonylamino-3-(3-(4-acetylhydrazinoiminobenzoylamino) propanoylamino)propanoic Acid TFA Salt The title compound is prepared in the same manner as in Example 98 by using a solution of hydrazine acetate in methanol.

Yield: 49 mg. MS (SIMS): 519 [M+1]⁺. HPLC retention time: 13.6 min. (under the same conditions as Example 1). $^1$H-NMR (DMSO-d$_6$) δ (ppm): 2.02 (3H, s), 2.22–2.38 (2H, m), 3.03–3.50 (4H, m), 3.84–3.98 (1H, m), 7.50–7.66 (3H, m), 7.74–7.94 (4H, m), 7.97–8.09 (3H, m), 8.15 (1H, d, J=9 Hz), 8.74 (2H, m), 9.83 (2H, s), 10.75 (1H, s).

Example 103

Synthesis of (2S)-2-benzenesulfonylamino-3-(3-(4-(N-n-butylamidino)benzoylamino)propanoylamino) propanoic Acid TFA Salt The title compound is prepared in the same manner as in Example 98 by using n-butylamine acetate.

Yield: 16 mg. MS (SIMS): 518 [M+1]⁺. HPLC retention time: 22.2 min. (under the same conditions as Example 1).

¹H-NMR (DMSO-d₆) δ (ppm): 0.93 (3H, t, J=7 Hz), 1.31–1.47 (2H, m), 1.57–1.70 (2H, m), 2.22–2.37 (2H, m), 3.04–3.50 (6H, m), 3.84–3.95 (1H, m), 7.50–7.65 (3H, m), 7.77 (2H, d, J=6 Hz), 7.80 (2H, d, J=8 Hz), 7.97–8.07 (3H, m), 8.15 (1H, d, J=9 Hz), 8.69 (1H, m), 9.06 (1H, s), 9.49 (1H, s), 9.80 (1H, s).

Example 104

Synthesis of (2S)-2-benzenesulfonylamino-3-(3-(4-(N-n-hexylamidino)benzoylamino)propanoylamino) propanoic Acid TFA Salt The title compound is prepared in the same manner as in Example 98 by using n-hexylamine acetate. Yield: 27 mg. MS (SIMS): 546 [M+1]⁺. HPLC retention time: 30.8 min. (under the same conditions as Example 1). ¹H-NMR (DMSO-d₆) δ (ppm): 0.88 (3H, t, J=6 Hz), 1.20–1.43 (6H, m), 1.58–1.70 (2H, m), 2.24–2.37 (2H, m), 3.05–3.55 (6H, m), 3.85–3.96 (1H, m), 7.50–7.67 (3H, m), 7.73–7.85 (4H, m), 7.95–8.08 (3H, m), 8.15 (1H, d, J=9 Hz), 8.70 (1H, t, J=5.5 Hz), 9.07 (1H, s), 9.49 (1H, s), 9.81 (1H, s).

Example 105

Synthesis of (2S)-2-benzenesulfonylamino-3-(3-(4-(N-cyclohexylamidino)benzoylamino) propanoylamino)propanoic Acid TFA Salt The title compound is prepared in the same manner as in Example 98 by using cyclohexylamine acetate.

Yield: 10 mg. MS (SIMS): 544 [M+1]⁺. HPLC retention time: 24.9 min. (under the same conditions as Example 1). ¹H-NMR (DMSO-d₆) δ (ppm): 1.10–1.43 (5H, m), 1.59–2.03 (5H, m), 2.22–2.35 (2H, m), 3.10–3.84 (6H, m), 6.55 (1H, s), 7.50–7.65 (3H, m), 7.73–7.80 (4H, m), 7.95–8.07 (4H, m), 8.73 (1H, t, J=5 Hz), 9.10 (1H, s), 9.43 (1H, s), 9.60 (1H, m).

Example 106

Synthesis of (2S)-2-benzenesulfonylamino-3-(3-(4-(N-benzylamidino)benzoylamino)propanoylamino) propanoic Acid TFA Salt The title compound is prepared in the same manner as in Example 98 by using benzylamine acetate.

Yield: 66.5 mg. MS (SIMS): 552 [M+1]⁺. HPLC retention time: 25.1 min. (under the same conditions as Example 1). ¹H-NMR (DMSO-d₆) δ (ppm): 2.25–2.40 (2H, m), 3.05–3.20 (1H, m), 3.28–3.68 (3H, m), 3.85–3.99 (1H, m), 4.68 (2H, d, J=6 Hz), 7.32–7.48 (5H, m), 7.51–7.65 (3H, m), 7.77 (2H, d, J=8 Hz), 7.86 (2H, d, J=8 Hz), 8.02 (2H, d, J=8 Hz), 7.99–8.07 (1H, m), 8.15 (1H, d, J=9 Hz), 8.70 (1H, t, J=5 Hz), 9.28 (1H, s), 9.66 (1H, s), 10.33 (1H, t, J=5 Hz).

The chemical structures of the compounds obtained in Examples 98 to 106 and 117 are as follows.

| Example No. | R³⁸ | R³⁹ |
|---|---|---|
| Example 98 | Me | H |
| Example 99 | Et | H |
| Example 100 | Me | Me |
| Example 101 | NH₂ | H |
| Example 102 | NHAc | H |
| Example 103 | n-Bu | H |
| Example 104 | n-Hexyl | H |
| Example 105 | cyclohexyl | H |
| Example 106 | —CH₂—phenyl | H |
| Example 117 | —COCH₂—phenyl | H |

Example 107

Synthesis of (2S)-2-benzenesulfonylamino-3-(4-(4-(N-methylamidino)phenoxy)butanoylamino) propanoic Acid TFA Salt (1) 4-(4-(N-Methylamidino)phenoxy)butanoic Acid Hydrochloride The compound (650 mg) obtained in Example 56-(1) is dissolved in a mixture of pyridine (12.5 ml) and triethylamine (2.5 ml), and to the mixture is blown hydrogen sulfide gas for one hour at room temperature, and the mixture is stirred at room temperature for 22 hours. The hydrogen sulfide gas is removed by blowing nitrogen gas into the reaction mixture, and the mixture is concentrated under reduced pressure.

The residue is dissolved in acetone (25 ml), and thereto is added methyl iodide (1.04 ml), and the mixture is stirred at 50° C. for 30 minutes. After cooling, the reaction mixture is concentrated under reduced pressure. The residue is dissolved in methanol (10 ml), and thereto is added methylamine acetate (849 mg). The mixture is refluxed at 70° C. for one hour, and after cooling, the reaction mixture is concentrated under reduced pressure. To the mixture is added ether, and the supernatant is removed, and the resultant is concentrated to dryness under reduced pressure.

To the residue is added a mixture of 1N hydrochloric acid (5 ml) and acetic acid (5 ml), and the mixture is heated with stirring at 50–60° C. for 8 hours. The reaction mixture is concentrated under reduced pressure, and acetone is added to the residue. The precipitates are collected by filtration, dissolved in 4N hydrochloric acid in dioxane (10 ml), and the mixture is stirred at room temperature for 30 minutes. The reaction mixture is concentrated under reduced pressure, and to the residue is added acetone. The precipitates are collected by filtration, and dried to give the title compound (587 mg) as a white powder.

(2) (2S)-2-Benzenesulfonylamino-3-(4-(4-(N-methylaminoamidino)phenoxy)butanoylamino)propanoic Acid TFA Salt The compound (683 mg) obtained in Example 54-(4) and the compound (500 mg) obtained in the above (1) are treated in the same manner as in Example 56-(5) to give the title compound (22 mg).

MS (SIMS): 463 [M+1]$^+$. HPLC retention time: 20.5 min. (under the same conditions as Example 1). $^1$H-NMR (DMSO-d$_6$) δ (ppm): 1.80–1.98 (2H, m), 2.07–2.23 (2H, m), 2.97 (3H, d, J=5 Hz), 3.03–3.17 (2H, m), 3.82–3.96 (1H, m), 4.00–4.12 (2H, m), 7.14 (2H, d, J=9 Hz), 7.50–8.22 (9H, m), 8.76 (1H, s), 9.28 (1H, s), 9.56 (1H, s).

Example 108

Synthesis of (2S)-2-benzenesulfonylamino-3-(4-(4-(N-ethylamidino)phenoxy)butanoylamino)propanoic Acid TFA Salt (1) (4-(4-(N-Ethylamidino)phenoxy)butanoic Acid Hydrochloride The title compound is prepared in the same manner as in Example 107-(1) by using ethylamine acetate instead of methylamine acetate.

Yield: 597 mg.

(2) (2S)-2-Benzenesulfonylamino-3-4-(4-(N-ethylamidino)phenoxy)butanoylamino)propanoic Acid TFA Salt The title compound is prepared in the same manner as in Example 107-(2).

Yield: 33 mg. MS (SIMS): 477 [M+1]$^+$. HPLC retention time: 22.7 min. (under the same conditions as Example 1). $^1$H-NMR (DMSO-d$_6$) δ (ppm): 1.23 (3H, t, J=7 Hz), 1.84–1.95 (2H, m), 2.10–2.20 (2H, m), 3.02–3.18 (1H, m), 3.28–3.47 (3H, m), 3.85–3.90 (1H, m), 4.00–4.10 (2H, m), 7.14 (2H, d, J=9 Hz), 7.50–7.65 (3H, m), 7.66–7.80 (4H, m), 7.99 (1H, t, J=5.3 Hz), 8.15 (1H, d, J=7 Hz), 8.78 (1H, s), 9.23 (1H, s), 9.52 (1H, s).

Example 109

Synthesis of (2S)-2-benzenesulfonylamino-3-(4-(4-(N-benzyloxycarbonylamidino)phenoxy)butanoylamino)propanoic Acid TFA Salt (1) (2S)-3-(4-(4-Amidinophenoxy)butanoylamino)-2-benzenesulfonylaminopropanoic Acid TFA Salt The compound obtained in Example 54-(4) is treated in the same manner as in Example 58, and the resultant is purified by HPLC without hydrolysis of ester to give the title compound.

(2) (2S)-2-Benzenesulfonylamino-3-(4-(4-(N-benzyloxycarbonylamidino)phenoxy)butanoylamino)propanoic Acid TFA Salt To a solution of the compound (51 mg) obtained in the above (1) in DMF (2 ml) are added N-(benzyloxycarbonyloxy)succinimide (25 mg) and triethylamine (14 μl), and the mixture is allowed to stand at room temperature for one day. The reaction mixture is concentrated under reduced pressure, and the residue is purified by HPLC, and the fractions containing the title compound are concentrated under reduced pressure. To the residue is added a mixture of 1N hydrochloric acid (2 ml) and acetic acid (2 ml), and the mixture is stirred at 50° C. for 13 hours. The reaction mixture is concentrated under reduced pressure, and the resultant is purified by HPLC to give the title compound (3 mg) as a white powder.

MS (SIMS): 583 [M+1]$^+$. HPLC retention time: 21.0 min. (Column: YMC-ODS 4.6 mmØ×250 mm, Detection: UV 220 nm, Eluent; A solution; 0.1% TFA/water, B solution; 0.1% TFA/acetonitrile, Flow rate: 1 ml/min., Gradient: The concentration of the B solution is increased from 10% at a rate of 3%/min.). $^1$H-NMR (DMSO-d$_6$) δ (ppm): 1.80–2.00 (2H, m), 2.05–2.25 (2H, m), 3.00–3.60 (2H, m), 3.80–4.00 (1H, m), 4.05 (2H, t, J=6.6 Hz), 5.31 (2H, s), 7.11 (2H, d, J=9.2 Hz), 7.30–7.65 (8H, m), 7.70–7.90 (4H, m), 7.97 (1H, bt, J=6 Hz), 8.14 (1H, d, J=8.9 Hz).

Example 110

Synthesis of (2S)-2-benzenesulfonylamino-3-(4-(4-(N-(9-fluorenyl)methoxycarbonylamidino)phenoxy)butanoylamino)propanoic Acid TFA Salt The compound obtained in Example 109-(1) and N-((9-fluorenyl)methoxycarbonyloxy)succinimide are treated in the same manner as in Example 109-(2) to give the title compound.

Yield: 5 mg. MS (SIMS): 671 [M+1]$^+$. HPLC retention time: 22.3 min. (under the same conditions as Example 109). $^1$H-NMR (DMSO-d$_6$) δ (ppm): 1.80–2.00 (2H, m), 2.10–2.25 (2H, m), 3.00–3.40 (2H, m), 3.80–3.95 (1H, m), 4.06 (2H, t, J=6.6 Hz), 4.38 (1H, t, J=7 Hz), 4.59 (2H, d, J=7 Hz), 7.14 (2H, d, J=8.9 Hz), 7.30–7.65 (7H, m), 7.70–7.95 (8H, m), 7.99 (1H, t, J=6 Hz), 8.15 (1H, d, J=9.2 Hz).

Example 111

Synthesis of (2S)-2-benzenesulfonylamino-3-(4-(6-(1-imino-1,2,3,4-tetrahydroisoquinolyl)oxy)butanoylamino)propanoic Acid TFA Salt (1) 6-Methoxy-1-oxo-1,2,3,4-tetrahydroisoquinoline To a solution of 5-methoxy-1-indanone (1.0 g) in TFA (20 ml) is added sodium azide (4.0 g), and the mixture is refluxed for 1.5 hour. After cooling, the reaction mixture is poured into water (100 ml), and the pH value of the mixture is adjusted to pH 7 with sodium hydrogen carbonate. The mixture is extracted with ethyl acetate, and washed with a saturated aqueous sodium hydrogen carbonate solution and a saturated brine, and dried over magnesium sulfate. The desiccant is removed by filtration, and the filtrate is concentrated under reduced pressure. The residue is purified by silica gel column chromatography (silica gel; 100 g, chloroform/methanol=20:1). The fractions containing the title compound are concentrated under reduced pressure to give the title compound (470 mg) as a pale brown powder.

$^1$H-NMR (CDCl$_3$) δ (ppm): 2.97 (2H, t, J=6.5 Hz), 5.35 (2H, ddd, J=2.9, 6.5, 6.5 Hz), 3.85 (3H, s), 6.38 (1H, s), 6.71 (1H, d, J=2.6 Hz), 6.86 (1H, dd, J=2.6, 8.5 Hz), 8.02 (1H, d, J=8.5 Hz).

(2) 1-Oxo-1,2,3,4-tetrahydroisoquinolin-6-ol

To a solution of aluminum chloride (300 mg) and octanethiol (392 μl) in methylene chloride (5 ml) is added dropwise a solution of the compound (200 mg) obtained in the above (1) in methylene chloride (10 ml), and the mixture is stirred at room temperature for five hours. The reaction mixture is concentrated under reduced pressure, and the residue is purified by silica gel column chromatography (silica gel; 70 g, chloroform/methanol=10:1→5:1). The fractions containing the title compound are concentrated under reduced pressure to give the title compound (110 mg) as a pale brown powder.

¹H-NMR (CDCl₃) δ (ppm): 2.87 (2H, t, J=6.5 Hz), 3.46 (2H, ddd, J=2.5, 6.5, 6.5 Hz), 6.64 (1H, d, J=2.5 Hz), 6.73 (1H, dd, J=2, 8.5 Hz), 7.05 (1H, bs), 7.81 (1H, d, J=8.5 Hz), 9.59 (1H, s).

(3) 4-(6-(1-Oxo-1,2,3,4-tetrahydroisoquinolyl)oxy)butanoic Acid Ethyl Ester

To a solution of the compound (110 mg) obtained in the above (2) in DMF (5 ml) are added 4-bromobutanoic acid ethyl ester (132 mg) and potassium carbonate (102 mg), and the mixture is stirred at room temperature for 24 hours. The reaction mixture is poured into water, and extracted with ethyl acetate. The extract is washed successively with a saturated aqueous sodium hydrogen carbonate solution and a saturated brine, and dried over magnesium sulfate. The filtrate is concentrated under reduced pressure to give the title compound (181 mg).

¹H-NMR (CDCl₃) δ (ppm): 1.26 (3H, t, J=7 Hz), 2.13 (2H, tt, J=7 Hz), 2.52 (2H, t, J=7 Hz), 2.96 (2H, t, J=6.3 Hz), 3.49–3.63 (2H, m), 4.06 (2H, t, J=7 Hz), 4.15 (2H, q, J=7 Hz), 6.08 (1H, bs), 6.70 (1H, s), 6.84 (1H, d, J=8.6 Hz), 8.01 (1H, d, J=8.6 Hz).

(4) 4-(6-(1-Imino-1,2,3,4-tetrahydroisoquinolyl)oxy)butanoic Acid TFA Salt

To a solution of the compound (177 mg) obtained in the above (3) in tetrahydrofuran (5 ml) is added a Lawesson's reagent (Tetrahedron Lett., 21, 4061 (1980), 309 mg), and the mixture is stirred at 40–50° C. for 20 minutes. The reaction mixture is concentrated under reduced pressure, and the residue is purified by silica gel column chromatography (silica gel; 50 g, chloroform/methanol=20:1). The fractions containing the title compound are concentrated under reduced pressure. To the residue are added acetone (20 ml) and methyl iodide (238 μl), and the mixture is stirred at 50° C. for one hour. After cooling, the reaction mixture is concentrated under reduced pressure. To the residue are added methanol (20 ml) and ammonium acetate (148 mg), and the mixture is stirred at 70° C. for one hour. After cooling, the mixture is concentrated under reduced pressure. To the residue is added a mixture of 1N hydrochloric acid (20 ml) and acetic acid (20 ml), and the mixture is stirred at 60° C. for 4.5 hours. The mixture is concentrated under reduced pressure, and the resultant is purified by HPLC to give the title compound (88 mg) as a pale brown powder.

¹H-NMR (DMSO-d₆) δ (ppm): 1.96 (2H, t, J=7 Hz), 2.39 (2H, t, J=7 Hz), 2.95 (2H, t, J=7 Hz), 3.47 (2H, m), 4.05–4.20 (2H, m), 7.00–7.10 (2H, m), 7.95 (1H, d, J=9 Hz), 8.70 (1H, s), 8.98 (1H, s), 9.53 (1H, s).

(5) (2S)-2-Benzenesulfonylamino-3-(4-(6-(1-imino-1,2,3,4-tetrahydroisoquinolyl)oxy)butanoylamino)propanoic Acid TFA Salt The compound (95 mg) obtained in Example 54-(4) and the compound (88 mg) obtained in the above (4) are treated in the same manner as in Example 77 to give the title compound (4 mg).

MS (SIMS): 475 [M+1]⁺. HPLC retention time: 22.3 min. (under the same conditions as Example 1). ¹H-NMR (DMSO-d₆) δ (ppm): 1.85–1.95 (2H, m), 2.10–2.20 (2H, m), 2.95 (2H, t, J=6.5 Hz), 3.03–3.16 (1H, m), 3.42–3.52 (3H, m), 3.82–3.92 (1H, m), 4.06 (2H, t, J=7 Hz), 7.02–7.085 (2H, m), 7.50–7.65 (3H, m), 7.77 (2H, d, J=7 Hz), 8.12 (1H, d, J=7 Hz), 8.58 (1H, s), 8.97 (1H, s), 9.36 (1H, s).

The chemical structures of the compounds obtained in Examples 107 to 111 are as follows.

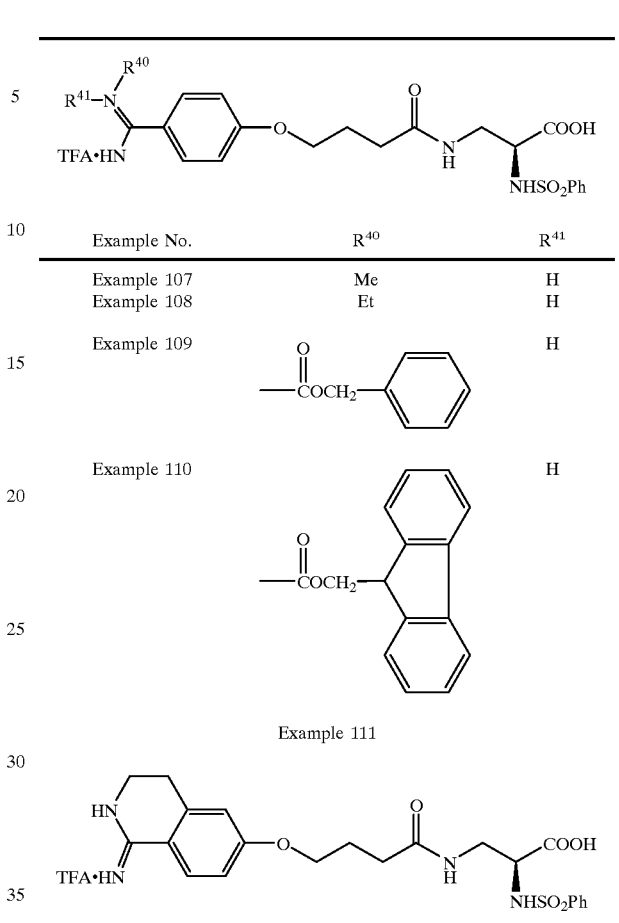

| Example No. | R⁴⁰ | R⁴¹ |
|---|---|---|
| Example 107 | Me | H |
| Example 108 | Et | H |
| Example 109 | —COCH₂—C₆H₅ | H |
| Example 110 | —COCH₂-(fluorenyl) | H |

Example 111

Example 112

Synthesis of (2S)-3-(4-(4-amidinophenoxy)butanoylamino)-2-benzenesulfonylaminopropanoic Acid 5-indanol Ester TFA Salt (1) (2S)-2-Benzyloxycarbonylamino-3-(t-butoxycarbonylamino)propanoic acid 5-indanol Ester To a solution of the compound (480 mg) obtained in Example 1-(2) in methylene chloride (10 ml) are added 5-indanol (209 mg), 4-dimethylaminopyridine (8 mg) and HOBT.H₂O (239 mg). To the mixture is added WSC.HCl (273 mg) at 5–10° C., and the mixture is stirred for 30 minutes, and further stirred at room temperature for two hours. The reaction solution is diluted with ethyl acetate, and washed successively with water and a saturated brine, and dried over magnesium sulfate. The desiccant is removed by filtration, and the filtrate is concentrated under reduced pressure. The resultant is purified by silica gel column chromatography (silica gel; 50 g, n-hexane/ethyl acetate= 3:1) to give the title compound (498 mg).

¹H-NMR (CDCl₃) δ (ppm): 1.43 (9H, s), 2.09 (2H, quint, J=7.6 Hz), 2.80–3.00 (4H, m), 3.60–3.90 (2H, m), 4.55–4.70 (1H, m), 4.91 (1H, bs), 5.14 (2H, s), 5.85–5.90 (1H, m), 6.85 (1H, bd, J=7.3 Hz), 6.96 (1H, bs), 7.18 (1H, d, J=8.3 Hz), 7.30–7.45 (5H, m).

(2) (2S)-2-Benzenesulfonylamino-3-(t-butoxycarbonylamino)propanoic Acid 5-indanol Ester To a solution of the compound (498 mg) obtained in the above (1) in THF (10 ml) are added 10% palladium-carbon (50% wet, 500 mg) and acetic acid (0.07 ml), and the mixture is stirred at room temperature under hydrogen atmosphere for six hours. The insoluble materials are removed by filtration, and to the filtrate are added benzenesulfonyl chloride (212 mg) and triethylamine (0.32 ml), and the mixture is stirred for 12 hours. The reaction solution is diluted with ethyl acetate, and washed with water. The organic layer is concentrated, and the residue is purified by silica gel column chromatography (silica gel; 20 g, n-hexane/ethyl acetate=2:1). The fractions containing the title compound are concentrated under reduced pressure to give the title compound (120 mg).

$^1$H-NMR (CDCl$_3$) δ (ppm): 1.44 (9H, s), 2.06 (2H, quint, J=7.6 Hz), 2.84 (4H, t, J=7.6 Hz), 3.55–3.85 (2H, m), 4.15–4.30 (1H, m), 4.99 (1H, bs), 5.73 (1H, bd, J=7.9 Hz), 6.58 (1H, dd, J=7.9, 2.0 Hz), 6.70 (1H, bs), 7.11 (2H, d, J=7.9 Hz), 7.50–7.75 (3H, m), 7.85–7.95 (2H, m).

(3) (2S)-3-(4-(4-Amidinophenoxy)butanoylamino)-2-benzenesulfonylaminopropanoic Acid 5-indanol Ester TFA Salt The compound (100 mg) obtained in the above (2) is treated in the same manner as in Example 109-(1) to give the title compound (54 mg).

MS (SIMS): 565 [M+1]$^+$. HPLC retention time: 41.7 min. (under the same conditions as Example 1). $^1$H-NMR (DMSO-d$_6$) δ (ppm): 1.80–2.10 (4H, m), 2.15–2.30 (2H, m), 2.78 (4H, t, J=7 Hz), 3.20–3.60 (2H, m), 4.03 (2H, t, J=6.6 Hz), 4.15–4.25 (1H, m), 6.50–6.65 (2H, m), 7.08 (2H, d, J=8.9 Hz), 7.13 (1H, d, J=8.3 Hz), 7.50–7.70 (3H, m), 7.70–7.90 (4H, m), 8.20 (1H, bt, J=6.0 Hz), 8.60 (1H, d, J=8.9 Hz), 8.79 (2H, bs), 9.12 (2H, bs).

Example 113

Synthesis of (2S)-3-(4-(4-amidinophenoxy) butanoylamino)-2-benzenesulfonylaminopropanoic Acid Pivaloyloxymethyl Ester TFA Salt (1) (2S)-2-Benzyloxycarbonylamino-3-(t-butoxycarbonylamino)propanoic Acid Pivaloyloxymethyl Ester To a solution of the compound (200 mg) obtained in Example 1-(2) in DMF (5 ml) are added pivalic acid chloromethyl ester (107 mg) and potassium carbonate (81 mg), and the mixture is stirred at room temperature for 24 hours. The reaction solution is diluted with ethyl acetate, washed with water, and the organic layer is concentrated under reduced pressure. The residue is purified by silica gel column chromatography (silica gel; 50 g, n-hexane/ethyl acetate=2:1) to give the title compound (188 mg).

$^1$H-NMR (CDCl$_3$) δ (ppm): 1.22 (9H, s), 1.42 (9H, s), 3.40–3.70 (2H, m), 4.35–4.50 (1H, m), 4.84 (1H, bs), 5.12 (2H, s), 5.73, 5.85 (2H, ABq, J=5.6 Hz), 5.80–6.00 (1H, m), 7.25–7.45 (2H, m).

(2) (2S)-2-Benzenesulfonylamino-3-(t-butoxycarbonylamino)propanoic Acid Pivaloyloxymethyl Ester The compound obtained in the above (1) is treated in the same manner as in Example 112-(2) to give the title compound (100 mg).

$^1$H-NMR (CDCl$_3$) δ (ppm): 1.17 (9H, s), 1.42 (9H, s), 3.40–3.55 (2H, m), 4.00–4.15 (1H, m), 4.90 (1H, bs), 5.60, 5.64 (2H, ABq, J=6 Hz), 5.75 (1H, bd, J=7.6 Hz), 7.45–7.65 (3H, m), 7.80–7.90 (2H, m).

(3) (2S)-3-(4-(4-Amidinophenoxy)butanoylamino)-2-benzenesulfonylaminopropanoic Acid Pivaloyloxymethyl Ester The compound (77 mg) obtained in the above (2) is treated in the same manner as in Example 112-(3) to give the title compound (72 mg).

MS (SIMS): 563 [M+1]$^+$. HPLC retention time: 36.8 min. (under the same conditions as Example 1). $^1$H-NMR (DMSO-d$_6$) δ (ppm): 111 (9H, s), 1.80–1.95 (2H, m), 2.05–2.20 (2H, m), 3.00–3.50 (2H, m), 3.95–4.10 (3H, m), 5.52 (2H, s), 7.13 (2H, d, J=9.2 Hz), 7.50–7.70 (3H, m), 7.70–7.90 (4H, m), 8.01 (1H, bt, J=6 Hz), 8.46 (1H, d, J=8.6 Hz), 8.80 (2H, bs), 9.12 (2H, bs).

Example 114

Synthesis of (2S)-2-(2-amino) benzenesulfonylamino-3-(3-(4-carbamoylbenzoylamino)propanoylamino)propanoic Acid TFA Salt (1) (2S)-3-(t-Butoxycarbonylamino)-2-(2-nitro) benzenesulfonylaminopropanoic Acid Ethyl Ester The compound obtained in Example 54-(3) is treated in the same manner as in Example 54-(4) by using 2-nitrobenzenesulfonyl chloride to give the title compound.

(2) (2S)-2-(2-Amino)benzenesulfonylamino-3-(3-(4-carbamoylbenzoylamino)propanoylamino)propanoic Acid TFA Salt The title compound is prepared in the same manner as in Example 19.

Yield: 177 mg. MS (SIMS): 478 [M+1]$^+$. HPLC retention time: 9.2 min. (under the same conditions as Example 1). $^1$H-NMR (DMSO-d$_6$) δ (ppm): 2.25–2.38 (2H, m), 3.03–3.50 (4H, m), 3.76 (1H, bs), 5.89 (2H, bs), 6.58 (1H, t, J=7 Hz), 6.78 (1H, d, J=9 Hz), 7.19–7.29 (1H, m), 7.40–7.54 (2H, m), 7.80–7.99 (6H, m), 8.07 (1H, s), 8.55 (1H, t, J=5 Hz).

Example 115

Synthesis of (2S)-3-(3-(4-Amidinobenzoylamino) propanoylamino)-2-(4-ethyl) benzenesulfonylaminopropanoic Acid 5-indanol Ester TFA Salt (1) (2S)-2-Benzyloxycarbonylamino-3-(3-(t-butoxycarbonylamino)propanoylamino)propanoic Acid 5-indanol Ester The compound (2.0 g) obtained in Example 1-(4) is dissolved in a mixture of THF (8 ml) and methanol (8 ml), and thereto is added an aqueous lithium hydroxide solution (LiOH; 546 mg, water; 8 ml), and the mixture is stirred at room temperature for one hour. The mixture is evaporated under reduced pressure to remove the solvent, and the pH value of the resultant is adjusted to pH 1 with 1N hydrochloric acid, and extracted with ethyl acetate. The extract is evaporated under reduced pressure to remove the solvent to give a carboxylic acid compound (1.96 g). The carboxylic acid compound (500 mg) thus obtained and 5-indanol are treated in the same manner as in Example 112-(1) to give the title compound (0.64 g).

(2) (2S)-2-(4-Ethyl)benzenesulfonylamino-3-(3-(t-butoxycarbonylamino)propanoylamino)propanoic Acid 5-indanol Ester The compound (640 mg) obtained in the above (1) is treated in the same manner as in Example 112-(2) to give the title compound (148 mg).

$^1$H-NMR (CDCl$_3$) δ (ppm): 1.26 (3H, t, J=7.6 Hz), 1.44 (9H, s), 2.00–2.15 (2H, m), 2.41 (2H, t, J=5.9 Hz), 2.73 (2H, q, J=7.6 Hz), 2.84 (4H, t, J=7 Hz), 3.30–3.45 (2H, m), 3.65–3.90 (2H, m), 4.15–4.30 (1H, m), 5.10–5.30 (1H, m), 5.75–5.90 (1H, m), 6.40 (1H, bs), 6.56 (1H, dd, J=2, 8 Hz), 6.65 (1H, d, J=2 Hz), 7.11 (1H, d, J=8 Hz), 7.34 (2H, d, J=8 Hz), 7.80 (2H, d, J=8 Hz).

(3) (2S)-3-(3-(4-Amidinobenzoylamino) propanoylamino)-2-(4-ethyl) benzenesulfonylaminopropanoic Acid 5-indanol Ester TFA Salt The compound (148 mg) obtained in the above (2) is treated in the same manner as in Example 22 to give the title compound (84 mg).

MS (SIMS): 606 [M+1]$^+$. HPLC retention time: 41.9 min. (under the same conditions as Example 1). $^1$H-NMR (DMSO-d$_6$) δ (ppm): 1.18 (3H, t, J=8 Hz), 1.90–2.10 (2H, m), 2.37 (2H, t, J=7 Hz), 2.68 (2H, q, J=8 Hz), 2.78 (4H, t, J=7 Hz), 3.30–3.60 (4H, m), 4.10–4.25 (1H, m), 6.51 (1H, dd, J=2, 8 Hz), 6.58 (1H, d, J=2 Hz), 7.12 (1H, d, J=8 Hz), 7.43 (2H, d, J=8 Hz), 7.73 (2H, d, J=8 Hz), 7.86 (2H, d, J=9 Hz), 7.98 (2H, d, J=9 Hz), 8.26 (1H, t, J=6 Hz), 8.52 (1H, d, J=9.2 Hz), 8.72 (1H, t, J=6 Hz), 9.31 (2H, bs), 9.40 (2H, bs).

Example 116

Synthesis of (2S)-3-(3-(4-amidinobenzoylamino) propanoylamino)-2-(4-ethyl) benzenesulfonylaminopropanoic Acid Pivaloyloxymethyl Ester TFA Salt (1) (2S)-2-(4-Ethyl)benzensulfonylamino-3-(t-butoxycarbonylamino)propanoic Acid Pivaloyloxymethyl Ester The compound (310 mg) obtained in Example 113-(1) is treated in the same manner as in Example 112-(2) to give the title compound (65 mg).

$^1$H-NMR (CDCl$_3$) δ (ppm): 1.17 (9H, s), 1.25 (3H, t, J=7.6 Hz), 1.42 (9H, s), 2.71 (2H, q, J=7.6 Hz), 3.40–3.50 (2H, m), 4.00–4.10 (1H, m), 4.85–5.00 (1H, m), 5.60, 5.64 (2H, ABq, J=5 Hz), 5.65–5.80 (1H, m), 7.32 (2H, d, J=8 Hz), 7.75 (2H, d, J=8 Hz).

(2) (2S)-2-(4-Ethyl)benzensulfonylamino-3-(3-(t-butoxycarbonylamino)propanoylamino)propanoic Acid Pivaloyloxymethyl Ester The compound (65 mg) obtained in the above (1) is treated in the same manner as in Example 1-(4) to give the title compound (65 mg). $^1$H-NMR (CDCl$_3$) δ (ppm): 1.17 (9H, s), 1.25 (3H, t, J=7.6 Hz), 1.44 (9H, s), 2.30–2.45 (2H, m), 2.71 (2H, q, J=7.6 Hz), 3.30–3.45 (2H, m), 3.45–3.60 (2H, m), 4.00–4.15 (1H, m), 5.15–5.30 (1H, m), 5.58, 5.67 (2H, ABq, J=5.3 Hz), 6.05–6.20 (1H, m), 6.50–6.65 (1H, m), 7.32 (2H, d, J=8.6 Hz), 7.75 (2H, d, J=8.6 Hz).

(3) (2S)-3-(3-(4-Amidinobenzoylamino) propanoylamino)-2-(4-ethyl) benzenesulfonylaminopropanoic Acid Pivaloyloxymethyl Ester TFA Salt The compound (65 mg) obtained in the above (2) is treated in the same manner as in Example 22 to give the title compound (10 mg).

MS (SIMS): 604 [M+1]$^+$. HPLC retention time: 38.7 min. (under the same conditions as Example 1). $^1$H-NMR (DMSO-d$_6$) δ (ppm): 1.11 (9H, s), 1.18 (3H, t, J=7.6 Hz), 2.20–2.35 (2H, m), 2.67 (2H, q, J=7.6 Hz), 3.05–3.20 (1H, m), 3.20–3.50 (3H, m), 3.90–4.05 (1H, m), 5.53 (2H, s), 7.40 (2H, d, J=8 Hz), 7.66 (2H, d, J=8 Hz), 7.87 (2H, d, J=8 Hz), 8.01 (2H, d, J=8 Hz), 8.04 (1H, bt, J=5.6 Hz), 8.36 (1H, d, J=8.6 Hz), 8.71 (1H, bt, J=5.6 Hz), 9.11 (2H, bs), 9.39 (2H, bs).

The chemical structures of the compounds obtained in Examples 112 to 116 are as follows.

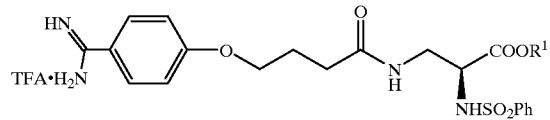

| Example No. | R$^1$ |
|---|---|
| Example 112 | 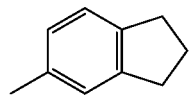 |
| Example 113 | 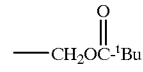 |

Example 114

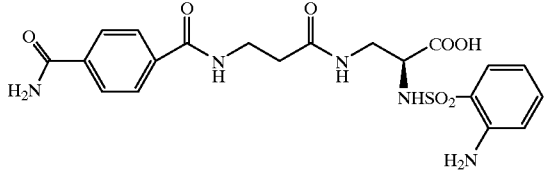

-continued

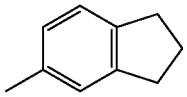

| Example No. | R[1] |
|---|---|
| Example 115 |  |
| Example 116 | —CH$_2$OC(=O)-$^t$Bu |

Example 117

Synthesis of (2S)-3-(3-(4-benzyloxycarbonylamidino)propanoylamino)-2-(4-ethyl)benzenesulfonylaminopropanoic Acid TFA Salt To a solution of the compound (100 mg) obtained in Example 79 in DMF (1 ml) are added N-(benzyloxycarbonyloxy)succinimide (40 mg) and triethylamine (27 μl), and the mixture is allowed to stand at room temperature for one day. The reaction mixture is concentrated under reduced pressure, and the residue is purified by HPLC, and the fractions containing the title compound are concentrated under reduced pressure. The residue is dissolved in a mixture of THF (2 ml) and methanol (2 ml), and thereto is added an aqueous lithium hydroxide solution (LiOH; 9.6 mg, water; 2 ml), and the mixture is stirred at room temperature for two hours. The mixture is evaporated under reduced pressure, and the pH value of the resultant is adjusted to pH 2 with 1N hydrochloric acid, and then purified by HPLC to give the title compound (15 mg) as a white powder.

MS (SIMS): 624 [M+1]$^+$. HPLC retention time: 34.7 min. (under the same conditions as Example 1). $^1$H-NMR (DMSO-d$_6$) δ (ppm): 1.17 (3H, t, J=7 Hz), 2.20–2.35 (2H, m), 2.66 (2H, q, J=7 Hz), 3.05–3.20 (1H, m), 3.25–3.50 (3H, m), 3.80–4.00 (1H, m), 5.28 (2H, s), 7.35–7.50 (7H, m), 7.67 (2H, d, J=8 Hz), 7.90–8.10 (6H, m), 8.66 (1H, bt, J=5 Hz).

Example 118

Platelet Aggregation Inhibitory Activity

The compounds of Examples 72 to 116 were tested in the same manner as in Example 17. The test results of the test compounds are shown in Table 3.

TABLE 3

| Test Compound | IC$_{50}$ (nM) |
|---|---|
| The compound of Example 72 | 52 |
| The compound of Example 73 | 162 |
| The compound of Example 74 | 14 |

TABLE 3-continued

| Test Compound | IC$_{50}$ (nM) |
|---|---|
| The compound of Example 75 | 34 |
| The compound of Example 76 | 17 |
| The compound of Example 77 | 65 |
| The compound of Example 78 | 16 |
| The compound of Example 80 | 17 |
| The compound of Example 81 | 28 |
| The compound of Example 82 | 31 |
| The compound of Example 83 | 30 |
| The compound of Example 84 | 22 |
| The compound of Example 85 | 26 |
| The compound of Example 86 | 56 |
| The compound of Example 87 | 25 |
| The compound of Example 88 | 44 |
| The compound of Example 89 | 26 |
| The compound of Example 90 | 15 |
| The compound of Example 91 | 23 |
| The compound of Example 92 | 37 |
| The compound of Example 93 | 93 |
| The compound of Example 94 | 31 |
| The compound of Example 95 | 15 or 17 |
| The compound of Example 96 | 57 |
| The compound of Example 97 | 49 |
| The compound of Example 98 | 57 |
| The compound of Example 99 | 17 |
| The compound of Example 100 | 28 |
| The compound of Example 101 | 103 |
| The compound of Example 102 | 35 |
| The compound of Example 103 | 25 |
| The compound of Example 104 | 28 |
| The compound of Example 105 | 22 |
| The compound of Example 106 | 116 |
| The compound of Example 107 | 29 |
| The compound of Example 108 | 51 |
| The compound of Example 111 | 41 |
| The compound of Example 113 | 48 |
| The compound of Example 114 | 35 |
| The compound of Example 116 | 103 |

Example 119

Specificity for Cell Adhesion Reaction (1) Preparation of Human Platelet

The blood was taken out from the elbow vein of a normal male volunteer, and mixed with 1/10 volume of 3.8% sodium citrate. The blood was centrifuged at 1,000 rpm (150 g) for 10 minutes, and the supernatant is collected as a platelet rich plasma (PRP). The precipitates are centrifuged at 11,000 rpm (6000 g) for two minutes, and the supernatant is collected as a platelet poor plasma (PPP). To PRP is added prostaglandin $I_2$ ($PGI_2$) at a final concentration of 50 ng/ml, and the mixture was centrifuged at 11000 rpm for two minutes to give human platelet. The platelet was activated by washing with 3.8 mM HEPES-buffer (pH 7.4, Tyrode-HEPES buffer) containing 0.14 M sodium chloride, 2.7 mM potassium chloride, 3.7 mM sodium dihydrogen phosphate, 0.98 mM magnesium chloride, 1 mg/ml glucose, 50 ng/ml $PGI_2$ and 0.35% bovine serum albumin (BSA), adding thereto 5 μM epinephrine, and 30 μM ADP (adenosine diphosphate), followed by being allowed to stand at room temperature for five minutes. To the activated platelet was added 0.05% p-formaldehyde, and the mixture was allowed to stand at room temperature for 30 minutes to give the fixed platelet, which was suspended in Tyrode-HEPES buffer to give a platelet suspension of a concentration of $2 \times 10^8$ $ml^{-1}$.

(2) Binding Assay of Platelet to Adhesive Protein

Human fibrinogen from which fibronectin was previously removed by passing through gelatin-cepharose, human fibronectin or human vitronectin was diluted with 0.1 M aqueous sodium hydrogen carbonate solution to a concentration of 5 μg/ml, and the protein solution is put into a 96-well microplate at a volume of 200 μl/well. The microplate was allowed to stand at 4° C. overnight. The plate was washed with phosphate buffered saline (PBS), and subjected to blocking with 3% BSA at 37° C. for one hour. To the plate were added a platelet suspension (final concentration, $10^8$ $ml^{-1}$) and a test compound of various concentrations (total volume, 200 μl/well), and the plate was incubated at 37° C. for 60 minutes. The plate was treated with 1000-fold diluted enzyme (HRP)-labelled anti-mouse IgG polyclonal antibody at 37° C. for 60 minutes, and thereto was added HRP chromogenic substrate (0.1 M phosphate buffer containing 0.4 mg/ml O-phenylenediamine, 0.01% hydrogen peroxide, 0.1 M citric acid, pH 5), and reacted at room temperature for 15 minutes. The reaction was terminated by adding thereto 4.5 M sulfuric acid at a volume of 25 μl/well, and the absorbance at 490 nm was measured.

The inhibitory activity ($IC_{50}$) against the binding between various adhesive proteins and platelet is shown in Table 4.

TABLE 4

Test results (receptor binding inhibition ($IC_{50}$, M))

| Test Compound | Fibrinogen | Fibronectin | Bitronectin |
|---|---|---|---|
| The compound of Ex. 1 | $4.6 \times 10^{-9}$ | $2.0 \times 10^{-7}$ | $1.0 \times 10^{-6}$ |
| The compound of Ex. 2 | $1.2 \times 10^{-8}$ | $1.2 \times 10^{-7}$ | $7.5 \times 10^{-5}$ |
| The compouhd of Ex. 18 | $7.3 \times 10^{-9}$ | $4.0 \times 10^{-7}$ | $8.9 \times 10^{-6}$ |
| The compound of Ex. 19 | $5.0 \times 10^{-9}$ | $4.7 \times 10^{-8}$ | $1.2 \times 10^{-6}$ |
| The compound of Ex. 20 | $7.3 \times 10^{-9}$ | $7.9 \times 10^{-8}$ | $5.0 \times 10^{-7}$ |
| The compound of Ex. 21 | $2.2 \times 10^{-9}$ | $3.1 \times 10^{-7}$ | $2.4 \times 10^{-7}$ |
| The compound of Ex. 57 | $7.1 \times 10^{-9}$ | $1.2 \times 10^{-6}$ | $7.5 \times 10^{-6}$ |
| The compound of Ex. 58 | $2.4 \times 10^{-8}$ | $6.1 \times 10^{-7}$ | $8.0 \times 10^{-6}$ |
| The compound of Ex. 59 | $1.2 \times 10^{-8}$ | $6.1 \times 10^{-7}$ | $3.3 \times 10^{-6}$ |
| The compound of Ex. 60 | $1.5 \times 10^{-9}$ | $9.4 \times 10^{-7}$ | $1.1 \times 10^{-6}$ |
| The compound of Ex. 61 | $1.0 \times 10^{-9}$ | $2.5 \times 10^{-8}$ | $3.8 \times 10^{-7}$ |
| The compound of Ex. 62 | $1.1 \times 10^{-9}$ | $4.5 \times 10^{-9}$ | $2.4 \times 10^{-7}$ |
| The compound of Ex. 63 | $2.2 \times 10^{-9}$ | $4.1 \times 10^{-8}$ | $1.3 \times 10^{-7}$ |
| The compound of Ex. 64 | $2.4 \times 10^{-8}$ | $2.8 \times 10^{-7}$ | $4.8 \times 10^{-6}$ |
| The compound of Ex. 68 | $1.2 \times 10^{-8}$ | $9.9 \times 10^{-7}$ | $2.7 \times 10^{-6}$ |
| The compound of Ex. 69 | $9.8 \times 10^{-9}$ | $6.0 \times 10^{-8}$ | $9.7 \times 10^{-7}$ |
| The compound of Ex. 74 | $2.2 \times 10^{-8}$ | $5.4 \times 10^{-7}$ | $3.5 \times 10^{-6}$ |
| The compound of Ex. 75 | $8.1 \times 10^{-9}$ | $1.1 \times 10^{-7}$ | $1.6 \times 10^{-6}$ |
| The compound of Ex. 76 | $6.3 \times 10^{-9}$ | $5.1 \times 10^{-7}$ | $5.4 \times 10^{-7}$ |
| The compound of Ex. 77 | $6.7 \times 10^{-9}$ | $5.4 \times 10^{-8}$ | $6.7 \times 10^{-7}$ |

TABLE 4-continued

Test results (receptor binding inhibition ($IC_{50}$, M))

| Test Compound | Fibrinogen | Fibronectin | Bitronectin |
|---|---|---|---|
| The compound of Ex. 78 | $9.0 \times 10^{-9}$ | $2.5 \times 10^{-8}$ | $1.6 \times 10^{-7}$ |
| The compound of Ex. 80 | $1.0 \times 10^{-8}$ | $3.9 \times 10^{-7}$ | $4.9 \times 10^{-6}$ |
| The compound of Ex. 82 | $1.2 \times 10^{-9}$ | $1.9 \times 10^{-8}$ | $2.7 \times 10^{-7}$ |
| The compound of Ex. 83 | $2.2 \times 10^{-8}$ | $7.7 \times 10^{-7}$ | $7.8 \times 10^{-6}$ |
| The compound of Ex. 85 | $4.8 \times 10^{-9}$ | $2.0 \times 10^{-8}$ | $2.7 \times 10^{-7}$ |
| The compound of Ex. 86 | $1.1 \times 10^{-9}$ | $1.2 \times 10^{-7}$ | $5.0 \times 10^{-7}$ |
| The compound of Ex. 87 | $1.2 \times 10^{-8}$ | $2.1 \times 10^{-7}$ | $2.7 \times 10^{-6}$ |
| The compound ot Ex. 91 | $4.7 \times 10^{-9}$ | $5.0 \times 10^{-8}$ | $1.3 \times 10^{-6}$ |
| The compound of Ex. 92 | $3.9 \times 10^{-9}$ | $2.4 \times 10^{-8}$ | $5.0 \times 10^{-7}$ |
| The compound of Ex. 93 | $1.5 \times 10^{-8}$ | $9.5 \times 10^{-8}$ | $3.5 \times 10^{-6}$ |
| The compound of Ex. 95 | $8.4 \times 10^{-9}$ | $3.3 \times 10^{-8}$ | $6.3 \times 10^{-7}$ |

Example 120

Platelet Aggregation Inhibitory Activity (ex vivo)

Method

A canula for collecting blood was inserted into the left common carotid artery of a guinea pig which was anesthetized with pentobarbital (30 mg/kg, i.p.). The blood (1 ml) was taken with a syringe containing $\frac{1}{10}$ volume of 3.8% sodium citrate (Kettin-citrate, manufactured by Kokusai Shiyaku Ltd.), and the platelet aggregation ability thereof was measured (as a value before administration). Then, a test compound was orally administered to the guinea pig at a dose of 0.1 mg/kg in a volume of 5 ml/kg, and the blood was collected periodically likewise at 0.5, 1, 2, 4 and 6 hours after the administration of the test compound, and the platelet aggregation ability thereof was measured.

The determination of the platelet aggregation ability was carried out by turbidimetry using a Hematracer (Niko Bioscience) as follows. That is, the blood was centrifuged at 4500 rpm at room temperature for 10 seconds, and the supernatant was considered as platelet rich plasma (PRP), and the precipitate was centrifuged at 11000 rpm for two minutes and its supernatant was considered as platelet poor plasma (PPP), and the photo-transmittance of the PRP and the PPP was adjusted to 0%, and 100%, respectively. A cubet containing PRP (200 μl) was inserted to a measurement well, and centrifuged at 1000 rpm at 37° C. for two minutes, and thereto was added a platelet aggregator; ADP (adenosine diphosphate, Sigma Ltd., 20 μl, final concentration; 10 μg/ml), and the maximum aggregation rate was measured. From the maximum aggregation rate before the administration of the test compound (MAR control) and the maximum aggregation rate after the administration of the test compound (MAR sample), the platelet aggregation inhibitory rate of each test compound was estimated according to the following equation.

Inhibitory rate (%)=(1−(MAR sample/MAR control))×100

The periodical change in the platelet aggregation inhibitory rate of each test compound at a dose of 0.1 mg/kg of oral administration is shown in Table 5.

TABLE 5

Test results (platelet aggregation inhibitory rate (%))

| Test Compound | 0.5 hr | 1 hr | 2 hrs | 4 hrs | 6 hrs |
|---|---|---|---|---|---|
| The Compound of Ex. 1 | 100 | 100 | 100 | 100 | 100 |
| The Compound of Ex. 2 | 87 | 78 | 67 | 32 | 13 |
| The Compound of Ex. 18 | 54 | 100 | 100 | 73 | 66 |
| The Compound of Ex. 19 | 86 | 93 | 91 | 89 | 91 |
| The Compound of Ex. 20 | 76 | 91 | 99 | 100 | 100 |
| The Compound of Ex. 21 | 96 | 99 | 100 | 100 | 100 |
| The Compound ot Ex. 61 | 45 | 32 | 25 | 48 | 0 |
| The Compound of Ex. 62 | 63 | 69 | 63 | 56 | 50 |
| The Compound of Ex. 63 | 57 | 48 | 26 | 3 | 0 |
| The Compound of Ex. 64 | 50 | 0 | 0 | 0 | 0 |
| The Compound of Ex. 67 | 88 | 71 | 69 | 31 | 10 |
| The Compound of Ex. 69 | 69 | 39 | 22 | 6 | 3 |
| The Compound of Ex. 74 | 92 | 100 | 100 | 100 | 100 |
| The Compound of Ex. 75 | 74 | 82 | 100 | 90 | 74 |
| The Compound of Ex. 76 | 100 | 100 | 100 | 100 | 100 |
| The Compound of Ex. 77 | 100 | 100 | 100 | 100 | 97 |
| The Compound of Ex. 78 | 99 | 100 | 100 | 100 | 100 |
| The Compound of Ex. 80 | 100 | 100 | 75 | 79 | 74 |
| The Compound of Ex. 82 | 81 | 66 | 54 | 52 | 51 |
| The Compound of Ex. 83 | 50 | 47 | 48 | 32 | 41 |
| The Compound of Ex. 85 | 36 | 41 | 44 | 31 | 17 |
| The Compound of Ex. 86 | 46 | 0 | 0 | 0 | 0 |
| The Compound of Ex. 87 | 100 | 100 | 100 | 100 | 80 |
| The Compound of Ex. 91 | 51 | 41 | 31 | 14 | 39 |
| The Compound of Ex. 92 | 68 | 34 | 24 | 47 | 0 |
| The Compound of Ex. 93 | 4 | 27 | 69 | 44 | 12 |
| The Compound of Ex. 95 | 49 | 49 | 31 | 12 | 18 |
| The Compound of Ex. 98 | 94 | 100 | 100 | 100 | 100 |
| The Compound of Ex. 99 | 100 | 100 | 100 | 100 | 100 |
| The Compound of Ex. 100 | 100 | 100 | 100 | 100 | 100 |

INDUSTRIAL APPLICABILITY 2,3-Diaminopropionic acid derivatives of the present invention are useful as a platelet aggregation inhibitor, a cancer metastasis inhibitor, a wound healing agent or a bone resorption inhibitor.

What is claimed is:

1. A compound of the formula (1):

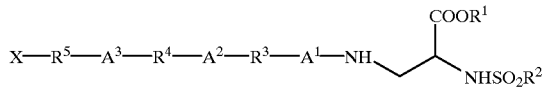

wherein $R^1$ is a hydrogen atom, a lower alkyl group, a cycloalkyl group, a lower alkenyl group, a lower alkynyl group, an aryl group, a heterocyclic group, a substituted lower alkyl group, a substituted cycloalkyl group, a substituted lower alkenyl group, a substituted lower alkynyl group, a substituted aryl group or a substituted heterocyclic group;

$R^2$ is a lower alkyl group, a cycloalkyl group, a lower alkenyl group, a lower alkynyl group, an aryl group, a heterocyclic group, a substituted lower alkyl group, a substituted cycloalkyl group, a substituted lower alkenyl group, a substituted lower alkynyl group, a substituted aryl group or a substituted heterocyclic group;

$A^1$ is —CO— or —CO—$A^4$— (wherein $A^4$ is a residue of an α-amino acid, an α-amino acid derivative, a β-amino acid or a β-amino acid derivative, or a residue of a peptide consisting of 2 or 3 residues thereof);

$A^2$ and $A^3$ are the same or different and each a single bond, —$NR^6$— (wherein $R^6$ is a hydrogen atom or a lower alkyl group), an oxygen atom, $S(O)_n$ (wherein n is 0, 1 or 2), —CO—$NR^7$— (wherein $R^7$ is a hydrogen atom or a lower alkyl group), —$NR^7$—CO— (wherein $R^7$ is the same as defined above), —CO—$A^5$—$NR^8$— (wherein $R^8$ is a hydrogen atom or a lower alkyl group, $A^5$ is a residue of an β-amino acid, an α-amino acid derivative, a β-amino acid or a β-amino acid derivative, or a reside of a dipeptide consisting of 2 residues thereof), —$NR^8$—$A^5$—CO— (wherein $R^8$ and $A^5$ are the same as defined above), a divalent group of a monocyclic hydrocarbons or a divalent group of a monocyclic heterocyclic group;

$R^3$, $R^4$ and $R^5$ are the same or different and each a single bond, or an alkylene, alkenylene or alkynylene group, which may optionally be substituted by 1 to 4 groups selected from the hydroxy group, an oxo group, a halogen atom, an aryl group and a cycloalkyl group, provided that when $A^2$ and $A^3$ are the same or different and each —$NR^6$— (wherein $R^6$ is the same as defined above), an oxygen atom or $S(O)_n$ (wherein n is the same as defined above), $R^4$ should not be a single bond;

the definition for X and the number of atoms comprising a divalent main chain represented by —$R^5$—$A^3$—$R^4$—$A^2$—$R^3$—$A^1$— are shown in the following (a):

(a) X is a group of the formula (4):

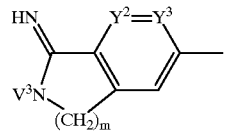

wherein $Y^2$ and $Y^3$ are the same or different and each a methine group or a nitrogen atom, $V^3$ is a hydrogen atom, an alkyl group, a substituted lower alkyl group, a cycloalkyl group, an amino group, an acylamino group, a lower alkyloxycarbonyl group or a lower alkyloxycarbonyl group substituted by an aryl group, m is 2 or 3, and the number of atoms comprising a divalent main chain represented by —$R^5$—$A^3$—$R^4$—$A^2$—$R^3$—$A^1$— is 4 to 9, or a pharmaceutically acceptable salt thereof.

2. The compound according to claim 1, wherein $R^2$ is an aryl group, a substituted aryl group, an aromatic heterocyclic group or a substituted aromatic heterocyclic group, or a pharmaceutically acceptable salt thereof.

3. The compound according to claim 1, wherein $R^2$ is an aryl group, an aromatic heterocyclic group, or an aryl group substituted by 1 or more groups selected from a lower alkyl group, a lower alkyl group substituted by a halogen atom, a lower alkyloxy group, a lower alkyloxy group substituted by a halogen atom, an amino group, a dialkylamino group, an acylamino group, a halogen atom, a nitro group and a carboxyl group, or a pharmaceutically acceptable salt thereof.

4. The compound according to any one of claims 1 to 3, wherein $A^1$ is —CO—, and $R^3$ is —$CH_2$—$CHR^9$— (wherein $R^9$ is a hydrogen atom or a lower alkyl group), or a pharmaceutically acceptable salt thereof.

5. The compound according to claim 4, wherein the definition for X and the number of atoms comprising a divalent main chain represented by —$R^5$—$A^3$—$R^4$—$A^2$—$R^3$—$A^1$— are defined by the following (a), or a pharmaceutically acceptable salt thereof:

(a) X is a group of the formula (4):

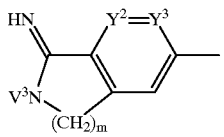

wherein $Y^2$, $Y^3$, $V^3$ and m are the same as defined above, and the number of atoms comprising a divalent main chain represented by $-R^5-A^3-R^4-A^2-R^3-A^1-$ is 5 or 6.

6. The compound according to claim 5, which is a compound of the formula (5):

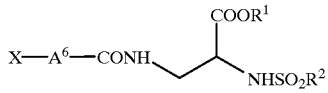

wherein $R^1$ and $R^2$ are the same as defined above, X and $A^6$ are defined by the following (a), or a pharmaceutically acceptable salt thereof:

(a) X is a group of the formula (4):

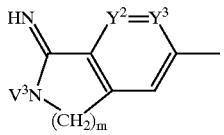

wherein $Y^2$, $Y^3$, $V^3$ and m are the same as defined above, $A^6$ is a divalent group selected from the following groups:

$-(CH_2)_f-CONR^{10}-CH_2-CHR^9-$ ($R^9$ and $R^{10}$ are the same as defined above, and f is 0 or 1);
$-Y^4-(CH_2)_d-$ ($Y^4$ is a methylene group or an oxygen atom and d is 3 or 4);
$-(CH_2)_f-CO-(CH_2)_d-$ (f and d are the same as defined above);
$-(CH_2)_f-CH(OH)-(CH_2)_d-$ (f and d are the same as defined above);
$-NR^{10}CO-(CH_2)_d-$ ($R^{10}$ is a hydrogen atom or a lower alkyl group and d is the same as defined above);
$-Y^4-(CH_2)_g-Y^5-$ ($Y^4$ is the same as defined above, $Y^5$ is an oxygen atom or $-NR^{11}-$ ($R^{11}$ is a hydrogen atom or a lower alkyl group), and g is 2 to 4);

a group of the formula:

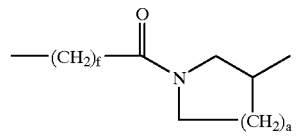

wherein a is 1 or 2 and f is the same as defined above;
a group of the formula:

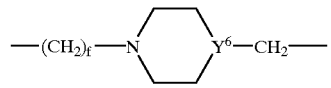

wherein f is the same as defined above, $Y^6$ is a methine group or a nitrogen atom;
a group of the formula:

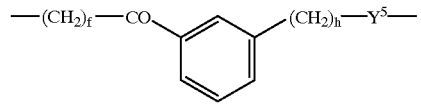

wherein $Y^5$ and f are the same as defined above, and h is 0 or 1;
a group of the formula:

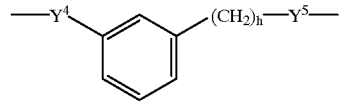

wherein $Y^4$, $Y^5$ and h are the same as defined above.

7. The compound according to claim 6, wherein X and $A^6$ are defined by the following (a), or a pharmaceutically acceptable salt thereof:

(a) X is a group of the formula (4):

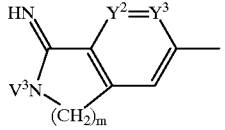

wherein $Y^2$, $Y^3$, $V^3$ and m are the same as defined above, $A^6$ is a divalent group selected form the following groups:

$-(CH_2)_f-CONR^{10}-CH_2-CHR^9-$ ($R^9$, $R^{10}$ and f are the same as defined above);
$-Y^4-(CH_2)_d-$ ($Y^4$ and d are the same as defined above);
$-(CH_2)_f-CO-(CH_2)_d-$ (f and d are the same as defined above);

a group of the formula:

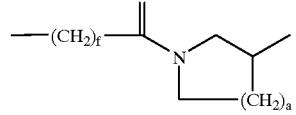

wherein a and f are the same as defined above;

a group of the formula:

wherein f and $Y^6$ are the same as defined above.

8. The compound according to claim 7, wherein X is a group of the formula (4):

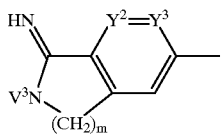

wherein $Y^2$, $Y^3$, $V^3$ and m are the same as defined above, $A^2$ and $A^3$ are the same or different and each a single bond, —$NR^6$— ($R^6$ is the same as defined above), an oxygen atom, $S(O)_n$ (n is the same as defined above), —CO—$NR^7$— ($R^7$ is the same as defined above), $NR^7$—CO— ($R^7$ is the same as defined above), —CO—$A^5$—$NR^8$— ($A^5$ and $R^8$ are the same as defined above), —$NR^8$—$A^5$—CO— ($R^8$ and $A^5$ are the same as defined above), a divalent group of aliphatic monocyclic hydrocarbons or a divalent group of aliphatic monocyclic heterocyclic group, or a pharmaceutically acceptable salt thereof.

9. The compound according to claim 1, wherein the stereoconfiguration of the 2-position thereof is S-configuration, or a pharmaceutically acceptable salt thereof.

10. A pharmaceutical composition comprising an effective amount of a compound of claim 1; and a pharmaceutically acceptable carrier.

11. A method of inhibiting platelets which comprises administering an effective amount of a compound according to claim 1 to a patient in need thereof.

12. A method of inhibiting cancer metastasis which comprises administering an effective amount of a compound according to claim 1 to a patient in need thereof.

13. A method of healing a wound which comprises administering an effective amount of a compound according to claim 1 or 9 to a patient suffering from a wound.

14. A method of inhibiting bone resorption which comprises administering an effective amount of a compound according to claim 1 or 9 to a patient in need thereof.

* * * * *